US012600987B2

(12) United States Patent
Asokan et al.

(10) Patent No.: US 12,600,987 B2
(45) Date of Patent: Apr. 14, 2026

(54) COMPOSITIONS AND METHODS FOR CIRCULAR RNA EXPRESSION

(71) Applicant: Duke University, Durham, NC (US)

(72) Inventors: Aravind Asokan, Durham, NC (US); Rita Meganck, Durham, NC (US)

(73) Assignee: Duke University, Durham, NC (US)

( * ) Notice: Subject to any disclaimer, the term of this patent is extended or adjusted under 35 U.S.C. 154(b) by 749 days.

(21) Appl. No.: 17/796,874

(22) PCT Filed: Apr. 1, 2021

(86) PCT No.: PCT/US2021/025463
§ 371 (c)(1),
(2) Date: Aug. 1, 2022

(87) PCT Pub. No.: WO2021/159129
PCT Pub. Date: Aug. 12, 2021

(65) Prior Publication Data
US 2023/0072954 A1      Mar. 9, 2023

Related U.S. Application Data

(60) Provisional application No. 62/969,758, filed on Feb. 4, 2020.

(51) Int. Cl.
*C12N 15/86*      (2006.01)
*A61K 48/00*      (2006.01)

(52) U.S. Cl.
CPC .............. *C12N 15/86* (2013.01); *A61K 48/00* (2013.01); *C12N 2750/14143* (2013.01); *C12N 2750/14171* (2013.01); *C12N 2830/42* (2013.01); *C12N 2840/203* (2013.01); *C12N 2840/44* (2013.01)

(58) Field of Classification Search
None
See application file for complete search history.

(56) References Cited

FOREIGN PATENT DOCUMENTS

| CN | 107447033 | 12/2017 |
| WO | 03095647 A2 | 11/2003 |
| WO | 2006021724 A2 | 3/2006 |
| WO | 2019094486 A1 | 5/2019 |

OTHER PUBLICATIONS

Rybak-Wolf, A. et al, Circular RNAs in the Mammalian Brain are Highly Abundant, Conserved and Dynamically Expressed, Molecular Cell, vol. 58, Issue 5, Jun. 4, 2015, pp. 870-885 (Year: 2015).*
Rybak-Wolf, et al, Circular RNAs in the Mammalian Brain Are Highly Abundant, Conserved, and Dynamically Expressed, Molecular Cell, 58, 870-885, Jun. 4, 2015 (Year: 2015).*

Extended European Search Report for EP Application No. 21750796.1 mailed Feb. 2, 2024 (9 pages).
Abelson J., et al., "tRNA Splicing," Journal of Biological Chemistry, May 1998, vol. 273, No. 21, pp. 12685-12688.
Ashwal-Fluss R., et al., "CircRNA Biogenesis Competes with Pre-mRNA Splicing," Molecular Cell, Oct. 2, 2014, vol. 56, No. 1, pp. 55-66.
Baranick B.T., et al., "Splicing Mediates the Activity of Four Putative Cellular Internal Ribosome Entry Sites," Proceedings of the National Academy of Sciences of the United States of America, Mar. 25, 2008, vol. 105, No. 12, pp. 4733-4738.
Borchardt E.K., et al., "Inducing Circular RNA Formation Using the CRISPR Endoribonuclease Csy4," RNA, May 2017, vol. 23, No. 5, pp. 619-627.
Chen X., et al., "TiProD: The Tissue-Specific Promoter Database," Nucleic Acids Research, Jan. 1, 2006, vol. 34, pp. D104-D107.
Chen Y.G., et al., "Sensing Self and Foreign Circular RNAs by Intron Identity," Molecular Cell, Jul. 20, 2017, vol. 67, No. 2, pp. 228-238.
Danan M., et al., "Transcriptome-Wide Discovery of Circular RNAs in Archaea," Nucleic Acids Research, Apr. 2012, vol. 40, No. 7, pp. 3131-3142.
Douin V., et al., "Use and Comparison of Different Internal Ribosomal Entry Sites (IRES) in Tricistronic Retroviral Vectors," BMC Biotechnology, Jul. 27, 2004, vol. 4, No. 16, 12 pages.
Enuka Y., et al., "Circular RNAs Are Long-Lived and Display Only Minimal Early Alterations in Response to a Growth Factor," Nucleic Acids Research, Feb. 18, 2016, vol. 44, No. 3, pp. 1370-1383.
Filonov G.S., et al., "Broccoli: Rapid Selection of an RNA Mimic of Green Fluorescent Protein by Fluorescence-Based Selection and Directed Evolution," Journal of the American Chemical Society, Nov. 19, 2014, vol. 136, No. 46, pp. 16299-16308.
Garikipati V.N.S., et al., "Circular RNA CircFndc3b Modulates Cardiac Repair after Myocardial Infarction via FUS/VEGF-A Axis," Nature Communication, Sep. 20, 2019, vol. 10, No. 1, 14 pages.
Hansen T.B., et al., "Natural RNA Circles Function as Efficient MicroRNA Sponges," Nature, Feb. 27, 2013, vol. 495, pp. 384-388.
Hurowitz E.H., et al., "Genome-Wide Analysis of mRNA Lengths in *Saccharomyces cerevisiae*," Genome Biology, Dec. 22, 2003, vol. 5, No. R2, 14 pages.
Jeck W.R., et al., "Circular RNAs are Abundant, Conserved, and Associated with ALU Repeats," RNA, Feb. 2013, vol. 19, No. 2, pp. 141-157.
Jiang Q., et al., "Circular RNA-ZNF532 Regulates Diabetes-Induced Retinal Pericyte Degeneration and Vascular Dysfunction," Journal of Clinical Investigation, Jul. 1, 2020, vol. 130, No. 7, pp. 3833-3847.
Kramer M.C., et al., "Combinatorial Control of *Drosophila* Circular RNA Expression by Intronic Repeats, hnRNPs, and SR Proteins," Genes & Development, Oct. 15, 2015, vol. 29, No. 20, pp. 2168-2182.

(Continued)

*Primary Examiner* — Allison M Fox
*Assistant Examiner* — Marisol Ann O'Neill
(74) *Attorney, Agent, or Firm* — Polsinelli PC

(57) ABSTRACT

The present disclosure provides nucleic acid molecules encoding for at least two circular RNA (circRNAs), adeno-associated virus (AAV) particles including nucleic acid molecules encoding for at least two circRNAs, pharmaceutical compositions, and methods for delivering such to a subject.

15 Claims, 37 Drawing Sheets
(32 of 37 Drawing Sheet(s) Filed in Color)
Specification includes a Sequence Listing.

(56) References Cited

OTHER PUBLICATIONS

Lavenniah A., et al., "Engineered Circular RNA Sponges Act as Mirna Inhibitors to Attenuate Pressure Overload-Induced Cardiac Hypertrophy," Molecular Therapy, Jun. 2, 2020, vol. 28, No. 6, pp. 1506-1517.

Li C., et al., "Engineering Adeno-Associated Virus Vectors for Gene Therapy," Nature Reviews Genetics, Apr. 2020, vol. 21, No. 4, pp. 255-272.

Liang D., et al., "Short Intronic Repeat Sequences Facilitate Circular RNA Production," Genes & Development, Oct. 15, 2014, vol. 28, No. 20, pp. 2233-2247.

Litke J.L., et al., "Highly Efficient Expression of Circular RNA Aptamers in Cells Using Autocatalytic Transcripts," Nature Biotechnology, Jun. 2019, vol. 37, No. 6, pp. 667-675.

Lu Z., et al., "Metazoan tRNA Introns Generate Stable Circular RNAs in Vivo," RNA, Sep. 2015, vol. 21, No. 9, pp. 1554-1565.

Madigan V.J., et al., "Engineering AAV Receptor Footprints for Gene Therapy," Current Opinion in Virology, Jun. 2016, vol. 18, pp. 89-96.

Meganck R.M., et al., "Engineering Highly Efficient Backsplicing and Translation of Synthetic CircRNAs," Molecular Therapy Nucleic Acids, Jan. 16, 2021, vol. 23, pp. 821-834.

Meganck R.M., et al., "Tissue-Dependent Expression and Translation of Circular RNAs with Recombinant AAV Vectors in Vivo," Molecular Therapy Nucleic Acids, Dec. 7, 2018, vol. 13, pp. 89-98.

Memczak S., et al., "Circular RNAs are a Large Class of Animal RNAs with Regulatory Potency," Nature, Mar. 21, 2013, vol. 495, No. 7441, pp. 333-338.

Noto J.J., et al., "Engineering and Expressing Circular RNAs via tRNA Splicing," RNA Biology, Apr. 12, 2017, vol. 14, No. 8, pp. 978-984.

Othman Z., et al., "Functional Analysis of Kaposi's Sarcoma-Associated Herpesvirus vFLIP Expression Reveals a New Mode of IRES-Mediated Translation," RNA, Nov. 2014, vol. 20, No. 11, pp. 1803-1814.

Panda A.C., et al., "High-Purity Circular RNA Isolation Method (RPAD) Reveals Vast Collection of Intronic CircRNAs," Nucleic Acids Research, Jul. 7, 2017, vol. 45, No. 12, 13 pages.

Pyle A.M., "Group II Intron Self-Splicing," Annual Review of Biophysics, Jul. 5, 2016, vol. 45, pp. 183-205.

Robic A., et al., "Beyond Back Splicing, A Still Poorly Explored World: Non-Canonical Circular RNAs," Genes (Basel), Sep. 22, 2020, vol. 11, No. 9, 11 pages.

Schmidt C.A., et al., "tRNA Introns: Presence, Processing, and Purpose," Wiley Interdisciplinary Reviews RNA, May 2020, vol. 11, No. 3, 1 pages.

Schneider C.A., et al., "NIH Image to ImageJ: 25 Years of Image Analysis," Nature Methods, Jul. 2012, vol. 9, No. 7, pp. 671-675.

Shen S., et al., "Engraftment of a Galactose Receptor Footprint onto Adeno-Associated Viral Capsids Improves Transduction Efficiency," Journal of Biological Chemistry, Oct. 4, 2013, vol. 288, No. 40, pp. 28814-28823.

Terenin I.M., et al., "A Researcher's Guide to the Galaxy of IRESs," Cellular and Molecular Life Sciences, Apr. 2017, vol. 74, No. 8, pp. 1431-1455.

Wang D., et al., "Adeno-Associated Virus Vector as a Platform for Gene Therapy Delivery," Nature Reviews Drug Discovery, Feb. 1, 2019, vol. 18, pp. 358-378.

Wang P.L., et al., "Circular RNA is Expressed across the Eukaryotic Tree of Life," PLoS One, Mar. 7, 2014, vol. 9, No. 6, 10 pages.

Wang Y., et al., "Efficient Backsplicing Produces Translatable Circular mRNAs," RNA, Feb. 2015, vol. 21, No. 2, pp. 172-179.

Wesselhoeft R.A., et al., "Engineering Circular RNA for Potent and Stable Translation in Eukaryotic Cells," Nature Communications, Jul. 6, 2018, vol. 9, No. 2629, 10 pages.

Wesselhoeft R.A., et al., "RNA Circularization Diminishes Immunogenicity and Can Extend Translation Duration in Vivo," Molecular Cell, May 2, 2019, vol. 74, No. 3, pp. 508-520.

Yang L., et al., "Extracellular Vesicle-Mediated Delivery of Circular RNA SCMH1 Promotes Functional Recovery in Rodent and Non-human Primate Ischemic Stroke Models," Circulation, Aug. 11, 2020, vol. 142, No. 6, pp. 556-574.

Zhang X.O., et al., "Complementary Sequence-Mediated Exon Circularization," Cell, Sep. 25, 2014, vol. 159, No. 1, pp. 134-147.

Zhang Y., et al., "Circular Intronic Long Noncoding RNAs," Molecular Cell, Sep. 26, 2013, vol. 51, No. 6, pp. 792-806.

Zheng C., et al., "Evaluation of Promoters for Use in Tissue-Specific Gene Delivery," Methods in Molecular Biology, 2008, vol. 434, pp. 205-219.

International Search Report mailed on Aug. 6, 2021 for PCT/US21/25463 filed Apr. 1, 2021 (Applicant—Duke University) (4 pages).

Written Opinion mailed on Aug. 6, 2021 for PCT/US21/25463 filed Apr. 1, 2021 (Applicant—Duke University) (6 pages).

Saltzman J, et al. (2013) Cell-Type Specific Features of Circular RNA Expression. PLoS Genetics. 9(9):1-15.

* cited by examiner circ

*

Alu element (or complementary region)
Putative branch point
Poly-pyrimidine tract
Splice sites

356 nt     662 nt

O—[ FP | IRES | G ]—pA HIPK3

SEQ ID NO: 1

SEQ ID NO: 2

Alu element (or complementary region)
Putative branch point
Poly-pyrimidine tract
Splice sites

216 nt     332 nt

O—[ FP | IRES | G ]—pA Laccase2

SEQ ID NO: 6

SEQ ID NO: 7

Fig. 2C

Alu element (or complementary region)
Putative branch point
Poly-pyrimidine tract
Splice sites 82 nt    316 nt FP    IRES    G    pA    ZKSCAN1 agtgacagtggagattgtacagtttttcctcgatttgtcaggatttttttttgacggggttaacttcttgtctcccag
gtaggaagtgcagtggcgtaatctcggctcactacaacctcctggttcctgccttcctcgagcttccgag
tagctggaattacaggcgcctgccaccatgccctgactttgtattttttagtagagacggggtttcaccatgttggccagg
ctggtcttgaactcctgaccgattggccttgctctcggccttcccaaagtgctgagttacagggtgtgagccaccacccccc
ggcctcaggagcgttctgatagtgcctcgatgtgctgctcctctataaagtgttagcagcacagatcactttgtaaagtacg
tactaaatgacttttttttttatacttcag

SEQ ID NO: 11 gtaagaagcaggtttcatttagggggaggaaatgattcaggacggagagtctttgtgctgtgagtgatgaagagc
atgttagtcctggcaacgtagcgagcgagaccccatctctacaaaaaaattagccaggtagtggcgacacctgtgat
tccagctacgtgagtggaggtgctgagcaagacccctgggaggattgcttgagccaggaggttgagctgcagtgagctgtaatcatgccactact
ccaacctggcaacagacaagaccctgtctcaaagactacttgagtcagtctggcaggtctgcacgtctgcacacctgt
aatcccagcacttggaggctgaggcaggagattagctgaggttgagacggttgagagctgcaggtgcagtggtgaacct
tgtctcctactaaaatatagccaggtgtggtggcacattcgtagtagtccccaggtggttgagacggttgagagctgcaggtgaga
atacacttgaacccaggaggttgcagtgttgcagtgagctgagattaattaattaaaaaaaataagcatccccaaatatt
ttaaaaaaaaaaagaattaaaaaaagcatccccaaatatttgggaaaatacaacttacagccaatcccacagactgt
gttattctacattgtgtcattattaccaaatattgggaaaatacaacttacagccaatcccacagactacg
aaggcaaatgaactatgcgtaatgaacctggtaggcatta

SEQ ID NO: 12

Fig. 4A
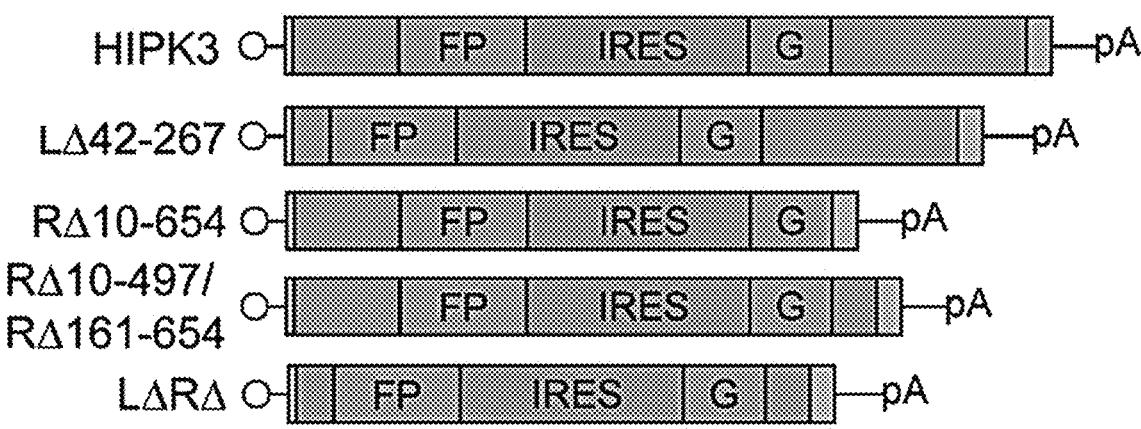
Fig. 4B
HIPK3 split GFP
Fig. 4C
LΔ42-267
Fig. 4D
RΔ10-654
Fig. 4E
RΔ10-497
Fig. 4F
RΔ161-654
Fig. 4G
LΔRΔ
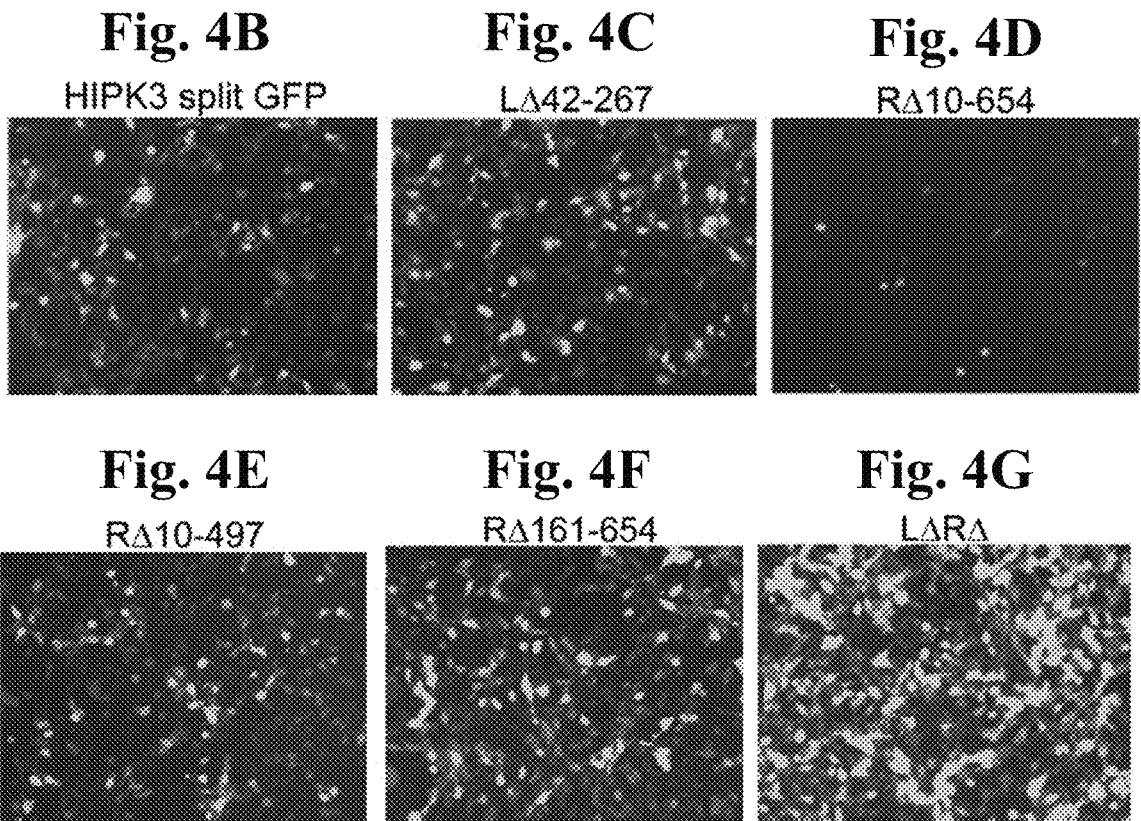

Fig. 4L
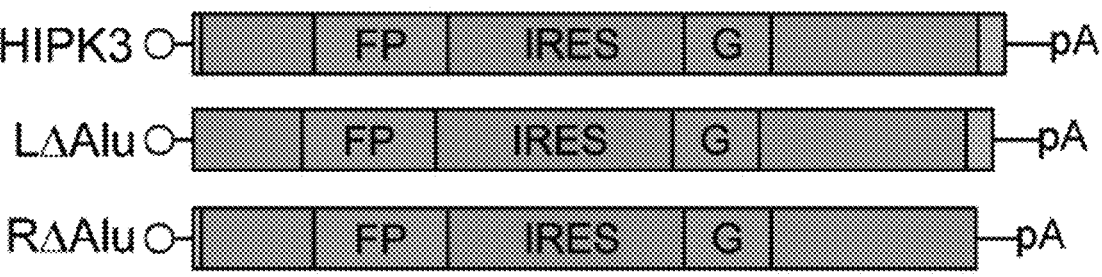
Fig. 4N
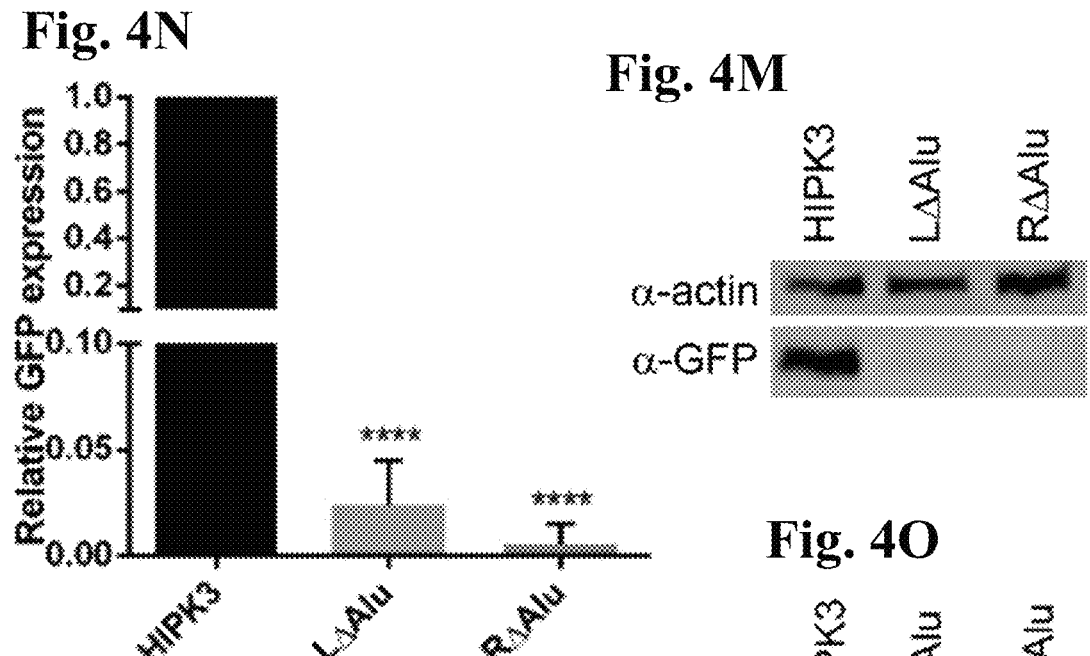
Fig. 4M
Fig. 4O
Fig. 4P
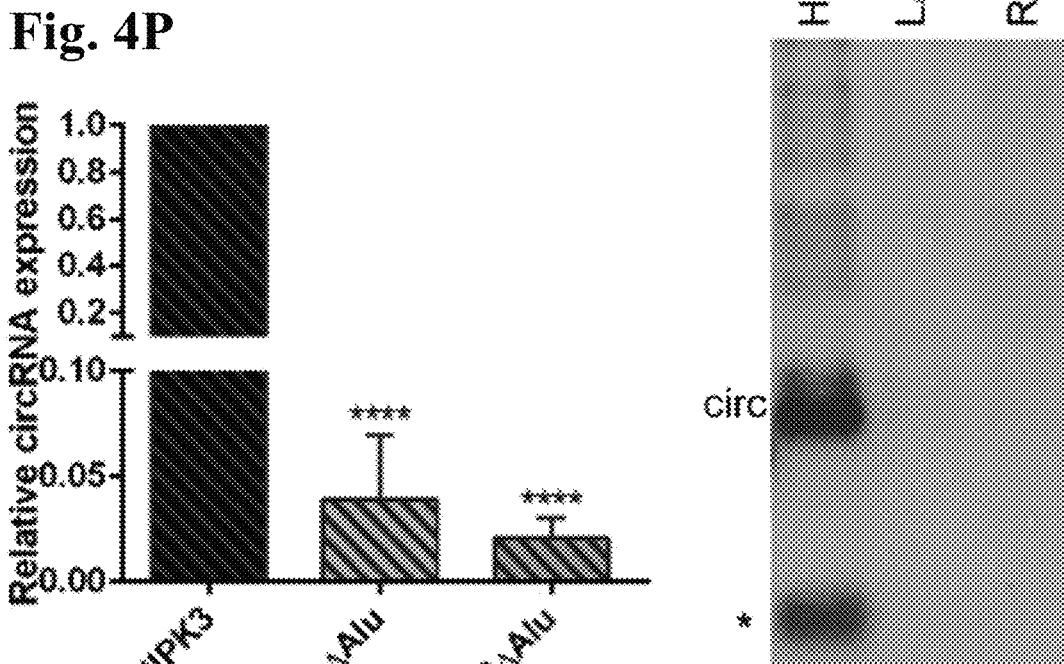

Fig. 5A
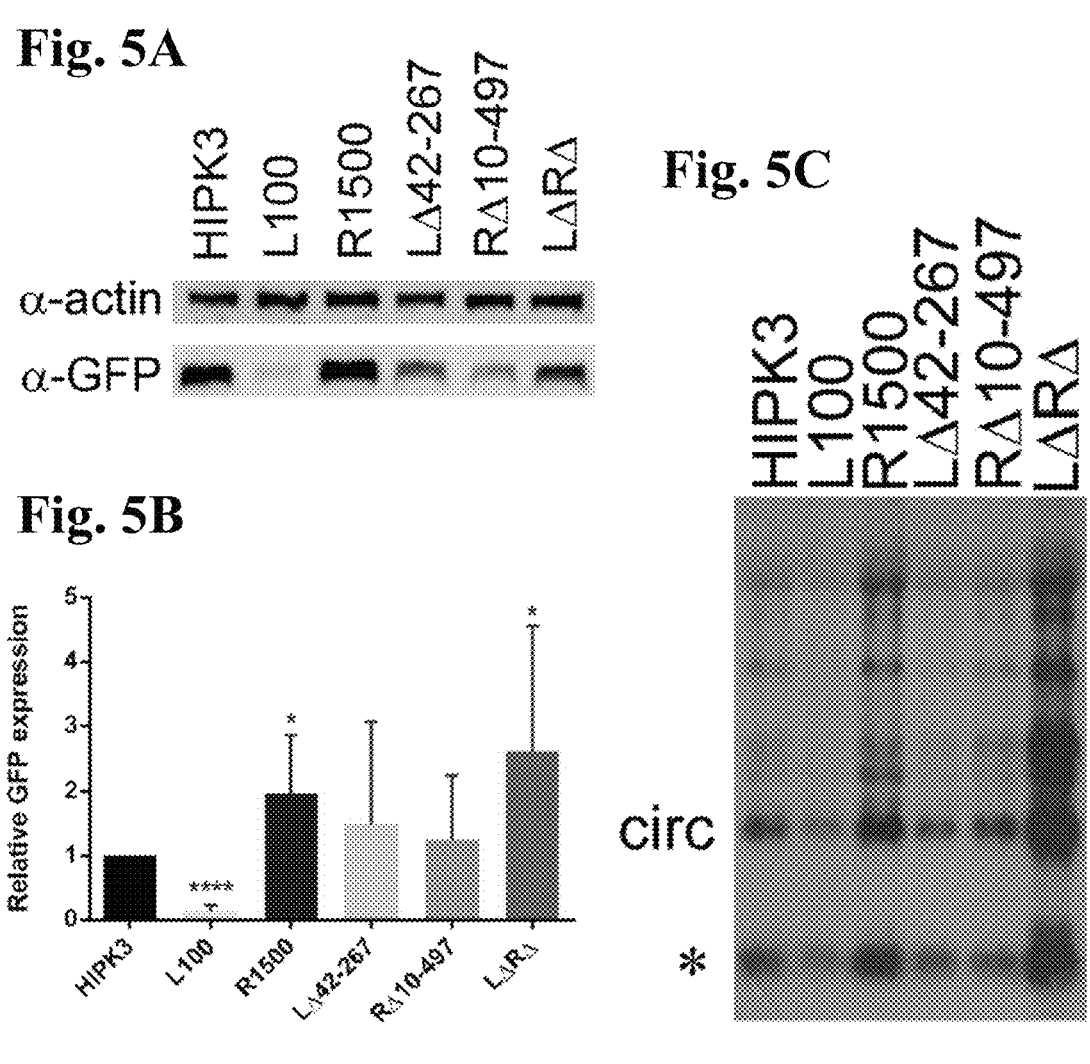
Fig. 5B
Fig. 5C
circ
*
Fig. 5D
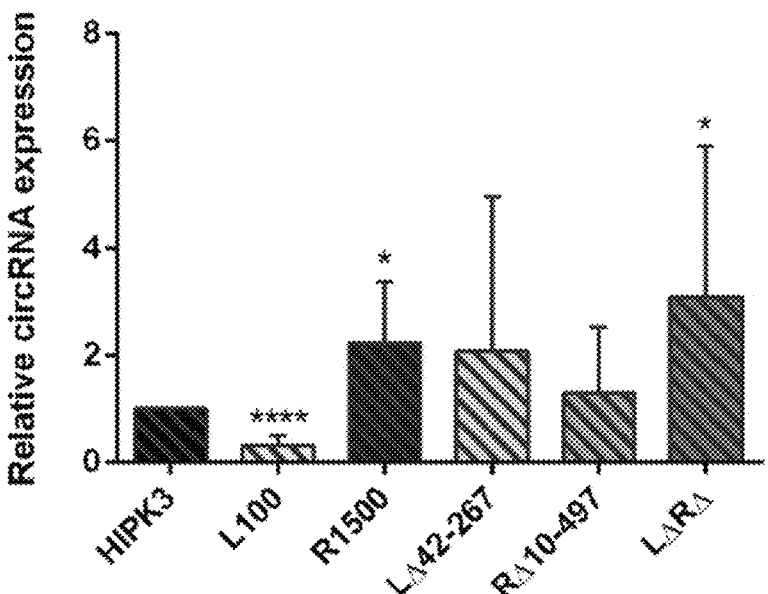

Fig. 5E
Fig. 5G
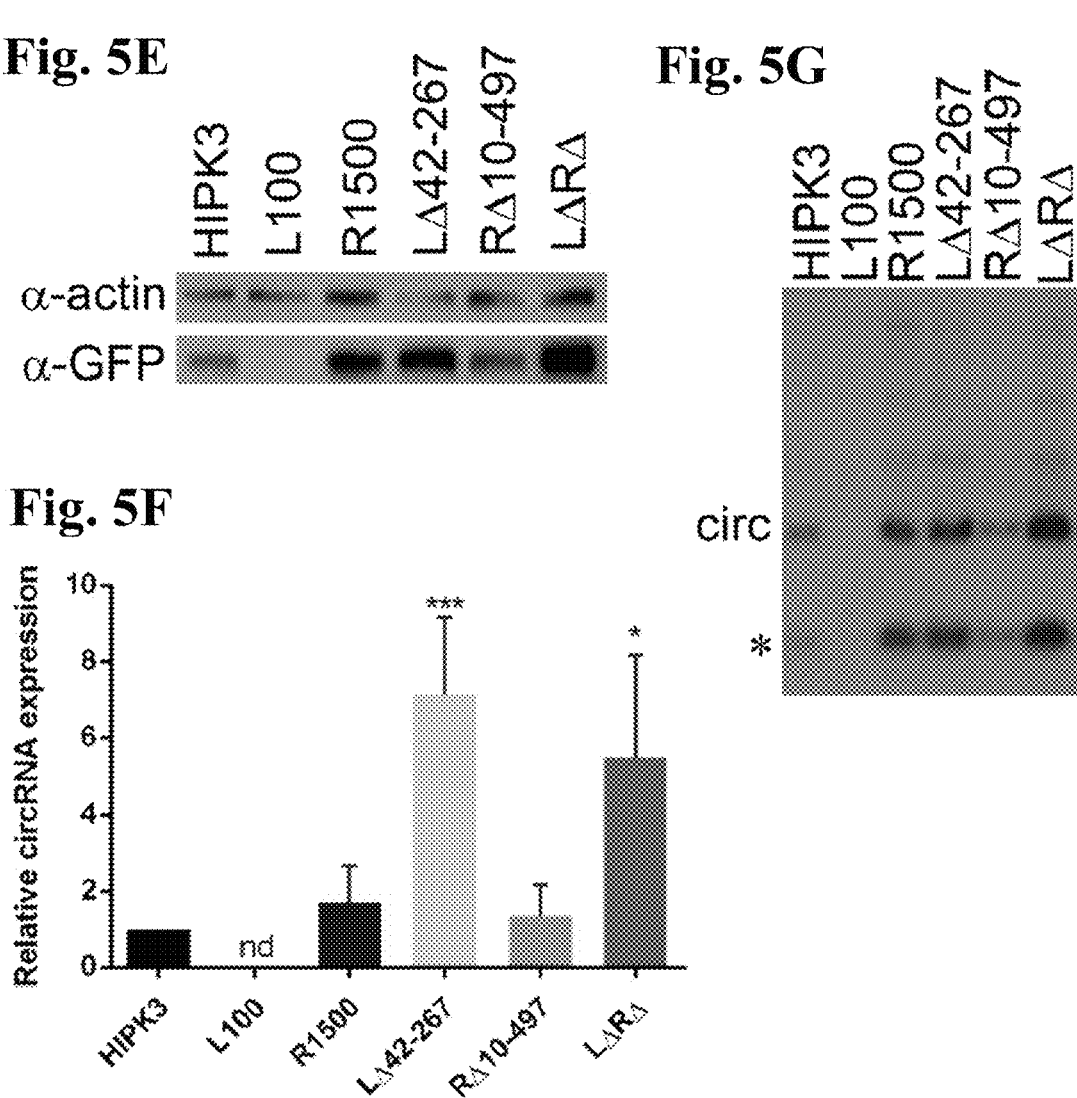
Fig. 5F
Fig. 5H
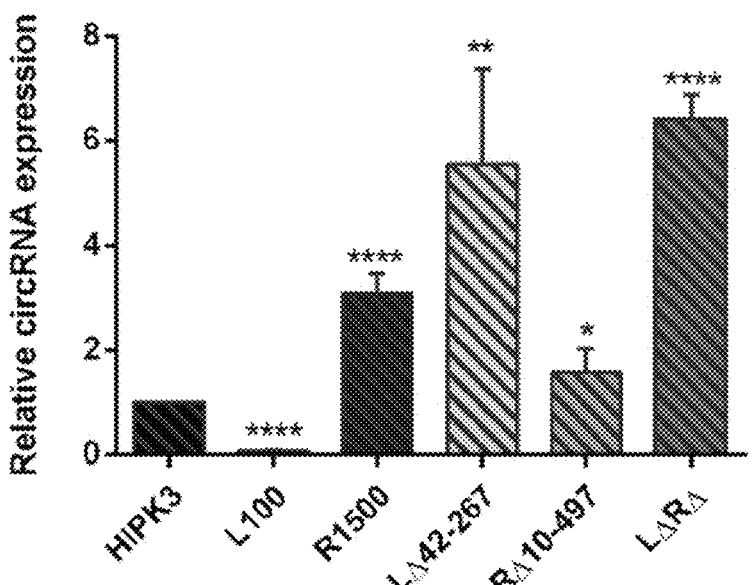

Fig. 6K
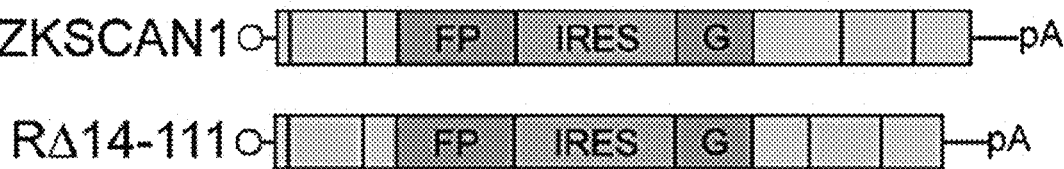
Fig. 6M
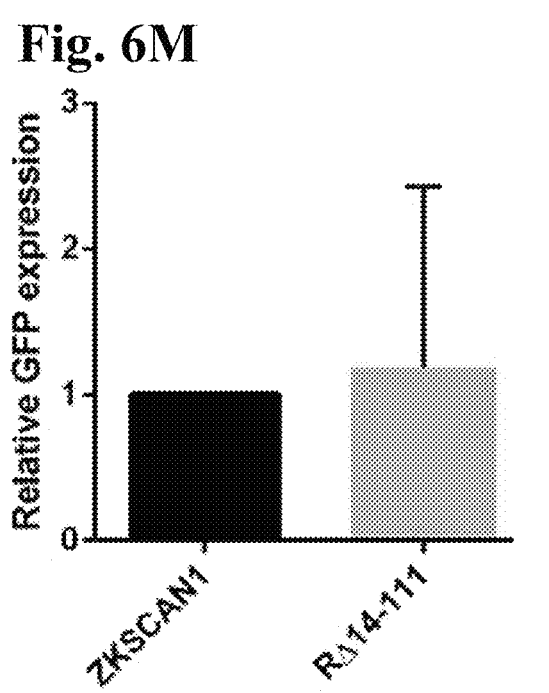
Fig. 6L
Fig. 6N
Fig. 6O
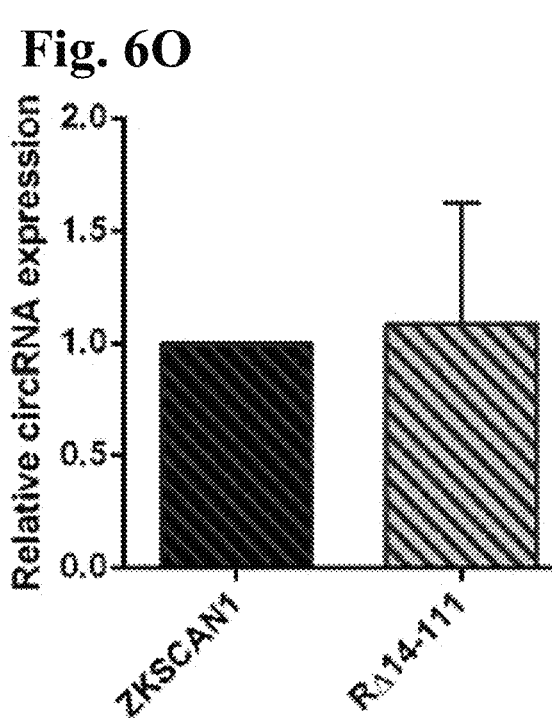
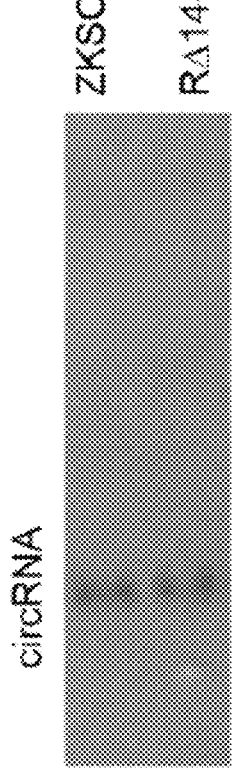

EMCV IRES

Poliovirus IRES

KSHV IRES

HCV IRES

Fig. 7H
HIPK3 EMCV
Fig. 7K
HIPK3 Polio
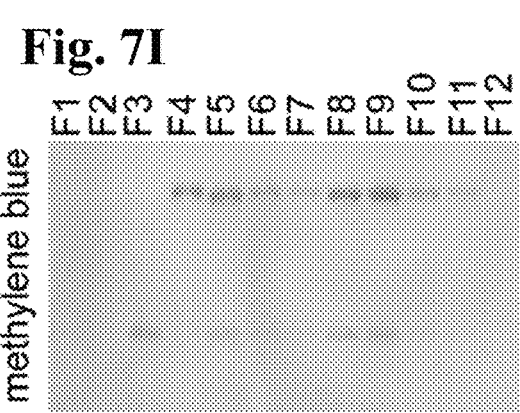
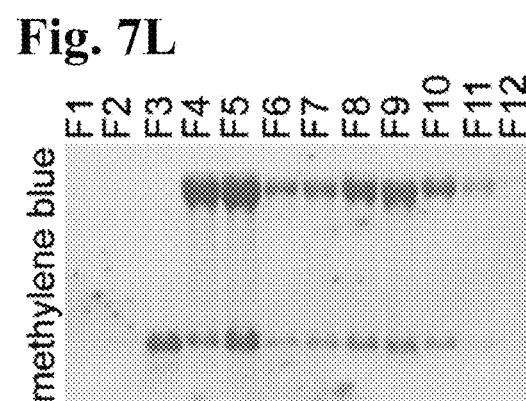
Fig. 7I
Fig. 7L
Fig. 7J
Fig. 7M
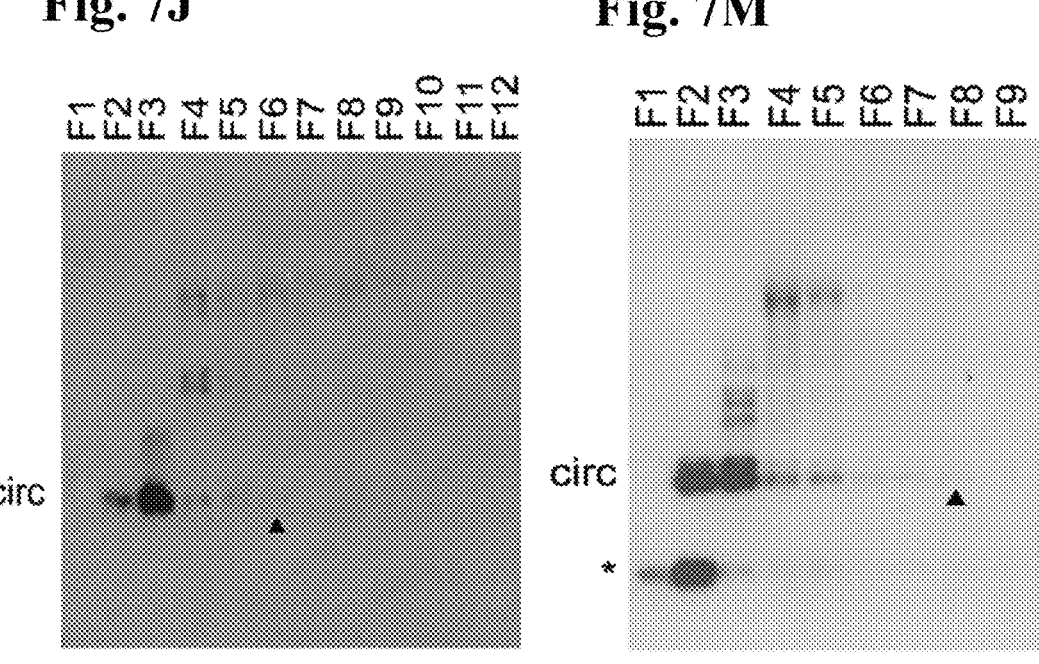

HIPK3 KSHV

Fig. 7Q
Fig. 7S
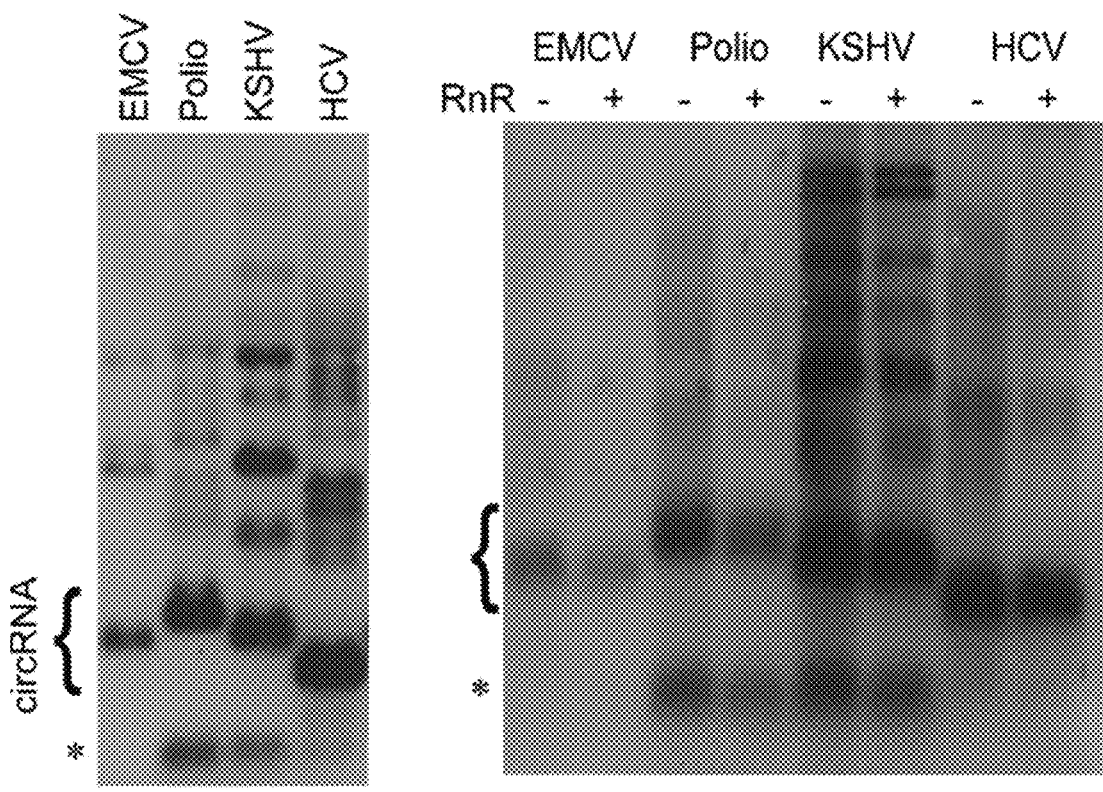
Fig. 7R
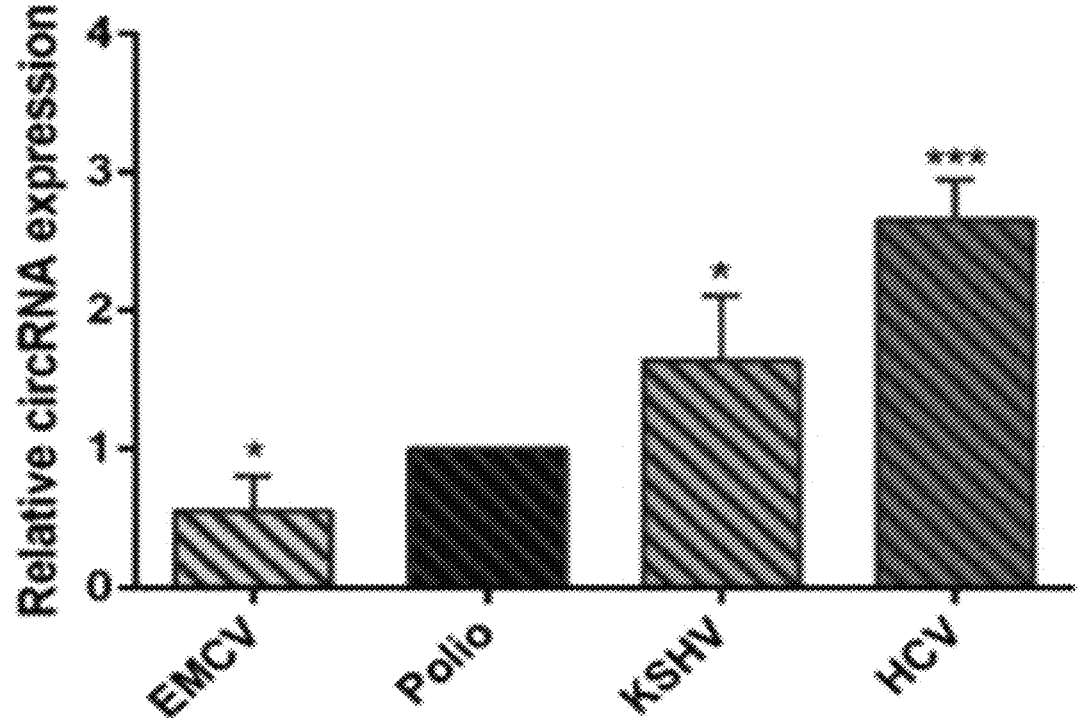

Fig. 8A
Fig. 8D
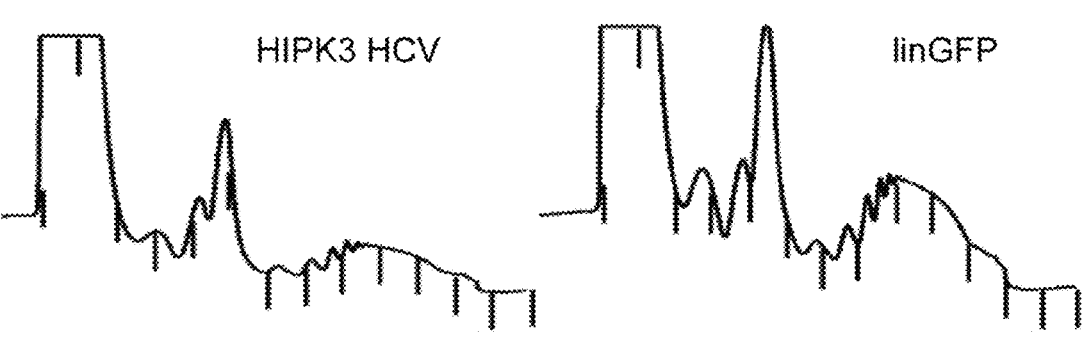
Fig. 8B
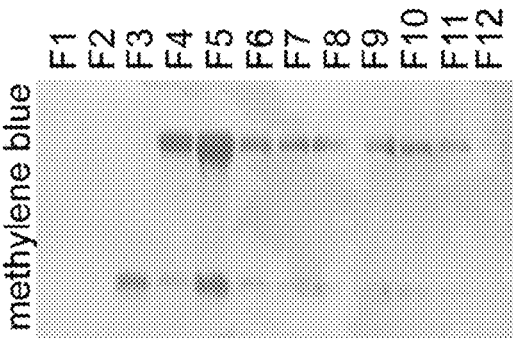
Fig. 8E
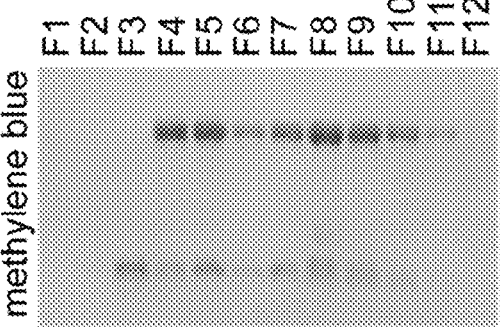
Fig. 8C
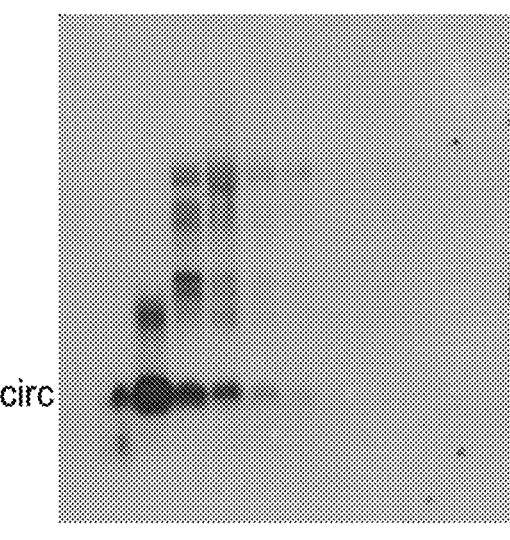
Fig. 8F
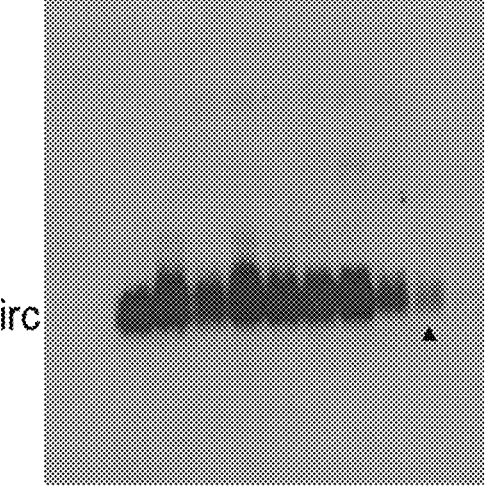

Fig. 10A
Fig. 10B
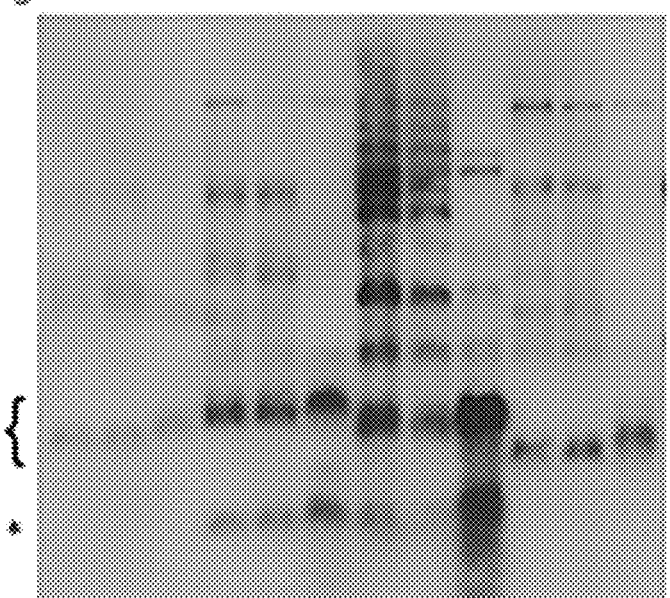
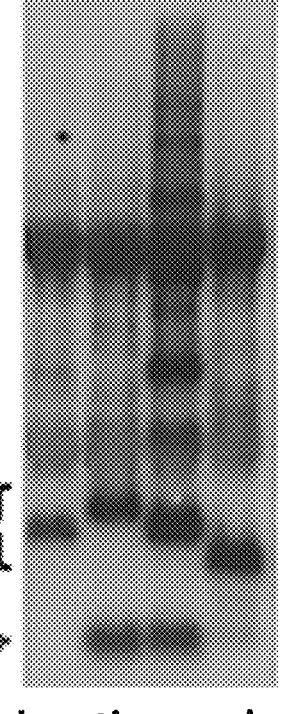
junction probe
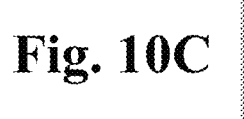
Polio     KSHV
Fig. 10C
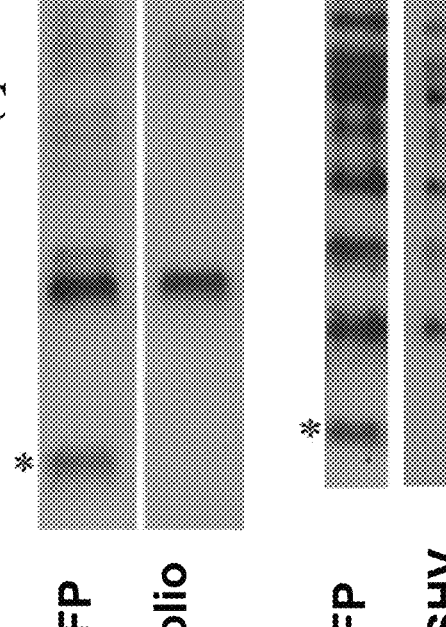
Fig. 10D
GFP   Polio     GFP   KSHV Fig. 10F                    Polio Polio*          KSHV KSHV*                    Fig. 10G

Fig. 11A
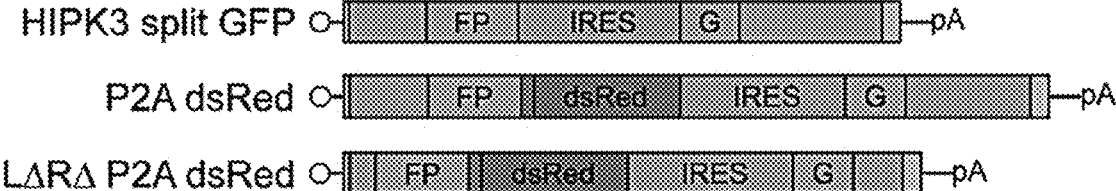
HIPK3 split GFP
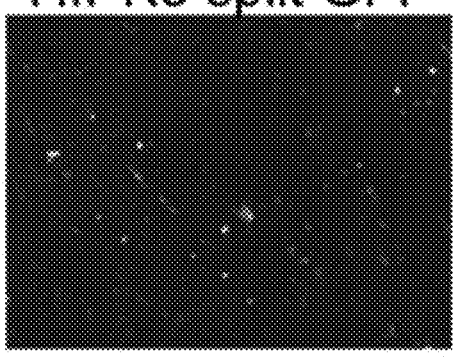
Fig. 11B
P2A dsRed
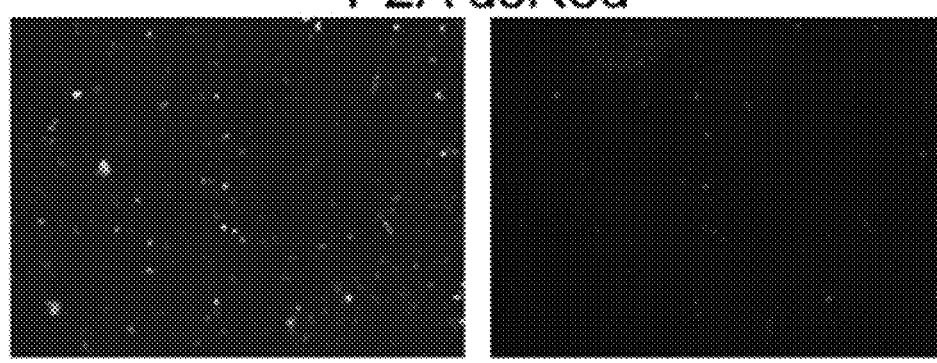
Fig. 11C          Fig. 11E
LΔRΔ P2A dsRed
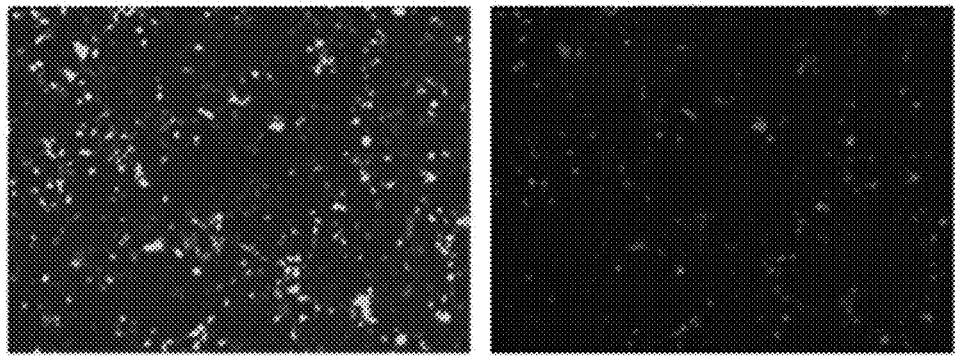
Fig. 11D          Fig. 11F HIPK3 Polio
P2A dsRed

Fig. 11M
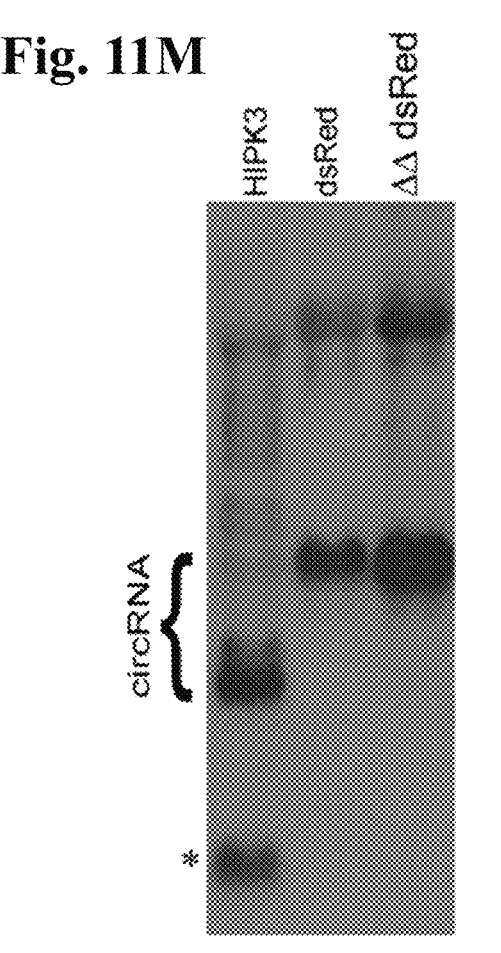
Fig. 11N
dsRed
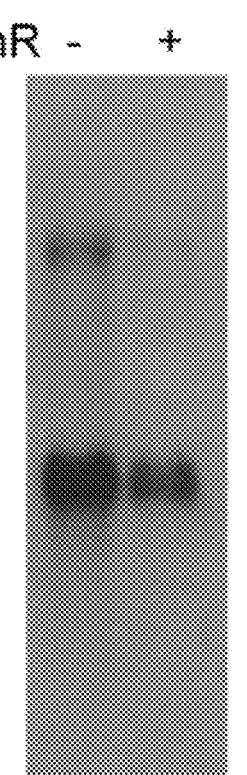
Fig. 11O
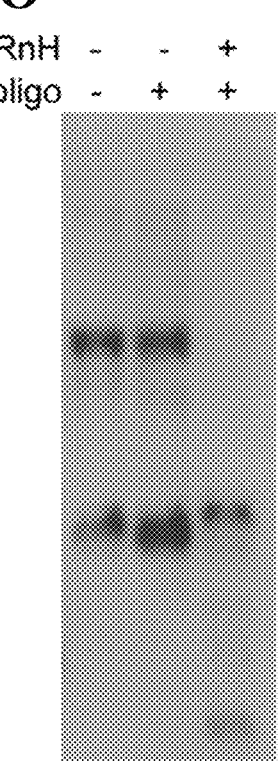
Fig. 11P no primary                    HIPK3 Polio                    HIPK3 Polio ΔΔ

Fig. 12E          Fig. 12F          Fig. 12G heart muscle

Fig. 12I      Fig. 12J      Fig. 12K

COMPOSITIONS AND METHODS FOR CIRCULAR RNA EXPRESSION

CROSS REFERENCE TO RELATED APPLICATIONS

This application is a national phase application of International Application No. PCT/US2021/025463 filed Apr. 1, 2021, which claims priority to U.S. Provisional Patent Application Ser. No. 62/969,758, filed Feb. 4, 2020, the contents of each of which is hereby incorporated by reference in its entirety.

FEDERAL FUNDING LEGEND

This invention was made with Government support under Federal Grant No. R01NS099371 awarded by the National Institutes of Health. The Federal Government has certain rights to this invention.

INCORPORATION BY REFERENCE OF SEQUENCE LISTING PROVIDED ELECTRONICALLY

This application contains a Substitute Sequence Listing provided as a txt electronic file titled "21_2000_WO_US_SUBSTITUTE_SEQUENCE_LISTING". The Substitute Sequence Listing, having a size of 24,576 bytes, created on 6 Oct. 2025 and submitted on 6 Oct. 2025, replaces the txt electronic version of the Sequence Listing titled "21_2000_WO_Sequence_Listing_ST25" having a size of 36,864 bytes filed on 1 Apr. 2021. The Substitute Sequence Listing is hereby incorporated by reference in its entirety pursuant to 37 C.F.R. § 1.52(e)(5).

BACKGROUND OF THE INVENTION

RNA modulation has become a promising therapeutic approach for the treatment of several types of disease. Circular RNAs (circRNAs) are highly stable RNA molecules that are attractive templates for expression of therapeutic proteins and non-coding RNAs. circRNAs introduce an additional level of control, modulating, either directly or indirectly, a variety of cellular functions and pathways. Growing evidence shows that circRNAs play an important role in neurological disorders, atherosclerotic vascular disease, and cancer. For at least these reasons, in addition to the long life span of circRNAs and resistance to RNA decay mechanisms, there is a growing interest in developing circRNA-based therapeutics.

Currently, the design of synthetic circRNA for therapeutic use is lacking. The present disclosure provides for rational design of synthetic circRNA cassettes, including compositions for encoding for at least two circular RNA (circRNAs), which can be packaged into recombinant AAV vectors for therapeutic delivery.

BRIEF SUMMARY OF THE DISCLOSURE

The present disclosure provides, in part, nucleic acid molecules encoding for at least two circular RNA (circRNAs), adeno-associated virus (AAV) particles including nucleic acid molecules encoding for at least two circRNAs, pharmaceutical compositions, and methods for delivering such to a subject.

One aspect of the disclosure provides for a nucleic acid molecule encoding for at least two circular RNA (circR- NAs). In some embodiments, compositions herein may comprise a nucleic acid molecule encoding for at least two circular RNA (circRNAs), wherein the nucleic acid molecule further comprises: (i) a first circRNA having a first circRNA-encoding sequence of interest, (ii) a second circRNA having a second circRNA-encoding sequence of interest, wherein the second circRNA is in tandem to the first circRNA-encoding sequence of interest in the first circRNA, wherein the first circRNA-encoding sequence of interest and the second circRNA in tandem are flanked by intronic elements. In some embodiments, a first circRNA disclosed herein can further have an internal ribosome entry site (IRES), a promoter region in the 5' untranslated region (UTR) and outside of the intronic elements that flank the first circRNA-encoding sequence of interest and the second circRNA in tandem, a translation regulating region in the 3' UTR and outside of the intronic elements that flank the first circRNA-encoding sequence of interest and the second circRNA in tandem, or any combination thereof. In some embodiments, compositions herein can have the intronic elements flanking the first circRNA-encoding sequence of interest and the second circRNA in tandem are backspliced yield the at least two circRNAs without forming a scar at a site wherein the circRNAs are covalently closed.

In some embodiments, the disclosure provides for adeno-associated virus (AAV) genomes having any one of the nucleic acid molecules encoding for at least two circRNAs as disclosed herein.

Another aspect of the disclosure provides for adeno-associated virus (AAV) particles. In some embodiments, AAV particles disclosed herein comprise at least one AAV genomic cassette, the at least one AAV genomic cassette having a nucleic acid molecule encoding for at least one circular RNA (circRNA), at least one circRNA encompassing an internal ribosome entry site (IRES) element preceding an open reading frame (ORF) in a backsplicing cassette, wherein the backsplicing cassette comprises at least one circRNA-encoding sequence of interest. In some embodiments, AAV particles herein can further include an intron pair flanking the at least one circRNA-encoding sequence of interest, wherein the intron pair flanking the at least one circRNA-encoding sequence of interest comprises a deletion of about 750 nucleotides. In some embodiments, AAV particles herein can further include an intron pair flanking the at least one circRNA-encoding sequence of interest, wherein the intron pair flanking the at least one circRNA-encoding sequence of interest comprises a left intron comprising a deletion of about 250 nucleotides and a right intron comprising a deletion of about 500 nucleotides.

In some embodiments, the present disclosure provides for methods of delivering a circRNA-encoding sequence of interest to a cell, the method including introducing the cell to any of the compositions or AAV particles disclosed herein. In some embodiments, the present disclosure provides for methods of delivering a circRNA-encoding sequence of interest to a tissue, the method including introducing the tissue to any of the compositions or AAV particles disclosed herein.

In some embodiments, the present disclosure provides for methods of treating a disease or condition in a subject. In some embodiments, the methods of treating a disease or condition in a subject herein include administering an effective amount of any of the compositions or AAV particles disclosed herein to a subject, wherein the effective amount is an amount that reduces at least one symptom of disease or condition in the subject.

In some embodiments, methods herein comprise expressing at least one circular RNA (circRNA) in a tissue by administering any of the compositions or AAV particles disclosed herein to the tissue, wherein expression of the at least one circRNA can be substantially increased as compared to baseline. In some aspects, expression of the at least one circRNA is increased at least 2-fold compared to baseline. In some other aspects, expression of the at least one circRNA is increased by at least 4-fold compared to baseline when the at least one AAV particle is delivered to a heart tissue, a liver tissue, a skeletal muscle tissue, or any combination thereof. In some other aspects, expression of the at least one circRNA is increased by at least 50-fold compared to baseline when the at least one AAV particle is delivered to a skeletal muscle tissue.

In some embodiments, any of the compositions or AAV particles disclosed herein can be administered by intramuscular injection, intravenous injection, intracoronary injection, intraarterial injection, or any combination thereof.

An aspect of the disclosure provides for kits, wherein a kit can comprise any of the compositions or AAV particles disclosed herein disclosed herein and at least one container.

BRIEF DESCRIPTION OF THE DRAWINGS

The patent or application file contains at least one drawing executed in color. Copies of this patent or patent application publication with color drawings will be provided by the Office upon request and payment of the necessary fee.

The following drawings form part of the present specification and are included to further demonstrate certain aspects of the present disclosure, which can be better understood by reference to the drawings in combination with the detailed description of specific embodiments presented herein.

FIGS. 1A-1Q are schematics, images, and graphs showing the distance requirements between Alu elements and splice sites differed in upstream and downstream introns in accordance with embodiments of the present disclosure. FIG. 1A shows a schematic of a reporter that was constructed by extracting portions of introns from the HIPK3 gene and placing them around a split GFP reporter exon. Inverted Alu repeats in the introns interacted, allowing for backsplicing to occur, forming a circRNA. The presence of an IRES sequence drove translation, leading to GFP protein expression. FIG. 1B shows a schematic of constructs having a sequence ranging from 100 nt to 1,500 nt inserted into the left HIPK3 intron at the indicated position. FIGS. 1C and 1D depict a western blot analysis for GFP expression where FIG. 1C shows a representative image of a blot and FIG. 1D shows a graph of the quantification of the blot with actin as a loading control. FIGS. 1E and 1F depict a northern blot analysis probing for GFP RNA where FIG. 1E shows a representative image of a blot and FIG. 1F shows a graph of the quantification of the blot. FIG. 1G shows a schematic of constructs having sequences ranging from 100 nt to 1,500 nt inserted into the right HIPK3 intron at the indicated position. FIGS. 1H and 1I depict a western blot analysis for GFP expression where FIG. 1H shows a representative image of a blot and FIG. 1I shows a graph of the quantification of the blot with actin as a loading control. FIGS. 1J and 1K depict a northern blot analysis probing for GFP RNA where FIG. 1J shows a representative image of a blot and FIG. 1K shows a graph of the quantification of the blot. FIGS. 1L-1Q are schematics, images, and graphs showing formation of a tricRNA when tricRNA was inserted into the right HIPK3 intron. FIG. 1L shows a schematic of a construct having sequences driving formation of a circular tricRNA containing Broccoli (tricY-Broccoli) inserted into the same location in the right HIPK3 intron. FIG. 1M depicts a representative image of a gel showing verification of tricY-Broccoli expression by gel electrophoresis followed by DFHBI-1T staining. FIGS. 1N and 1O depict a western blot analysis for GFP expression where FIG. 1N shows a representative image of a blot and FIG. 1O shows a graph of the quantification of the blot with actin as a loading control. FIGS. 1P and 1Q depict a northern blot analysis probing for GFP RNA where FIG. 1P shows a representative image of a blot and FIG. 1Q shows a graph of the quantification of the blot.

FIGS. 2A-2C are schematics showing sequence information for HIPK3 (SEQ ID NO: 1 and SEQ ID NO: 2) (FIG. 2A), Laccase2 (SEQ ID NO: 6 and SEQ ID NO: 7) (FIG. 2B), and ZKSCAN1 (SEQ ID NO: 11 and SEQ ID NO: 12) (FIG. 2C) intron pairs in accordance with embodiments of the present disclosure. Distances between the complementary region and splice sites are noted on top of the schematic and complementary regions and splice site information are overlaid on the sequences.

FIG. 3A shows a schematic of constructs having sequences ranging from 100 nt to 1500 nt inserted into the left HIPK3 intron at a site distal to the splice site. FIGS. 3B and 3C depict a western blot analysis for GFP expression where FIG. 3B shows a representative image of a blot and FIG. 3C shows a graph of the quantification of the blot with actin as a loading control. FIGS. 3D and 3E depict a northern blot analysis probing for GFP sequences where FIG. 3D shows a representative image of a blot and FIG. 3E shows a graph of the quantification of the blot.

FIGS. 4A-4P are schematics, images, and graphs showing partial truncation of intronic sequences increased circRNA expression in accordance with embodiments of the present disclosure. FIG. 4A shows a schematic of constructs having portions of the HIPK3 left and right introns deleted where deletions are numbered from the start of their respective intron. FIGS. 4B-4G show representative images of GFP fluorescence in HEK293 cells four days after transfection with the following constructs: HIPK3 split GFP (FIG. 4B); LA42-267 (FIG. 4C); RΔ10-654 (FIG. 4D); RΔ10-497 (FIG. 4E); RΔ161-654 (FIG. 4F); and LARA (FIG. 4G). FIG. 4H shows a representative image of a blot and FIG. 4I shows a graph of the quantification of the blot with actin as a loading control. FIG. 4J shows a representative image of a blot and FIG. 4K shows a graph of the quantification of the blot. FIG. 4L shows a schematic of constructs having either the left or right partial Alu element deleted from the HIPK3 introns. FIGS. 4M and 4N depict a western blot analysis for GFP expression where FIG. 4M shows a representative image of a blot and FIG. 4N shows a graph of the quantification of the blot with actin as a loading control. FIGS. 4O and 4P depict a northern blot analysis probing for GFP RNA where FIG. 4O shows a representative image of a blot and FIG. 4P shows a graph of the quantification of the blot.

FIGS. 5A-5H are schematics, images, and graphs showing that the effects of insertions and deletions were conserved in glioblastoma and hepatocarcinoma cell lines in accordance with embodiments of the present disclosure. FIGS. 5A-5D show GFP expression in U87 glioblastoma cells transfected with the indicated constructs. FIGS. 5A and 5B depict a western blot analysis for GFP expression where FIG. 5A shows a representative image of a blot and FIG. 5B shows a graph of the quantification of the blot with actin as a loading control. FIGS. 5C and 5D depict a northern blot analysis probing for GFP RNA where FIG. 5C shows a representative image of a blot and FIG. 5D shows a graph of the quantification of the blot. FIGS. 5E-5H show GFP expression in Huh7 hepatocarcinoma cells transfected with the indicated constructs. FIGS. 5E and 5F depict a western blot analysis for GFP expression where FIG. 5E shows a representative image of a blot and FIG. 5F shows a graph of the quantification of the blot with actin as a loading control. FIGS. 5G and 5H depict a northern blot analysis probing for GFP RNA where FIG. 5G shows a representative image of a blot and FIG. 5H shows a graph of the quantification of the blot.

FIGS. 6A-6T are schematics, images, and graphs showing that intronic spacing effects on circRNA formation were conserved in Laccase2 and ZKSCAN1 intron pairs in accordance with embodiments of the present disclosure. FIGS. 6A-6E show GFP expression in HEK293 cells transfected with constructs containing ZKSCAN1 intron pairs with randomized sequence insertions as indicated. FIG. 6A shows a schematic of the ZKSCAN1 constructs with location of sequence insertions. FIGS. 6B and 6C depict a western blot analysis for GFP expression where FIG. 6B shows a representative image of a blot and FIG. 6C shows a graph of the quantification of the blot with actin as a loading control. FIGS. 6D and 6E depict a northern blot analysis probing for GFP RNA where FIG. 6D shows a representative image of a blot and FIG. 6E shows a graph of the quantification of the blot. FIG. 6F shows a schematic of the Laccase2 constructs with location of sequence insertions. FIGS. 6G and 6H depict a western blot analysis for GFP expression where FIG. 6G shows a representative image of a blot and FIG. 6H shows a graph of the quantification of the blot with actin as a loading control. FIGS. 6I and 6J depict a northern blot analysis probing for GFP RNA where FIG. 6I shows a representative image of a blot and FIG. 6J shows a graph of the quantification of the blot. FIGS. 6K-6O show GFP expression in HEK293 cells transfected with constructs containing ZKSCAN1 intron pairs with sequence deletions as indicated. FIG. 6K shows a schematic of the ZKSCAN1 constructs with location of sequence deletions. FIGS. 6L and 6M depict a western blot analysis for GFP expression where FIG. 6L shows a representative image of a blot and FIG. 6M shows a graph of the quantification of the blot with actin as a loading control. FIGS. 6N and 6O depict a northern blot analysis probing for GFP RNA where FIG. 6N shows a representative image of a blot and FIG. 6O shows a graph of the quantification of the blot. FIGS. 6P-6T show GFP expression in HEK293 cells transfected with constructs containing Laccase2 intron pairs with sequence deletions as indicated. FIG. 6P shows a schematic of the Laccase2 constructs with location of sequence deletions. FIGS. 6Q and 6R depict a western blot analysis for GFP expression where FIG. 6Q shows a representative image of a blot and FIG. 6R shows a graph of the quantification of the blot with actin as a loading control.

FIGS. 6S and 6T depict a northern blot analysis probing for GFP RNA where FIG. 6S shows a representative image of a blot and FIG. 6T shows a graph of the quantification of the blot.

FIGS. 7A-7R are schematics, images, and graphs showing IRES elements affected translation efficiency and circRNA expression levels in accordance with embodiments of the present disclosure. FIG. 7A shows a schematic of HIPK3 split GFP constructs created with either the EMCV, Polio, KSHV vFLIP, or HCV IRES elements. FIG. 7F shows a representative image of a blot and FIG. 7G shows a graph of the quantification of the blot with actin as a loading control. FIGS. 7H-7P show constructs as indicated transfected into HEK293 cells and harvested in cycloheximide followed by a sucrose gradient and fractionation where the arrowhead marks the last fraction in which the circRNA was detected. FIGS. 7H-7J show representative images of an OD254 trace of a gradient having the HIPK3 EMCV construct, with fractions marked by lines (FIG. 7H); RNA that was extracted from gradients, separated by gel electrophoresis, transferred to a membrane, and stained with methylene blue to visualize the ribosomal RNA (FIG. 7I); and the same membrane shown in FIG. 7I probed for GFP RNA (FIG. 7J). FIGS. 7K-7M show representative images of an OD254 trace of a gradient having the HIPK3 Polio construct, with fractions marked by lines (FIG. 7K); RNA that was extracted from gradients, separated by gel electrophoresis, transferred to a membrane, and stained with methylene blue to visualize the ribosomal RNA (FIG. 7L); and the same membrane shown in FIG. 7L probed for GFP RNA (FIG. 7M). FIGS. 7N-7P show representative images of an OD254 trace of a gradient having the HIPK3 KSHV construct, with fractions marked by lines (FIG. 7N); RNA that was extracted from gradients, separated by gel electrophoresis, transferred to a membrane, and stained with methylene blue to visualize the ribosomal RNA (FIG. 7O); and the same membrane shown in FIG. 7O probed for GFP RNA (FIG. 7P). FIGS. 7Q and 7R depict a northern blot analysis probing for GFP sequences where FIG. 7Q shows a representative image of a blot and FIG. 7R shows a graph of the quantification of the blot. FIG. 7S shows a representative northern blot, probing for GFP RNA within the RNA that was isolated from the indicated constructs which were (+) or were not (−) digested by RNase R (RnR).

FIGS. 8A-8F are schematics, images, and graphs showing translation efficiency with the HCV IRES and a control linear RNA in accordance with embodiments of the present disclosure. FIGS. 8A-8C show representative images of an OD254 trace of a gradient having the HIPK3 HCV construct, with fractions marked by lines (FIG. 8A); RNA that was extracted from gradients, separated by gel electrophoresis, transferred to a membrane, and stained with methylene blue to visualize the ribosomal RNA (FIG. 8B); and the same membrane shown in FIG. 8B probed for GFP RNA (FIG. 8C). FIGS. 8D-8F show representative images of an OD254 trace of a gradient having cap-driven linear GFP mRNA (linGFP), with fractions marked by lines (FIG. 8D); RNA that was extracted from gradients, separated by gel electrophoresis, transferred to a membrane, and stained with methylene blue to visualize the ribosomal RNA (FIG. 8E); and the same membrane shown in FIG. 8E probed for GFP RNA (FIG. 8F).

FIGS. 9A-9D show GFP expression in U87 glioblastoma cells transfected with the indicated constructs. FIGS. 9A and 9B depict a western blot analysis for GFP expression where FIG. 9A shows a representative image of a blot and FIG. 9B shows a graph of the quantification of the blot with actin as a loading control. FIGS. 9C and 9D depict a northern blot analysis probing for GFP RNA where FIG. 9C shows a representative image of a blot and FIG. 9D shows a graph of the quantification of the blot. FIGS. 9E-9H show GFP expression in Huh7 hepatocarcinoma cells transfected with the indicated constructs. FIGS. 9E and 9F depict a western blot analysis for GFP expression where FIG. 9E shows a representative image of a blot and FIG. 9F shows a graph of the quantification of the blot with actin as a loading control. FIGS. 9G and 9H depict a northern blot analysis probing for GFP RNA where FIG. 9G shows a representative image of a blot and FIG. 9H shows a graph of the quantification of the blot.

FIGS. 10A-10G are schematics, images, and graphs showing IRES elements affected splicing and impact formation of additional RNA species in accordance with embodiments of the present disclosure. FIG. 10A shows a representative image of RNase H digestion performed with an oligonucleotide targeting the back-splice junction where samples were analyzed by northern blot and probed against GFP RNA. FIG. 10B shows a representative image of RNA from the indicated constructs analyzed by Northern blot and probed with an oligonucleotide spanning the back-splice junction. FIGS. 10C and 10D show a representative images of RNA from HIPK3 polio construct (FIG. 10C) and HIPK3 KSHV construct (FIG. 10D) analyzed by northern blot and probed for GFP and the specific IRES sequences. FIG. 10E shows a representative image of a virtual northern blot and RT-PCR with primers spanning either the back-splice junction (top) (SEQ ID NO:46) or the IRES sequence (middle, Poliovirus IRES (SEQ ID NO:47); bottom, KSHV vFLIP IRES (SEQ ID NO:48)) confirming the presence of both the back-splice and a linear splice in the small circRNA band. FIGS. 10F and 10G show representative images of mutations to the splice donor site as identified in FIG. 10E in the HIPK3 polio construct (FIG. 10F) and HIPK3 KSHV construct (FIG. 10G), which modified splicing to remove the small circRNA band, as analyzed by northern blotting, probing for GFP where, on all northern blots, the * refers to the small circular species.

FIGS. 11A-11P are schematics, images, and graphs showing circRNA size could be increased without loss of expression in accordance with embodiments of the present disclosure. FIG. 11A shows a schematic of constructs having a self-cleaving P2A peptide followed by the dsRed ORF added to the exon at the end of the GFP fragment either in the original HIPK3 construct or in the LΔRΔ intron pair. FIGS. 11B-11D show representative images of GFP fluorescence in HEK293 cells four days after transfection with the following constructs: HIPK3 split GFP (FIG. 11B); PP2A dsRed (FIG. 11C); and LΔRΔ PP2A dsRed (FIG. 11D). FIGS. 11E-11F show representative images of red fluorescence in HEK293 four days after transfection with the following constructs: PP2A dsRed (FIG. 11E) and LΔRΔ PP2A dsRed (FIG. 11F). FIG. 11G shows a representative image of a blot and FIG. 11H shows a graph of the quantification of the blot with actin as a loading control. FIG. 11J shows a OD254 trace of the gradient, with fractions marked by lines; FIG. 11K shows RNA was extracted from gradients, separated by gel electrophoresis, transferred to a membrane, and stained with methylene blue to visualize the ribosomal RNA; and FIG. 11L shows the same membrane from FIG. 11K probed for GFP RNA (the arrowhead marks the last fraction in which the circRNA was detected). FIGS. 11M and 11I depict a northern blot analysis probing for GFP RNA where FIG. 11M shows a representative image of a blot and FIG. 11I shows a graph of the quantification of the blot. FIG. 11N depicts RNA treated with RNase R, then analyzed by northern blot, probing for GFP RNA. FIG. 11O depicts RNase H (RnH) digestion performed with an oligonucleotide targeting the backsplice junction where samples were analyzed by northern blot and probed against GFP RNA. FIG. 11P depicts RNA analyzed by northern blot and probed with an oligonucleotide spanning the backsplice junction.

FIGS. 12A-12L are schematics, images, and graphs showing the LΔRΔ intron pair increased circRNA expression in multiple murine tissues in vivo in accordance with embodiments of the present disclosure. FIG. 12A shows a schematic of constructs packaged into recombinant AAV9 vectors and injected intravenously into C57BL/6 mice. FIG. 12B shows AAV vector genomes per cell that were quantified in each tissue by quantitative PCR (qPCR) for the CMV promoter, normalized to the mouse lamin B2 locus. FIGS. 12C and 12D show results from quantitative RT-PCR performed with primers amplifying GFP across the backsplice junction revealed increased circRNA expression with the LΔRΔ intron pair. circRNA expression is graphed relative to GAPDH (FIG. 12C) or normalized to HIPK3 Polio expression in each tissue (FIG. 12D). FIGS. 12E-12G show immunofluorescent staining of sectioned cardiac tissue for GFP expression in tissues harvested from mice injected with HIPK3 Polio (FIG. 12F) and HIPK3 Polio ΔΔ (FIG. 12G) where FIG. 12E was not stained with primary antibody. FIG. 12H shows a graph depicting the level of GFP expression in cardiac tissue harvested from mice injected with HIPK3 Polio or HIPK3 Polio ΔΔ quantified by the corrected total cell fluorescence (CTCF) method. FIGS. 12I-12K show immunofluorescent staining of sectioned skeletal muscle tissue for GFP expression in tissues harvested from mice injected with HIPK3 Polio (FIG. 12J) and HIPK3 Polio ΔΔ (FIG. 12K) where FIG. 12I was not stained with primary antibody. FIG. 12L shows a graph depicting the level of GFP expression in skeletal muscle tissue harvested from mice injected with HIPK3 Polio or HIPK3 Polio ΔΔ quantified by the corrected total cell fluorescence (CTCF) method.

FIGS. 13A and 13B show immunofluorescent staining of sectioned liver tissue for GFP expression in tissues harvested from mice injected with HIPK3 Polio where FIG. 13B is a magnification of FIG. 13A. FIGS. 13C and 13D show immunofluorescent staining of sectioned liver tissue for GFP expression in tissues harvested from mice injected with HIPK3 Polio ΔΔ where FIG. 13D is a magnification of FIG. 13C.

DETAILED DESCRIPTION

Figure 1A:
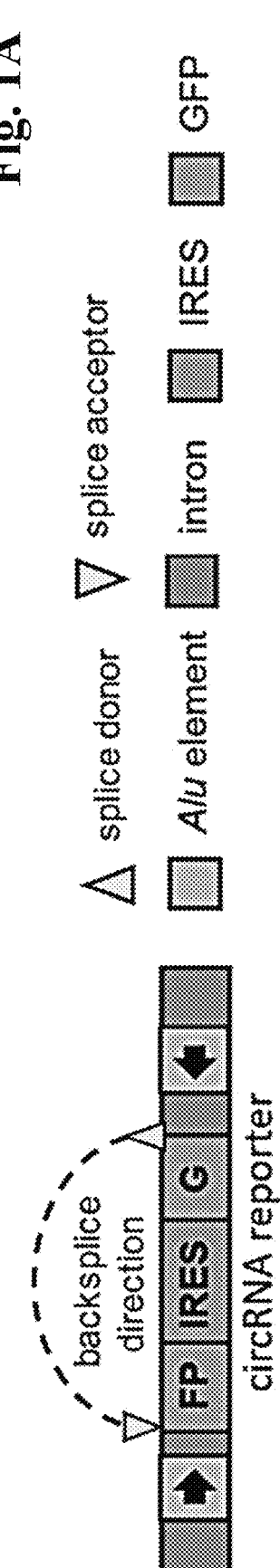
Figure 1B:
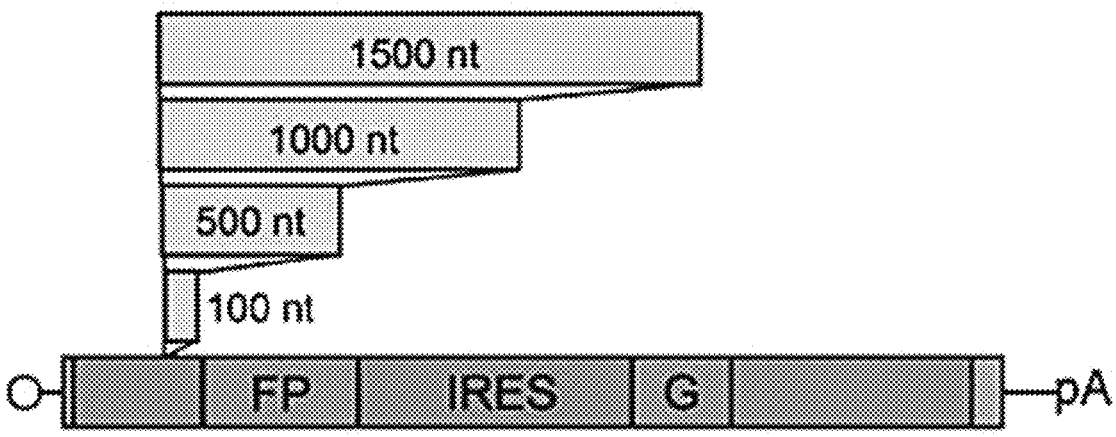
FIGS. 1B-1F are schematics, images, and graphs showing sequence insertions left of the HIPK3 intron.

RNA modulation has become a promising therapeutic approach for the treatment of several types of disease with circular RNAs (circRNAs) rapidly becoming attractive templates for expression of therapeutic proteins and non-coding RNAs. The present disclosure is based, at least in part, on the finding that additional inserts into a nucleic acid molecule encoding for at least two circular RNA (circRNAs) tolerated within the right intron can be exploited to create bi-functional RNA molecules from a single template. Specifically, the disclosure provides for tRNA intron-derived circRNA that can be incorporated within the intronic sequence without affecting backspliced circRNA formation. The findings herein provide for rational design of synthetic circRNAs allowing for incorporation of an aptamer, a guide RNA, a protein sponge, a miRNA sponge, a protein-binding RNA, a naturally occurring circRNA, an antisense RNA, a miRNA precursor, a siRNA precursor, a long non-coding RNA (lncRNA), a small activating RNA (saRNA), a functional non-coding RNA such as transfer RNA (tRNA), ribosomal RNA (rRNA), small nucleolar RNA (snoRNA), small nuclear RNA (snRNA), piwi-interacting RNA (piRNA), Y-RNA, 7SK RNA, 7S RNA, and the like that can be packaged into recombinant AAV vectors for therapeutic delivery.

I. Definitions

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

As used in the specification, articles "a" and "an" are used herein to refer to one or to more than one (i.e., at least one) of the grammatical object of the article. By way of example, "an element" means at least one element and can comprise more than one element.

"About" is used to provide flexibility to a numerical range endpoint by providing that a given value may be "slightly above" or "slightly below" the endpoint without affecting the desired result. The term "about" in association with a numerical value means that the numerical value can vary plus or minus by 5% or less of the numerical value.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise-indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

As used herein, "prevent" or "prevention" refers to eliminating or delaying the onset of a particular disease, disorder or physiological condition, or to the reduction of the degree of severity of a particular disease, disorder or physiological condition, relative to the time and/or degree of onset or severity in the absence of intervention.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. In some embodiments, the subject comprises a human. In other embodiments, the subject comprises a human in need of treatment for a disease or illness.

Unless otherwise defined, all technical terms used herein have the same meaning as commonly understood by one of ordinary skill in the art to which this disclosure belongs.

I. Nucleic Acid Molecule Compositions

In certain embodiments, the present disclosure provides a nucleic acid molecule encoding at least one a circular RNA (circRNA) that is covalently closed. In some embodiments, a nucleic acid molecule herein comprises one or more of the following: a) a circRNA-encoding sequence which can be transcribed into noncoding RNA or a translatable mRNA; b) one or more intronic elements that flank the circRNA-encoding sequence, wherein the intronic elements are backspliced by the cellular splicing machinery to yield a circular RNA that is covalently closed; c) an internal ribosome entry site (IRES) driving translation of the translatable mRNA transcribed from the circRNA-encoding sequence; d) a promoter upstream of the intronic elements that flank the circRNA-encoding sequence; and e) a translation regulating region in the 3' UTR and outside of the intronic elements that flank the circRNA-encoding sequence.

In certain embodiments, the present disclosure provides a nucleic acid molecule encoding at least two a circular RNAs (circRNAs). In some embodiments, compositions herein having nucleic acid molecule encoding for at least two circular RNA (circRNAs) can optionally comprise a first circRNA having a first circRNA-encoding sequence of interest, and a second circRNA having a second circRNA-encoding sequence of interest, wherein the second circRNA is in tandem to the first circRNA-encoding sequence of interest of the first circRNA, In some aspects, the first circRNA-encoding sequence of interest and the second circRNA in tandem can be flanked by intronic elements.

In certain embodiments, a first circRNA having a first circRNA-encoding sequence of interest can further include an internal ribosome entry site (IRES). Non-limiting examples of IRES suitable for use herein are encephelomyocarditis virus (EMCV) IRES, poliovirus IRES, Kaposi sarcoma-associated herpesvirus (KSHV) vFLIP IRES, hepatitis C virus (HCV) IRES, or any combination thereof. In some embodiments, an IRES suitable for use herein can share at least 85% (e.g., at least 85%, 90%, 95%, 99%, 100%) sequence similarity to any one of SEQ ID NOs: 26-29.

In certain embodiments, a first circRNA having a first circRNA-encoding sequence of interest can further include a promoter region upstream of the intronic elements that flank the first circRNA-encoding sequence and the second circRNA-encoding sequence in tandem. In some embodiments, a promoter can be a human cytomegalovirus (CMV) promoter, a truncated chimeric CMV-chicken 3-actin (smCBA) promoter, a mammalian 3-actin promoter, an albumin promoter and the like. In some embodiments, a promoter can be a polymerase II-driven promoter. Promoters, in general, are well-known to the art.

In certain embodiments, nucleic acid molecules herein can comprise at least one promoter region that can recruit an RNA polymerase. Promoters control the binding of RNA polymerase to DNA to initiate the transcription of genes. There are currently three types of RNA polymerases known that all transcribe different genes: RNA polymerase type I can transcribe genes encoding ribosomal RNA (rRNA); RNA polymerase type II can transcribe messenger RNA (mRNA); and RNA polymerase type III can transcribe genes encoding transfer RNAs (tRNA). RNA Polymerase type III can also transcribe small RNAs, such as shRNAs and gRNAs. In some embodiments, nucleic acid molecules herein can comprise at least one promoter region that can recruit RNA polymerase type I, II, III, or any combination thereof. In some embodiments, nucleic acid molecules herein can comprise a promoter region that can recruit RNA polymerase type II or III.

In certain embodiments, a first circRNA having a first circRNA-encoding sequence of interest can further include a translation regulating region in the 3' UTR and outside of the intronic elements that flank the first circRNA-encoding sequence of interest and the second circRNA in tandem.

In certain embodiments, a first circRNA having a first circRNA-encoding sequence of interest can have one or more intronic elements that flank the circRNA-encoding sequence, wherein the intronic elements are backspliced by the cellular splicing machinery to yield a circular RNA that is covalently closed. In some embodiments, the intronic elements flanking the first circRNA-encoding sequence of interest herein and the second circRNA in tandem herein are backspliced to yield the at least two circRNAs without forming a scar at a site wherein the circRNAs are covalently closed. As used herein, a "scar" in a circRNA can be generated at the site where intronic elements are connected to yield a circular RNA. In the present disclosure, the at least two circRNAs herein can form a seamless circular RNA (i.e., a circRNA that does not have a scar at the site wherein the circRNAs are covalently closed).

In certain embodiments, a first circRNA having a first circRNA-encoding sequence of interest can have one or more intronic elements that flank the circRNA-encoding sequence, wherein the one or more intronic elements can share about 85% (e.g., about 85%, about 90%, about 95%, about 99%, about 100%) sequence similarity to any one of SEQ ID NOS: 1, 2, 6, 7, 11, 12, and 20-25.

In certain embodiments, a first circRNA having a first circRNA-encoding sequence of interest can have one or more intronic elements that flank the circRNA-encoding sequence, wherein the one or more intronic elements can have an Alu element (or complementary region) sharing about 85% (e.g., about 85%, about 90%, about 95%, about 99%, about 100%) sequence similarity to any one of SEQ ID NOs: 3, 4, 8, 9, 13, and/or 14. In certain embodiments, a first circRNA having a first circRNA-encoding sequence of interest can have one or more intronic elements that flank the circRNA-encoding sequence, wherein the one or more intronic elements can have a poly-pyrimidine tract sharing about 85% (e.g., about 85%, about 90%, about 95%, about 99%, about 100%) sequence similarity to any one of SEQ ID NOs: 5, 10, and/or 15. In certain embodiments, a first circRNA having a first circRNA-encoding sequence of interest can have one or more intronic elements that flank the circRNA-encoding sequence, wherein the one or more intronic elements can have a splice site sharing about 85% (e.g., about 85%, about 90%, about 95%, about 99%, about 100%) sequence similarity to any one of the following: CAGGTAGGT (HIPK3), CAGGTAAGT (Laccase2), and/or CAGGTAAGA (ZKSCAN1).

In some embodiments, the intronic elements herein flanking at least one circRNA-encoding sequence of interest can have one or more insertions in the naturally occurring nucleic acid sequence. In some aspects, one or more insertions in the naturally occurring nucleic acid sequence the intronic elements herein can be an insertion of at least about 1 to about 1000 nucleic acids. In some aspects, one or more insertions in the naturally occurring nucleic acid sequence the intronic elements herein can be an insertion of at least about 1 to about 1000 nucleic acids in the intron flanking the circRNA-encoding sequence on the left. In some aspects, one or more insertions in the naturally occurring nucleic acid sequence the intronic elements herein can be an insertion of at least about 1 to about 1000 nucleic acids in the intron flanking the circRNA-encoding sequence on the right.

In some embodiments, the intronic elements herein flanking at least one circRNA-encoding sequence of interest can have one or more deletions in the naturally occurring nucleic acid sequence. In some aspects, one or more deletions in the naturally occurring nucleic acid sequence the intronic elements herein can be a deletion of at least about 1 to about 2000 nucleic acids. In some aspects, one or more deletions in the naturally occurring nucleic acid sequence the intronic elements herein can be a deletion of at least about 1 to about 2000 nucleic acids in the intron flanking the circRNA-encoding sequence on the left. In some aspects, one or more deletions in the naturally occurring nucleic acid sequence the intronic elements herein can be a deletion of at least about 1 to about 2000 nucleic acids in the intron flanking the circRNA-encoding sequence on the right.

In some embodiments, an intron pair herein flanking at least one circRNA-encoding sequence of interest can comprise a deletion of at least about 500 nucleotides (e.g., about 500 nucleotides, about 550 nucleotides, about 600 nucleotides, about 650 nucleotides, about 700 nucleotides, about 750 nucleotides, about 800 nucleotides, about 850 nucleotides, about 900 nucleotides, about 950 nucleotides, about 1000 nucleotides, about 1500 nucleotides). In some embodiments, an intron pair herein flanking at least one circRNA-encoding sequence of interest can have a left intron comprising a deletion of about 100 to about 500 (e.g., about 100, 150, 200, 250, 300, 350, 400, 450, 500) nucleotides. In some embodiments, an intron pair herein flanking at least one circRNA-encoding sequence of interest can have a left intron comprising a deletion of about 250 nucleotides. In some embodiments, an intron pair herein flanking at least one circRNA-encoding sequence of interest can have a right intron comprising a deletion of about 300 to about 900 (e.g., about 300, 350, 400, 450, 500, 550, 600, 650, 700, 750, 800, 850, 900) nucleotides. In some embodiments, an intron pair herein flanking at least one circRNA-encoding sequence of interest can have a right intron comprising a deletion of about 500 nucleotides. In some embodiments, an intron pair herein flanking at least one circRNA-encoding sequence of interest can have a left intron comprising a deletion of about 100 to about 500 (e.g., about 100, 150, 200, 250, 300, 350, 400, 450, 500) nucleotides and a right intron comprising a deletion of about 300 to about 900 (e.g., about 300, 350, 400, 450, 500, 550, 600, 650, 700, 750, 800, 850, 900) nucleotides. In some embodiments, an intron pair herein flanking the at least one circRNA-encoding sequence of interest comprises a left intron comprising a deletion of about 250 nucleotides and a right intron comprising a deletion of about 500 nucleotides.

In certain embodiments, compositions herein having a nucleic acid molecule encoding for at least two circular RNA (circRNAs) can produce at least one circRNA via backsplicing and at least one circRNA via self-splicing. In some embodiments, circRNA formed via self-splicing can be a tRNA intronic circular RNAs, or "tricRNAs." In some embodiments, compositions herein having a nucleic acid molecule encoding for at least two circular RNA (circRNAs) can produce one or more tricRNAs. In some embodiments, compositions herein having a nucleic acid molecule encoding for at least two circular RNA (circRNAs) can produce about one to about 50 tricRNAs, about one to about 40 tricRNAs, one to about 30 tricRNAs, one to about 20 tricRNAs, one to about 10 tricRNAs, or one to about 5 tricRNAs. In some embodiments, compositions herein having a nucleic acid molecule encoding for at least two circular RNA (circRNAs) can produce one or more tRNA introns having about 85% (e.g., about 85%, about 90%, about 95%, about 99%, about 100%) sequence similarity to any one of SEQ ID NOs: 17-18.

In some embodiments, tRNA intronic elements herein may include any known tRNA intronic element(s), in any combination and in any multiples and/or ratios. Examples of tRNA intronic elements suitable for use herein can include those described in Abelson et al., *J Biol Chem.* 273(21): 12685-8 (1998) and/or Schmidt et al., *Wiley Interdiscip Rev RNA.* 11(3):e1583 (2020), the disclosures of which are incorporated by reference herein in their entirety.

In some embodiments, compositions herein having a nucleic acid molecule encoding for at least two circular RNA (circRNAs) can have an insertion of nucleic acids in the right intron flanking a circRNA-encoding sequence of interest. In some embodiments, compositions herein can have an insertion of nucleic acids in the right intron flanking a circRNA-encoding sequence of interest, wherein the insertion can be about 0.1 kb to about 2.0 kb (e.g., about 0.1, 0.25, 0.5, 0.75, 1.0, 1.25, 1.5, 1.75, 2.0 kb). In some embodiments, compositions herein can have an insertion of nucleic acids in the right intron flanking a circRNA-encoding sequence of interest, wherein the insertion can be about 1.5 kb. In some embodiments, compositions herein can have an insertion of nucleic acids in the right intron flanking a circRNA-encoding sequence of interest, wherein the insertion can produce at least one circRNA via backsplicing. In some embodiments, compositions herein can have an insertion of nucleic acids in the right intron flanking a circRNA-encoding sequence of interest, wherein the insertion can produce at least one circRNA via elf-splicing. In some embodiments, compositions herein can have an insertion of nucleic acids in the right intron flanking a circRNA-encoding sequence of interest, wherein the insertion can produce one or more tricRNAs.

In some embodiments, compositions herein having a nucleic acid molecule encoding for at least two circular RNA (circRNAs) can produce one or more circRNAs that each encode for an aptamer, a guide RNA, a protein sponge, a miRNA sponge, a protein-binding RNA, a naturally occurring circRNA, an antisense RNA, a long non-coding RNA (lncRNA), a small activating RNA (saRNA), a functional non-coding RNA such as transfer RNA (tRNA), ribosomal RNA (rRNA), small nucleolar RNA (snoRNA), small nuclear RNA (snRNA), piwi-interacting RNA (piRNA), Y-RNA, 7SK RNA, 7S RNA, or any combination thereof. In some embodiments, compositions herein can produce at least one circRNA via backsplicing wherein the circRNA can encode for an aptamer, a guide RNA, a protein sponge, a miRNA sponge, a protein-binding RNA, a naturally occurring circRNA, an antisense RNA, a long non-coding RNA (lncRNA), a small activating RNA (saRNA), a functional non-coding RNA such as transfer RNA (tRNA), ribosomal RNA (rRNA), small nucleolar RNA (snoRNA), small nuclear RNA (snRNA), piwi-interacting RNA (piRNA), Y-RNA, 7SK RNA, 7S RNA, or any combination thereof. In some embodiments, compositions herein can produce at least one circRNA via self-splicing wherein the circRNA can encode for an aptamer, a guide RNA, a protein sponge, a miRNA sponge, a protein-binding RNA, a naturally occurring circRNA, an antisense RNA, a long non-coding RNA (lncRNA), a small activating RNA (saRNA), a functional non-coding RNA such as transfer RNA (tRNA), ribosomal RNA (rRNA), small nucleolar RNA (snoRNA), small nuclear RNA (snRNA), piwi-interacting RNA (piRNA), Y-RNA, 7SK RNA, 7S RNA, or any combination thereof. In some embodiments, compositions herein can produce one or more tricRNAs that can encode for an aptamer, a guide RNA, a protein sponge, a miRNA sponge, a protein-binding RNA, a naturally occurring circRNA, an antisense RNA, a long non-coding RNA (lncRNA), a small activating RNA (saRNA), a functional non-coding RNA such as transfer RNA (tRNA), ribosomal RNA (rRNA), small nucleolar RNA (snoRNA), small nuclear RNA (snRNA), piwi-interacting RNA (piRNA), Y-RNA, 7SK RNA, 7S RNA, or any combination thereof.

In some embodiments, compositions herein having a nucleic acid molecule encoding for at least two circular RNA (circRNAs) can be made using conventional techniques of molecular biology (including recombinant techniques) known in the art. Such techniques are explained fully in the literature, such as in *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; and *Cell Biology: A Laboratory Notebook* (J. E. Cellis, ed., 1989) Academic Press.

II. AAV Viral Particles

In certain embodiments, the present disclosure provides AAV viral particles for use as a vehicle for delivering any of the circRNAs disclosed herein to a subject.

Adeno-associated virus (AAV), a member of the Parvovirus family, is a small, non-enveloped virus. AAV particles suitable for used herein may include an AAV capsid composed of capsid protein subunits, VP1, VP2 and VP3, which enclose a single-stranded DNA genome.

In some embodiments, AAV viral particles disclosed herein can carry a single-stranded AAV DNA vector, which may comprise any of the circRNAs disclosed herein. In some embodiments, a circRNA coding sequence can be in operable linkage to a suitable promoter that drives expression of the circRNA. In some instances, an AAV DNA vector herein may comprise one or more regulatory elements that regulate expression of circRNA, for example, one or more miRNA binding sites, enhancers, transcriptional factor binding sites, polyA signaling elements, or a combination thereof.

(A) AAV Vectors

In certain embodiments, AAV viral particles disclosed herein can have an AAV vector for expressing one or more of the circRNAs disclosed herein. An AAV vector is derived from the wild type genome of a virus, such as AAV, by using molecular methods to remove the wild type genome from the virus (e.g., AAV), and replacing with a non-native nucleic acid, such as a heterologous polynucleotide sequence (e.g., a coding sequence for a circRNA). Typically, for AAV vectors, one or both inverted terminal repeat (ITR) sequences of the wild type AAV genome are retained in the AAV vector whereas other parts of the wild type viral genome are replaced with a non-native sequence such as a heterologous polynucleotide sequence between the retained ITRs. The AAV vectors disclosed herein can encompass AAV genome-derived backbone elements, a coding sequence for a circRNA disclosed herein, and a suitable promoter in operable linkage to the coding sequence. In some examples, the AAV vector disclosed herein can further comprise regulatory sequences regulating expression and/or secretion of the encoded protein. Examples include, but are not limited to, enhancers, polyadenylation signal sites, internal ribosome entry sites (IRES), sequences encoding protein transduction domains (PTD), microRNA-target sites, or a combination thereof.

In some examples, an AAV vector herein may be a regular AAV vector comprising a single stranded nucleic acid. In other examples, the AAV vector disclosed herein may be a self-complementary AAV vector capable of comprising double stranded portions therein.

(1) AAV-Backbone Elements

In some embodiments, AAV vectors disclosed herein can have one or more AAV-genome derived backbone elements, which refer to the minimum AAV genome elements required for the bioactivity of the AAV vectors. For example, the AAV-genome derived backbone elements may include the packaging site for the AAV vector to be assembled into an AAV viral particle, elements needed for vector replication and/or expression of the circRNA-encoding sequence comprised therein in host cells.

In some examples, AAV vector backbones disclosed herein may include at least one inverted terminal repeat (ITR) sequence. In some examples, AAV vector backbones herein include two ITR sequences. In some examples, one ITR sequence is 5' of a polynucleotide sequence coding for a circRNA. In some examples, one ITR sequence is 3' of a polynucleotide sequence coding for a circRNA. In some examples, of a polynucleotide sequence coding for a circRNA herein is flanked on either side by an ITR sequence.

In some embodiments, an AAV vector herein includes sequences or components originating from at least one distinct AAV serotype. In some examples, AAV vector backbones disclosed herein may include at least ITR sequence from one distinct AAV serotype. In some examples, AAV vector backbones disclosed herein may include at least ITR sequence from one distinct human AAV serotype. Such a human AAV may be derived from any known serotype, e.g. from any one of serotypes 1-11. In some examples, AAV serotypes used herein have a tropism for the central nervous system (CNS), cardiac tissues, skeletal muscle, and/or liver tissues. In some examples, AAV vector backbones disclosed herein may have an ITR sequence of serotype AAV1, AAV2, AAV4, AAV5, AAV8, or AAV9.

In some embodiments, an AAV vector herein can be a pseudotyped AAV vector, (i.e., comprises sequences or components originating from at least two distinct AAV serotypes). In some embodiments, a pseudotyped AAV vector herein includes an AAV genome backbone derived from one AAV serotype, and a Capsid derived at least in part from a distinct AAV serotype. In some examples, pseudotyped AAV vectors herein can have an AAV2 genome backbone and a Capsid derived from an AAV serotype having a tropism for CNS (e.g., AAV1, AAV2, AAV4, AAV5, AAV8, or AAV9). Specific examples of such pseudotyped AAV vectors include, without limitation, vectors comprising an AAV2-derived genome in an AAV5-derived capsid; or vectors comprising an AAV2-derived genome in an AAV8-derived capsid; or vectors comprising an AAV2-derived genome in an AAV9-derived capsid or vectors comprising an AAV2-derived genome in an AAV1-derived capsid.

In order to analyze the success of viral vector-mediated gene transfer, it may be important to be able to monitor both the distribution of the vector and the effectiveness of vector-mediated gene expression. This can be achieved by subcloning a reporter gene into the viral vector backbone. In some examples, AAV vector backbones disclosed herein may contain a reporter gene. Several reporter genes are commonly used for this purpose include, but are not limited to, fluorescent proteins of various colors (including green fluorescent protein (GFP), red fluorescent protein (RFP)), *E. coli* β-galactosidase (LacZ), and various forms of luciferase (Luc). In some examples, AAV vector backbones disclosed herein may contain GFP.

The vector constructs disclosed herein may be prepared using known techniques. (see e.g. *Current Protocols in Molecular Biology*, Ausubel., F. et al., eds, *Wiley and Sons*, New York 1995). Fragment length can be chosen so that the recombinant genome does not exceed the packaging capacity of the AAV particle. If necessary, a "stuffer" DNA sequence is added to the construct to maintain standard AAV genome size for comparative purposes. Such a fragment may be derived from such non-viral sources, e.g., lacZ, or other genes which are known and available to those skilled in the art.

(2) Self-Complementary AAV Viral Vectors

In some embodiments, AAV vectors disclosed herein can be self-complementary AAV (scAAV) vectors. Self-complementary AAV (scAAV) vectors contains complementary sequences that are capable of spontaneously annealing (folding back on itself to form a double-stranded genome) when entering into infected cells, thus circumventing the need for converting a single-stranded DNA vector using the cell's DNA replication machinery. An AAV herein having a self-complementing genome can quickly form a double stranded DNA molecule by virtue of its partially complementing sequences (e.g., complementing coding and non-coding strands of a circRNA-encoding sequence).

In some embodiments, a scAAV viral vector disclosed herein may comprise a first heterologous polynucleotide sequence and a second heterologous polynucleotide sequence, which can form intrastrand base pairs. In some examples, the first heterologous polynucleotide sequence and the second heterologous polynucleotide sequence are linked by a sequence that facilitates intrastrand base pairing; e.g., to form a hairpin DNA structure. In some examples, the dimeric structure of a scAAV vector upon entering a cell can be stabilized by a mutation or a deletion of one of the two terminal resolution sites (trs). As trs are Rep-binding sites contained within each ITR, a mutation or a deletion of such trs may prevent cleavage of a dimeric structure of a scAAV vector by AAV Rep proteins to form monomers. In some embodiments, a scAAV viral vector disclosed herein may include a truncated 5' inverted terminal repeats (ITR), a truncated 3' ITR, or both. In some examples, the scAAV vector disclosed herein may comprise a truncated 3' ITR, in which the D region or a portion thereof (e.g., the terminal resolution sequence therein) may be deleted. Such a truncated 3' ITR may be located between the first heterologous polynucleotide sequence and a second heterologous polynucleotide sequence noted above.

(3) Promoters

In some embodiments, AAV vectors disclosed herein comprise further elements necessary for expression, such as at least one suitable promoter which controls the expression of the circRNA-encoding sequence. Such a promoter may be ubiquitous, tissue-specific, strong, weak, regulated, chimeric, etc., to allow efficient and suitable production of the protein in the infected tissue. The promoter may be homologous to the encoded protein, or heterologous, including cellular, viral, fungal, plant or synthetic promoters. Most preferred promoters for use in the present invention shall be functional in human cells. Non-limiting examples of ubiquitous promoters include viral promoters, particularly the CMV promoter, the RSV promoter, the SV40 promoter, etc. and cellular promoters such as the PGK (phosphoglycerate kinase) promoter. In some embodiments, a viral promoter herein can be a CMV promoter, a SV40 promoter, or any combination thereof. In some embodiments, a viral promoter herein can have one of the below sequences:

| PRO-MOTER | SEQUENCE | SEQ ID NO: |
|---|---|---|
| CMV | ATAGTAATCAATTACGGGGTCATTAGTTCA TAGCCCATATATGGAGTTCCGCGTTACATA ACTTACGGTAAATGGCCCGCCTGGCTGACC GCCCAACGACCCCCGCCCATTGACGTCAAT AATGACGTATGTTCCCATAGTAACGCCAAT AGGGACTTTCCATTGACGTCAATGGGTGGA GTATTTACGGTAAACTGCCCACTTGGCAGT ACATCAAGTGTATCATATGCCAAGTACGCC CCCTATTGACGTCAATGACGGTAAATGGCC CGCCTGGCATTATGCCCAGTACATGACCTT ATGGGACTTTCCTACTTGGCAGTACATCTA CGTATTAGTCATCGCTATTACCATGGTGAT GCGGTTTTGGCAGTACATCAATGGGCGTGG | 44 |

| PRO-MOTER | SEQUENCE | SEQ ID NO: |
|---|---|---|
| | ATAGCGGTTTGACTCACGGGGATTTCCAAG TCTCCACCCCATTGACGTCAATGGGAGTTT GTTTTGGCACCAAAATCAACGGGACTTTCC AAAATGTCGTAACAACTCCGCCCCATTGAC GCAAATGGGCGGTAGGCGTGTACGGTGGGA GGTCTATATAAGCAGAGCTGGTTTAGTGAA CCGTCAGATC | |
| SV40 poly-A | TGATCATAATCAGCCATACCACATTTGTAG AGGTTTTACTTGCTTTAAAAAACCTCCCAC ACCTCCCCCTGAACCTGAAACATAAAATGA ATGCAATTGTTGTTGTTAACTTGTTTATTG CAGCTTATAATGGTTACAAATAAAGCAATA GCATCACAAATTTCACAAATAAAGCATTTT TTTCACTGCATTCTAGTTGTGGTTTGTCCA AACTCATCAATGTATCTTA | 45 |

In some embodiments, viral promoters herein can share about 85% (e.g., about 85%, 90%, 95%, 99%, 100%) sequence similarity to any one of SEQ ID NOs: 44-45.

In some embodiments, AAV vectors disclosed herein comprise further elements necessary for expression, such as at least one suitable promoter which controls the expression of the circRNA-encoding sequence after infection of the appropriate cells. Suitable promoters for use herein include, in addition to the AAV promoters, e.g., the cytomegalovirus (CMV) promoter or the chicken beta actin/cytomegalovirus hybrid promoter (CAG), an endothelial cell-specific promoter such as the VE-cadherin promoter, as well as steroid promoters and metallothionein promoters. In some embodiments, the promoter used in the vectors disclosed herein can be a CAG promoter.

In some embodiments, the circRNA-encoding sequence according to the invention comprises a tissue specific promoter which is functionally linked to the circRNA-encoding sequence to be expressed. Accordingly, the specificity of the vectors according to the disclosure for the tissue (e.g., brain, heart, muscle, liver) can be further increased. In some examples, a vector disclosed herein can have a tissue-specific promoter whose activity in the specific tissue is at least 2-fold, 5-fold, 10-fold, 20-fold, 50-fold or 100-fold higher than in a tissue which is not the specific tissue. In some examples, a tissue specific promoter herein is a human a tissue specific promoter. In some examples, the expression cassette can also include an enhancer element for increasing the expression levels of exogenous protein to be expressed. Furthermore, the expression cassette may further comprise polyadenylation sequences, such as the SV40 polyadenylation sequences or polyadenylation sequences of bovine growth hormone. Generally, tissue specific promoters are well-known in the art.

(4) Other Regulatory Elements for Gene Expression

In some embodiments, AAV vectors disclosed herein may include one or more conventional control elements which are operably linked to the circRNA-encoding sequence in a manner which permits its transcription, translation and/or expression in a cell transfected with the plasmid vector or infected with the virus produced by the invention. As used herein, "operably linked" sequences include both expression control sequences that are contiguous with the circRNA-encoding sequence and expression control sequences that act in trans or at a distance to control the circRNA-encoding sequence. Expression control sequences may further comprise appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

In some embodiments, a AAV vector disclosed herein may include a modified capsid, including proteins or peptides of non-viral origin or structurally modified, to alter the tropism of the vector. For example, the capsid may include a ligand of a particular receptor, or a receptor of a particular ligand, to target the vector towards cell type(s) expressing said receptor or ligand, respectively.

(B) Serotype of AAV Viral Particles

In some embodiments, AAV vectors disclosed herein may be prepared or derived from various serotypes of AAVs. The term "serotype" is a distinction with respect to an AAV having a capsid which is serologically distinct from other AAV serotypes. Serologic distinctiveness is determined on the basis of the lack of cross-reactivity between antibodies to the AAV as compared to other AAV. Cross-reactivity can be measured using methods known in the art. For example, cross-reactivity herein may be measured using a neutralizing antibody assay. For this assay polyclonal serum is generated against a specific AAV in a rabbit or other suitable animal model using the adeno-associated viruses. In this assay, the serum generated against a specific AAV is then tested in its ability to neutralize either the same (homologous) or a heterologous AAV. The dilution that achieves 50% neutralization is considered the neutralizing antibody titer. If for two AAVs the quotient of the heterologous titer divided by the homologous titer is lower than 16 in a reciprocal manner, those two vectors are considered as the same serotype. Conversely, if the ratio of the heterologous titer over the homologous titer is 16 or more in a reciprocal manner the two AAVs are considered distinct serotypes. In some examples, AAV vectors herein may be mixed of at least two serotypes of AAVs or with other types of viruses to produce chimeric (e.g., pseudotyped) AAV viruses. In a particular embodiment, the AAV vector for use in the present invention is a human serotype AAV vector. Such a human AAV may be derived from any known serotype, e,g., from any one of serotypes 1-11, more preferably from AAV1, AAV2, AAV4, AAV6 and AAV9. Specific examples of such AAV vectors are vectors comprising an AAV1-derived genome (a nucleic acid molecule comprising an AAV1-derived ITR and an AAV1-derived packaging sequence, operatively linked to a nucleic acid encoding a therapeutic protein, preferably two AAV1-derived ITR flanking an AAV1-derived packaging sequence and a nucleic acid encoding a therapeutic protein) in an AAV1-derived capsid; vectors comprising and AAV2-derived genome in an AAV2-derived capsid; vectors comprising and AAV4-derived genome in an AAV4-derived capsid; vectors comprising and AAV6-derived genome in an AAV6-derived capsid or vectors comprising and AAV9-derived genome in an AAV9-derived capsid.

(C) Methods of Making AAV particles

In some embodiments, AAV vectors herein may be packaged into virus particles which can be used to deliver the genome for circRNA-encoding sequence expression in target cells. In some embodiments, AAV vectors disclosed herein can be packaged into particles by transient transfection, use of producer cell lines, combining viral features into Ad-AAV hybrids, use of herpesvirus systems, or production in insect cells using baculoviruses.

A method of generating a packaging cell for use herein can involve creating a cell line that stably expresses all of the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing, addition of synthetic linkers containing restriction endonuclease cleavage sites, or by direct, blunt-end ligation. The packaging cell line is then infected with a helper virus, such as adenovirus. The advantages of this method are that the cells are selectable and are suitable for large-scale production of rAAV. Examples of suitable methods herein employ adenovirus or baculovirus, rather than plasmids, to introduce rAAV genomes and/or rep and cap genes into packaging cells.

III. Pharmaceutical Compositions

In some embodiments, any of the circRNAs and/or AAV viral particles disclosed herein may be formulated to form a pharmaceutical composition. In some examples, pharmaceutical composition herein can further include a pharmaceutically acceptable carrier, diluent or excipient. Any of the pharmaceutical compositions to be used in the present methods can comprise pharmaceutically acceptable carriers, excipients, or stabilizers in the form of lyophilized formations or aqueous solutions.

The carrier in the pharmaceutical composition must be "acceptable" in the sense that it is compatible with the active ingredient of the composition, and preferably, capable of stabilizing the active ingredient and not deleterious to the subject to be treated. For example, "pharmaceutically acceptable" may refer to molecular entities and other ingredients of compositions comprising such that are physiologically tolerable and do not typically produce untoward reactions when administered to a mammal (e.g., a human). In some examples, the "pharmaceutically acceptable" carrier used in the pharmaceutical compositions disclosed herein may be those approved by a regulatory agency of the Federal or a state government or listed in the U.S. Pharmacopeia or other generally recognized pharmacopeia for use in mammals, and more particularly in humans.

Pharmaceutically acceptable carriers, including buffers, are well known in the art, and may comprise phosphate, citrate, and other organic acids; antioxidants including ascorbic acid and methionine; preservatives; low molecular weight polypeptides; proteins, such as serum albumin, gelatin, or immunoglobulins; amino acids; hydrophobic polymers; monosaccharides; disaccharides; and other carbohydrates; metal complexes; and/or non-ionic surfactants. See, e.g. Remington: The Science and Practice of Pharmacy 20$^{th}$ Ed. (2000) Lippincott Williams and Wilkins, Ed. K. E. Hoover.

In some embodiments, the pharmaceutical compositions or formulations are for parenteral administration, such as intravenous, intracerebroventricular injection, intra-cisterna magna injection, intra-parenchymal injection, or a combination thereof. Such pharmaceutically acceptable carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG)

and glycerol solutions can also be employed as liquid carriers, particularly for injectable solutions. Pharmaceutical compositions disclosed herein may further comprise additional ingredients, for example preservatives, buffers, tonicity agents, antioxidants and stabilizers, nonionic wetting or clarifying agents, viscosity-increasing agents, and the like. The pharmaceutical compositions described herein can be packaged in single unit dosages or in multidosage forms.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. Aqueous solutions may be suitably buffered (preferably to a pH of from 3 to 9). The preparation of suitable parenteral formulations under sterile conditions is readily accomplished by standard pharmaceutical techniques well known to those skilled in the art.

The pharmaceutical compositions to be used for in vivo administration should be sterile. This is readily accomplished by, for example, filtration through sterile filtration membranes. Sterile injectable solutions are generally prepared by incorporating the active (e.g., circRNAs, AAV particles, compositions comprising circRNAs and/or AAV particles, etc.) in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

The pharmaceutical compositions disclosed herein may also comprise other ingredients such as diluents and adjuvants. Acceptable carriers, diluents and adjuvants are non-toxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycols.

IV. Methods of Use

Any of the compositions (e.g., nucleic acid molecule encoding for at one, two or more circular RNAs, AAV particles, AAV genomes) described herein can be used for alleviating and/or treating a disease or a condition. Thus, in some aspects, the present disclosure provides methods for alleviating one or more symptoms and/or for treating a disease or a condition in a subject in need of the treatment compositions disclosed herein, as well as a pharmaceutical compositions comprising such. Illustrative diseases or a conditions that can be treated using the methods disclosed herein can include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product, mir-26a [e.g., for hepatocellular carcinoma]), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, follistatin, activin type II soluble receptor, anti-inflammatory polypeptides such as the Ikappa B dominant mutant, sarcospan, utrophin, mini-utrophin, antisense or RNAi against splice junctions in the dystrophin gene to induce exon skipping (see, e.g., WO 2003/095647), antisense against U7 snRNAs to induce exon skipping (see, e.g., WO 2006/021724), and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic disorders, congenital emphysema (α1-antitrypsin), Lesch-Nyhan Syndrome (hypoxanthine guanine phosphoribosyl transferase), Niemann-Pick disease (sphingomyelinase), Tay Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration and/or vasohibin or other inhibitors of VEGF or other angiogenesis inhibitors to treat/prevent retinal disorders, e.g., in Type I diabetes), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1) and fragments thereof (e.g., IIC), serca2a, zinc finger proteins that regulate the phospholamban gene, Barkct, P2-adrenergic receptor, p2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like.

To perform the methods disclosed herein, a therapeutically effective amount of the compositions (e.g., circRNAs, AAV particles) or a pharmaceutical composition comprising such may be administered to a subject who needs treatment via a suitable route (e.g., intramuscular, intravenous, intracerebroventricular injection, intra-cisterna magna injection, intravitreal, subretinal, subconjuctival, retrobulbar, intracameral, suprachoroidal, intracoronary injection, intraarterial injection, and/or intra-parenchymal injection) at a suitable amount as disclosed herein.

In certain embodiments, the present disclosure also provides for methods of introducing a nucleic acid molecule into a cell, comprising contacting the cell with a virus vector and/or composition disclosed herein. In some embodiments, methods herein can include delivering a nucleic acid molecule herein to an eye cell, comprising contacting the eye cell or layer with a viral vector disclosed herein wherein the viral vector comprises the nucleic acid molecule of interest. In some embodiments of this method, a nucleic acid molecule of interest can encode a therapeutic protein or therapeutic RNA. In some embodiments, the therapeutic protein can be a monoclonal antibody or a fusion protein.

In certain embodiments, the present disclosure also provides for methods of introducing a nucleic acid molecule to a heart tissue, a liver tissue, a skeletal muscle tissue, or any combination thereof, comprising contacting the cell with a virus vector and/or composition disclosed herein. In some embodiments, nucleic acid molecules herein can be delivered to a specific tissue by administering AAV particles having one or more nucleic acid molecules herein to a heart tissue, a liver tissue, a skeletal muscle tissue, or any combination thereof.

In some embodiments, methods of administering at least one AAV particle having one or more nucleic acid molecules herein to a tissue substantially increases expression of the at least one circRNA as compared to baseline. As used herein, "baseline" refers to the expression of the at least one circRNA (and the encoded product of the circRNA) before the AAV particle having one or more nucleic acid molecules was administered. As used herein, "substantially increases expression" refers to at least a 1-fold change in expression as compared to baseline. In some embodiments, methods of administering at least one AAV particle having one or more nucleic acid molecules herein to a tissue increases expression of the at least one circRNA as compared to baseline by at least about 2-fold to about 50-fold (e.g., about 2-, 4-, 6-, 8-, 10-, 20-, 30-, 40-, 50-fold). In some embodiments, methods of administering at least one AAV particle having one or more nucleic acid molecules herein to a tissue increases expression of the at least one circRNA as compared to baseline by at least about 2-fold to about 50-fold e.g., about 2-, 4-, 6-, 8-, 10-, 20-, 30-, 40-, 50-fold) when the at least one AAV particle is delivered to a heart tissue, a liver tissue, a skeletal muscle tissue, or any combination thereof. In some embodiments, methods of administering at least one AAV particle having one or more nucleic acid molecules herein to a tissue increases expression of the at least one circRNA as compared to baseline by at least about 4-fold when the at least one AAV particle is delivered to a heart tissue, a liver tissue, or any combination thereof. In some embodiments, methods of administering at least one AAV particle having one or more nucleic acid molecules herein to a tissue increases expression of the at least one circRNA as compared to baseline by at least about 50-fold when the at least one AAV particle is delivered to skeletal muscle tissue.

In any of the methods disclosed herein, an effective amount of compositions (e.g., nucleic acid molecule encoding for at one, two or more circular RNAs, AAV particles, AAV genomes) described herein can be given to a subject in need thereof to alleviate one or more symptoms associated with a disease and or condition. "An effective amount" as used herein refers to a dose of a disclosed composition which is sufficient to confer a therapeutic effect on a subject having a disease and or condition. In some embodiments, an effective amount can be an amount that reduces at least one symptom of disease or condition in the subject.

V. Kits

The present disclosure also provides kits for use in preparing any one of the compositions (e.g., nucleic acid molecule encoding for one, two, or more circular RNAs, AAV particles, AAV genomes) as described herein and kits having one or more therapeutic uses as described herein. A kit for use as described herein may include one or more containers further including a composition (e.g., nucleic acid molecule encoding for one, two, or more circular RNAs, AAV particles, AAV genomes) as described herein, formulated in a pharmaceutical composition.

In some embodiments, the kit can additionally comprise instructions for use of compositions (e.g., nucleic acid molecule encoding for one, two, or more circular RNAs, AAV particles, AAV genomes) in any of the methods described herein. The included instructions may include a description of administration of the compositions or a pharmaceutical composition comprising such to a subject to achieve the intended activity in a subject. The kit may further comprise a description of selecting a subject suitable for treatment based on identifying whether the subject is in need of the treatment. The instructions relating to the use of the compositions as described herein generally include information as to dosage, dosing schedule, and route of administration for the intended treatment.

The containers may be unit doses, bulk packages (e.g., multi-dose packages) or sub-unit doses. Instructions supplied in the kits of the disclosure are typically written instructions on a label or package insert. The label or package insert indicates that the pharmaceutical compositions are used for treating, delaying the onset, and/or alleviating a disease or disorder in a subject.

The kits provided herein are in suitable packaging. Suitable packaging includes, but is not limited to, vials, bottles, jars, flexible packaging, and the like. Also contemplated are packages for use in combination with a specific device, such as an inhaler, nasal administration device, or an infusion device. A kit may have a sterile access port (for example, the container may be an intravenous solution bag or a vial having a stopper pierceable by a hypodermic injection needle). The container may also have a sterile access port.

Kits optionally may provide additional components such as buffers and interpretive information. Normally, the kit comprises a container and a label or package insert(s) on or associated with the container. In some embodiments, the disclosure provides articles of manufacture comprising contents of the kits described above.

In certain embodiments, the present disclosure provides for a nucleic acid molecule encoding a circular RNA (circRNA) that is covalently closed, wherein the nucleic acid molecule comprises: a) a gene of interest which can be transcribed into noncoding RNA or a translatable mRNA; b) intronic elements that flank the gene of interest, wherein the intronic elements are backspliced by the cellular splicing machinery to-yield a circular RNA that is covalently closed; c) an internal ribosome entry site (IRES) driving translation of the translatable mRNA transcribed from the gene of interest; d) a promoter region in the 5' untranslated region (UTR) and outside of the intronic elements that flank the gene of interest; and e) a translation regulating region in the 3' UTR and outside of the intronic elements that flank the gene of interest. In certain embodiments, the present disclosure provides for a nucleic acid molecule encoding a circular RNA (circRNA) that is covalently closed, wherein the nucleic acid molecule comprises: a) a circRNA-encoding sequence which can be transcribed into noncoding RNA or a translatable mRNA; b) intronic elements that flank the circRNA-encoding sequence, wherein the intronic elements are backspliced by the cellular splicing machinery to yield a circular RNA that is covalently closed; c) an internal ribosome entry site (IRES) driving translation of the translatable mRNA transcribed from the circRNA-encoding sequence, optionally comprising a self-splicing mechanism for cir-cRNA generation; d) a promoter region upstream of the intronic elements that flank the circRNA-encoding sequence; and e) a translation regulating region in the 3' UTR and outside of the intronic elements that flank the circRNA-encoding sequence. In some embodiments, the present disclosure provides for a nucleic acid molecule wherein the intronic elements of (b) (i.e., intronic elements that flank the gene of interest) comprise the nucleotide sequence of any of SEQ ID NOs 1, 2, 6, 7, 11, and/or 12, in any combination thereof, and in any multiples and/or ratios. In some embodiments, the present disclosure provides for a nucleic acid molecule wherein the intronic elements of (b) (i.e., intronic elements that flank the circRNA-encoding sequence) comprise the nucleotide sequence of any of SEQ ID NOs 20-25, in any combination thereof, and in any multiples and/or ratios. In some embodiments, the present disclosure provides for a nucleic acid molecule wherein the IRES of (c) comprise the nucleotide sequence of any of SEQ ID NOs 26-29, in any combination thereof, and in any multiples and/or ratios. In some embodiments, the present disclosure provides for a nucleic acid molecule wherein the translation regulating region of (e) is a polyadenylation (polyA) sequence and/or a structural element that stabilizes the circRNA.

For example, in certain embodiments, a disclosed nucleic acid molecule can comprise a viral IRES, such as, for example, a viral IRES listed in Table 1 below.

TABLE 1

| IRES-name | Virus Name | IRES Found In | IRES Size (nt) |
|---|---|---|---|
| ABPVIGRpred | ABPV | Acute bee paralysis virus | 199 |
| AEV | AEV | Avian encephalomyelitis virus | 494 |
| ALPV_IGRpred | ALPV | Aphid lethal paralysis virus | 184 |
| BQCV_IGRpred | BQCV | Black queen cell virus | 190 |
| BVDV1_1-385 | BVDV1 | Bovine viral diarrhea virus 1 | 385 |
| BVDV1_29-391 | BVDV1 | Bovine viral diarrhea virus 1 | 363 |
| CrPV_5NCR | CrPV | Cricket paralysis virus | 708 |
| CrPV_IGR | CrPV | Cricket paralysis virus | 192 |
| crTMV_IREScp | crTMV | *Crucifer tobamovirus* | 146 |
| crTMV_IRESmp75 | crTMV | *Crucifer tobamovirus* | 75 |
| crTMV_IRESmp228 | crTMV | *Crucifer tobamovirus* | 228 |
| crTMV_IREScp | crTMV | *Crucifer tobamovirus* | 148 |
| CSFV | CSFV | Classical swine fever virus | 373 |
| CVB3 | CVB3 | Human coxsackievirus B3 | 750 |
| DCV_IGR | DCV | *Drosophila* C virus | 189 |
| EMCV-R | EMCV-R | Encephalomyocarditis virus | 576 |
| EoPV_5NTR | EoPV | *Ectropis obliqua* picorna-like virus | 390 |
| ERAV_245-961 | ERAV | *Equine* rhinitis A virus 1 | 712 |
| ERB V_162-920 | ERBV | *Equine* rhinitis B virus | 759 |
| EV71_1-748 | EV71 | Human enterovirus 71 | 748 |
| FeLV-Notch2 | FeLV-Notch2 | *Felis* silvestris | 238 |
| FMDV_type_C | FMDV | Foot-and-mouth disease virus | 461 |
| GBV-A | GBV-A | Hepatitis GB virus A | 693 |
| GBV-B | GBV-B | Hepatitis GB virus B | 416 |
| GBV-C | GBV-C | Hepatitis GB virus C | 630 |
| gypsy_env | Gypsy | *Drosophila melanogaster* | 330 |
| gypsyD5 | Gypsy | *Drosophila melanogaster* | 261 |
| gypsyD2 | Gypsy | *Drosophila melanogaster* | 517 |
| HAVHM175 | HAV | Human hepatitis A virus | 584 |
| HCV_type_1a | HCV_type_1a | Hepatitis C virus | 383 |
| HiPV_IGRpred | HiPV | Himetobi P virus | 188 |
| HIV-1 | HIV-1 | Human Immunodeficiency Virus type 1 | 233 |
| HoCV1_IGRpred | HoCV-1 | Homalodiscacoagulata virus-1 | 188 |
| HRV-2 | HRV2 | Human rhinovirus 2 | 604 |
| IAPV_IGRpred | IAPV | Israel acute paralysis virus of bees | 199 |
| idefix | Idefix | *Drosophila melanogaster* | 521 |
| KBV_IGRpred | KBV | Kashmir bee virus | 202 |
| LINE-I_ORF1_−101_to_−1 | LINE-1 | *Mus musculus* | 101 |
| LINE-1_ORF1_−302_to_−202 | LINE-1 | *Mus musculus* | 101 |
| LINE-1_ORF2_−138_to_−86 | LINE-1 | *Mus musculus* | 53 |
| LINE-1_ORF1_−44_to_−1 | LINE-1 | *Mus musculus* | 47 |
| PSIVIGR | PSIV | *Plautia* stali intestine virus | 145 |
| PV_type1_Mahoney | PV | Human poliovirus 1 | 312 |
| PV_type3_Leon | PV | Human poliovirus 1 | 742 |

TABLE 1-continued

| IRES-name | Virus Name | IRES Found In | IRES Size (nt) |
|---|---|---|---|
| REV-A | REV-A | Reticuloendotheliosis virus | 577 |
| RhPV_5NCR | RhPV | *Rhopalosiphum padi* virus | 579 |
| RhPV_IGR | RhPV | *Rhopalosiphum padi* virus | 232 |
| SINV1_IGRpred | SINV-1 | *Solenopsis* invicta virus 1 | 200 |
| SV40_661-830 | SV40 | Simian virus 40 | 170 |
| TMEV | TMEV | Theiler's encephalomyelitis virus | 1040 |
| TMV_UI_IRESmp228 | TMV_type1 | Tobacco mosaic virus | 231 |
| TRV_5NTR | TrV | *Triatoma* virus | 694 |
| TrV_IGR | TrV | *Triatoma* virus | 221 |
| TSV_IGR | TSV | Taura syndrome virus | 250 |

For example, in certain embodiments, a disclosed nucleic acid molecule can comprise a cellular IRES, such as, for example, a cellular IRES listed in Table 2 below.

TABLE 2

| IRES-name | Source Name | IRES Size (nt) |
|---|---|---|
| AML1/RUNX1 | AML1/RUNX1 | 1561 |
| Antp-D | Antp | 252 |
| Antp-DE | Antp | 408 |
| Antp-CDE | Antp | 1730 |
| Apaf-1 | Apaf-1 | 583 |
| Apaf-1 | Apaf-1 | 231 |
| AQP4 | AQP4 | 284 |
| AT1R_var1 | hAT1R-B | 356 |
| AT1R_var2 | hAT1R-A | 272 |
| AT1R_var3 | hAT1R-C | 330 |
| AT1R_var4 | hAT1R-D | 414 |
| BAG1_p36delta236nt | BAG-1 | 130 |
| BAG1_p36 | BAG-1 | 366 |
| BCL2 | BCL2 | 1137 |
| BiP_−222_−3 | BiP | 222 |
| C-IAP1_285-1399 | c-IAP1 | 1115 |
| C-IAP1_1313-1462 | c-IAP1 | 150 |
| c-jun | c-jun | 301 |
| c-myc | c-myc | 393 |
| Cat-1_224 | Cat-1 | 224 |
| CCND1 | CCND1 | 209 |
| DAPS | DAPS | 305 |
| eIF4G | eIF4G | 357 |
| eIF4GI-ext | eIF4GI | 196 |
| eIF4GII | eIF4GII | 256 |
| eIF4GII-long | eIF4GII | 327 |
| ELG1 | ELG1 | 460 |
| ELH | ELH | 319 |
| FGF1A | FGF1 | 434 |
| FMR1 | FMR1 | 252 |
| Gtx-133-141 | Gtx | 9 |
| Gtx-1-166 | Gtx | 166 |
| Gtx-1-120 | Gtx | 120 |
| Gtx-1-196 | Gtx | 196 |
| hairless | Hairless | 435 |
| HAP4 | HAP4 | 270 |
| HIF1a | Hif1a | 257 |
| hSNM1 | hSNM1 | 918 |
| Hsp101 | Hsp101 | 161 |
| hsp70 | Hsp70Aa | 503 |
| hsp70 | HSPA1A | 193 |
| Hsp90 | Hsp83 | 149 |
| IGF2_leader2 | IGF2 | 121 |
| Kv1.4_1.2 | Kcna4 | 1197 |
| L-myc | L-myc | 52 |
| LamB1_−335-l | LamB1 | 335 |
| LEF1 | LEF1 | 1167 |
| MNT_75-267 | MNT | 193 |
| MNT_36-160 | MNT | 125 |
| MTG8a | MTG8a | 199 |
| MYB | c-myb | 150 |
| MYT2_997-1152 | MYT2 | 156 |
| n-MYC | n-MYC | 320 |
| NDST1 | NDST1 | 420 |
| NDST2 | NDST2 | 750 |

TABLE 2-continued

| IRES-name | Source Name | IRES Size (nt) |
|---|---|---|
| NDST3 | NDST3 | 247 |
| NDST4L | NDST4L | 672 |
| NDST4S | NDST4S | 418 |
| NRF_−653_−17 | NRF | 637 |
| NtHSF1 | NtHSF1 | 453 |
| ODC1 | ODC1 | 303 |
| p27kip1 | p27kip1 | 152 |
| p53_128-269 | p53/p47 | 142 |
| PDGF2/c-sis | PDGF2/c-sis | 1022 |
| Pim-1 | PIM1 | 396 |
| PITSLRE_p58 | PITSLRE | 381 |
| Rbm3 | Rbm3 | 22 |
| reaper | Rpr | 168 |
| Scamper | Scamper | 365 |
| TFIID | TBP1 | 188 |
| TIF4631 | TIF4631 | 348 |
| Ubx_1-966 | Ubx | 966 |
| Ubx_373-961 | Ubx | 589 |
| UNR | UNR | 429 |
| Ure2 | Ure2 | 167 |
| UtrA | Utm | 506 |
| VEGF-A_−133_−1 | VEGF-A | 133 |
| XIAP_5-464 | XIAP | 460 |
| XIAP_305-466 | XIAP | 162 |
| YAP1 | YAP1 | 164 |

In an aspect, a disclosed nucleic acid molecule can comprise a combination of one or more IRES, such as, for example, a virus IRES or a cellular IRES. In an aspect, a combination of one or more IRES comprise one or more virus IRES. In an aspect, a combination of one or more IRES comprise one or more cellular IRES. In an aspect, a combination of one or more IRES comprise both viral IRES and cellular IRES. In certain embodiments, the present disclosure provides for a nucleic acid molecule comprising IRES wherein IRES is a viral IRES listed in Table 1, a cellular IRES listed in Table 2, in any combination thereof, and in any multiples and/or ratios.

In certain embodiments, the present disclosure provides for an adeno-associated virus (AAV) genome comprising any one of the nucleic acid molecule disclosed herein, flanked by AAV inverted terminal repeats (ITRs). In some embodiments, the present disclosure provides for an AAV capsid or particle comprising an AAV genome disclosed herein. In some embodiments, the present disclosure provides for an AAV capsid or particle comprising any of the nucleic acid molecule disclosed herein.

In certain embodiments, the present disclosure provides for a composition comprising any of the nucleic acid molecules disclosed herein, any of the AAV genomes disclosed herein, and/or any of the AAV capsids or particles disclosed herein, in a pharmaceutically acceptable carrier.

In certain embodiments, the present disclosure provides for a method of expressing a covalently closed circular RNA molecule in a cell, comprising introducing into the cell any one of the nucleic acid molecules disclosed herein, under conditions wherein the covalently closed circular RNA molecule is transcribed and/or produced.

In certain embodiments, the present disclosure provides for a method of expressing a covalently closed circular RNA molecule in a cell, comprising introducing into the cell any of the AAV genomes disclosed herein, under conditions wherein the covalently closed circular RNA molecule is transcribed.

In certain embodiments, the present disclosure provides for a method of expressing a covalently closed circular RNA molecule in a cell, comprising introducing into the cell any of the AAV capsids or particles disclosed herein, under conditions wherein the covalently closed circular RNA molecule is transcribed.

In certain embodiments, the present disclosure provides for a method of expressing a covalently closed circular RNA molecule in a cell, comprising introducing into the cell any of the compositions disclosed herein, under conditions wherein the covalently closed circular RNA molecule is transcribed.

In certain embodiments, the present disclosure provides for a method of expressing a covalently closed circular RNA molecule in a tissue specific and/or cell specific manner, comprising contacting the tissue and/or the cell with any of the nucleic acid molecules disclosed herein, under conditions wherein the covalently closed, circular RNA molecule is expressed.

In certain embodiments, the present disclosure provides for a method of expressing a covalently closed circular RNA molecule in a tissue specific and/or cell specific manner, comprising contacting the tissue and/or the cell with any of the AAV genomes disclosed herein, under conditions wherein the covalently closed, circular RNA molecule is expressed.

In certain embodiments, the present disclosure provides for a method of expressing a covalently closed circular RNA molecule in a tissue specific and/or cell specific manner, comprising contacting the tissue and/or the cell with any of the AAV capsids or particles disclosed herein, under conditions wherein the covalently closed, circular RNA molecule is expressed.

In certain embodiments, the present disclosure provides for a method of expressing a covalently closed circular RNA molecule in a tissue specific and/or cell specific manner, comprising contacting the tissue and/or the cell with any of the compositions disclosed herein, under conditions wherein the covalently closed, circular RNA molecule is expressed.

In some embodiments, the present disclosure provides for any of the methods herein, wherein the covalently closed circular RNA molecule is a therapeutic mRNA molecule encoding a protein, an RNA silencing molecule, a guide RNA molecule that can target a genomic element, a guide RNA molecule that can target an RNA transcript, a tRNA molecule, a long noncoding RNA molecule, an antisense RNA molecule, or any combination thereof.

In some embodiments, the present disclosure provides for any of the methods herein, wherein the covalently closed circular RNA molecule is a naturally occurring circRNA molecule, a functional non-coding RNA molecule, or any combination thereof.

In some embodiments, the present disclosure provides for any of the methods herein, wherein the cell and/or tissue is from a mammal.

EXAMPLES

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit, and scope of the present disclosure. All such modifications are intended to be within the scope of the disclosure.

Example 1. Backsplicing Introns Tolerate
Insertions, Allowing for Dual circRNA Expression A common feature of introns that mediate backsplicing is the presence of inverted Alu elements or other complementary sequences. To interrogate how the distance between these complementary regions and splice donor/acceptor sites affects backsplicing of a circRNA, a reporter system, as shown in FIG. 1A, containing introns from the HIPK3 gene to drive circularization of a split GFP exon was used as a template.

Figures 2A, 2B:

Briefly, to generate the reporter system as shown in FIG. 1A, HIPK3 expression plasmids were first generated. To generate HIPK3 expression plasmids, portions of the human HIPK3 gene sequences were inserted into a pcDNA3.1(+) vector. A pcDNA3.1(+) vector is a mammalian expression vector with a human cytomegalovirus (CMV) promoter where the multiple cloning site (MCS) is in the forward (+) orientation. New vector cassettes were constructed using the naturally occurring HIPK3 intron sequences by cloning them into a plasmid backbone separated by a multiple cloning site. FIG. 2A shows the HIPK3 intron sequences (SEQ ID NO: 1 and SEQ ID NO: 2) used in the new vector cassettes. A cassette containing an IRES (e.g., EMCV, Polio, KSHV, or HCV) and split GFP was cloned between the intron sequences. The split GFP cassette used in the Examples herein was derived from a circGFP plasmid using methods similar to those disclosed in Wang and Wang, R N A. 2015; 21(2):172-179, the disclosure of which is incorporated herein in its entirety.

In addition to reporter systems using naturally occurring HIPK3 intron sequences, other reporter systems were generated using similar methods to those described above except for using Laccase2 and ZKSCAN1 intron sequences. FIGS. 2B and 2C show the Laccase2 ((SEQ ID NO: 6 and SEQ ID NO: 7) and ZKSCAN1 (SEQ ID NO: 11 and SEQ ID NO: 12) intron sequences, respectively, used in these new vector cassettes. Sequences for reporter systems using HIPK3, Laccase2 and ZKSCAN1 intron sequences are provided in Table 3.

TABLE 3

| DESCRIPTION | SEQUENCE | SEQ ID NO: |
|---|---|---|
| HIPK3 Left intron | GCCTCAGCCTCTCAAAGTGCTAGGATTACAGGGATC TATACTTTTCTTTTGAGGGAAAATGTTGGCACCGTTT CTAGGGCATATTGGCCATTTCAGCTTCTCAGTAAATA | 1 |

TABLE 3-continued

| DESCRIPTION | SEQUENCE | SEQ ID NO: |
|---|---|---|
| | TTTGTTAAGTAATTAAATGCACTTGATTCTTTATTCT TAGCCTTTTAACGCAATACTCAGAATAGCTGAAGCA CCAATTAACTGAAATGGAGATATTATAAAGATAGTT ATCTTCTCCAAGGGAAAAAATCATCTTCATGGAAAT TAATTACTTTTTTACAAATTGTGAATTTGACCCTTAA GAGTTTTCTTCCTGATATTTAAAATTGAAAAAAAAA TTGTTGACATTAATATTTCTTCTTTCCTTTTTTTTCTTT TCCTTTTTTTTTTTTTTTTGCAG | |
| HIPK3 Right intron | GTAGGTAACAACTCCATACTTTTTGGTTGTTTATTAA TGTGAAATTTCTGCTAAATGAAATACTTTTGTGTGTG TTTGTGGTAGAAGAGACCACTTCAGTTAAATAAGGA AATCAAGAGAGGATCAATTTAGGTTCGTTTTAAAGA GATTAAAAAAAATCAAGACATAAAATCTACCCAAGC AGGATAGAAATCTCCACTGCAAAGTTCCATGCCAAA GACATCTGGTTATTTTTATTTTTAATGGAAGACTTGA AGGAATGATAGGTGATTAATAATGATCAAACAGAA GTCTTTAAATGTTGGAAAGTATTTACATTAATCTTTG TATATATCATTGGGCATTTTAGCACTTGAGAGAAAT AGTTTATTAAAGATATAATCAATCATATGTAACTGA ACATTTAGAAAAATTATATACAGGTTTGAGTAGCCC TTATCTGAAACTTTTGGGGCCAGAAGTGTTTTGGATT CCAGATTTTTCCGGATTTTGGAATATTTGCACTGCCA ACTAGTTAAGCACCCCCAAATTTGAAAATTCGTTTCC TTTGAGTGTCATGTCAATGCCCAAAAAGTTTCAGAT ATTTGGATTTGAGATGCTCAACCTGTATAAGGATTC AGAAAGTTATTCTGATTAATGATTTTAAGATTCAGAT ATACAATAATCCCAGCAACTTGGGAGGCTGAGGCAG GAGAATCACTTGAACCCAGGAGATGGAGGTTGCAGT GAGCCGAGATCATGCCATTGCACTCCA | 2 |
| Alu Element (or complementary region) of Left intron of HIPK3 | GCCTCAGCCTCTCAAAGTGCTAGGATTACAGGGAT | 3 |
| Alu Element (or complementary region) of Right intron of HIPK3 | TAATCCCAGCAACTTGGGAGGCTGAGGCAGGAGAAT CACTTGAACCCAGGAGATGGAGGTTGCAGTGAGCCG AGATCATGCCATTGCACTCCA | 4 |
| Poly-pyrimidine tract of Left intron of HIPK3 | TTTCTTCTTTCCTTTTTTTTCTTTTCCTTTTTTTTTTTT TTTT | 5 |
| Splice Site of HIPK3 | CAGGTAGGT | n/a |
| Laccase2 Left intron | TCATTGAGAAATGACTGAGTTCCGGTGCTCTCAAGT CATTGATCTTTGTCGACTTTTATTTGGTCTCTGTAAT AACGACTTCAAAAACATTAAATTCTGTTGCGAAGCC AGTAAGCTACAAAAAGAAAAAACAAGAGAGAATGC TATAGTCGTATAGTATAGTTTCCCGACTATCTGATAC CCATTACTTATCTAGGGGGAATGCGAACCCAAAATT TTATCAGTTTTCTCGGATATCGATAGATATTGGGGAA TAAATTTAAATAAATAAATTTTGGGCGGGTTTAGGG CGTGGCAAAAAGTTTTTTGGCAAATCGCTAGAAATT TACAAGACTTATAAAATTATGAAAAAATACAACAAA ATTTTAAACACGTGGGCGTGACAGTTTTGGACGGTT TTAGGGCGTTAGAGTAGGCGAGGACAGGGTTACATC GACTAGGCTTTGATCCTGATCAAGAATATATATACTT TATACCGCTTCCTTCTACATGTTACCTATTTTTCAAC GAATCTAGTATACCTTTTTACTGTACGATTTATGGGT ATAATAATAAGCTAAATCGAGACTAAGTTTTATTGT TATATATATTTTTTTTATTTTATGCAG | 6 |
| Laccase2 Right intron | GTAAGTATTCAAAATTCCAAAATTTTTTACTAGAAAT ATTCGATTTTTTAATAGGCAGTTTCTATACTATTGTA TACTATTGTAGATTCGTTGAAAAGTATGTAACAGGA AGAATAAAGCATTTCCGACCATGTAAAGTATATATA TTCTTAATAAGGATCAATAGCCGAGTCGATCTCGCC ATGTCCGTCTGTCTTATTATTTTATTACCGCCGAGAC ATCAGGAACTATAAAAGCTAGAAGGATGAGTTTTAG CATACAGATTCTAGAGACAAGGACGCAGAGCAAGTT TGTTGATCCATGCTGCCACGCTTTAACTTTCTCAAAT TGCCCAAAACTGCCATGCCCACATTTTTTGAACTATTT | 7 |

TABLE 3-continued

| DESCRIPTION | SEQUENCE | SEQ ID NO: |
|---|---|---|
| | TCGAAATTTTTTCATAATTGTATTACTCGTGTAAATT TCCATCAATTTGCCAAAAAACTTTTTGTCACGCGTTA ACGCCCTAAAGCCGCCAATTTGGTCACGCCCACACT ATTGAACAATTATCAAATTTTTTCTCATTTTATTCCC CAATATCTATCGATATCCCCGATTATGAAATTATTAA ATTTCGCGTTCGCATTCACACTAGCTGAGTAACGAG TATCTGATAGTTGGGGAAATCGACTTATTTTTTATAT ACAATGAAAATGAATTTAATCATATGAATATCGATT ATAGCTTTTTATTTAATATGAATATTTATTTGGGCTT AAGGTGTAACCTCCTCGACATAAGACTCACATGGCG CAGGCACATTGAAGACAAAAATACTCATTGTCGGGT CTCGCACCCTCCAGCAGCACCTAAAATTATGTCTTCA ATTATTGCCAACATTGGAGACACAATTAGTCTGTGG CACCTCAG | |
| Alu Element (or complementary region) of Left intron of Laccase2 | TTCCCGACTATCTGATACCCATTACTTATCTAGGGGG AATGCGAACCCAAAATTTTATCAGTTTTCTCGGATAT CGATAGATATTGGGGAATAAATTTAAATAAATAAAT TTTGGGCGGGTTTAGGGCGTGGCAAAAAGTTTTTTG GCAAATCGCTAGAAATTTACAAGACTTATAAAATTA TGAAAAAATACAACAAAATTTTAAACACGTGGGCGT GACAGTTTTGG | 8 |
| Alu Element (or complementary region) of Right intron of Laccase2 | CAAAACTGCCATGCCCACATTTTTGAACTATTTTCGA AATTTTTTCATAATTGTATTACTCGTGTAAATTTCCA TCAATTTGCCAAAAAACTTTTTGTCACGCGTTAACGC CCTAAAGCCGCCAATTTGGTCACGCCCACACTATTG AACAATTATCAAATTTTTTCTCATTTTATTCCCCAAT ATCTATCGATATCCCCGATTATGAAATTATTAAATTT CGCGTTCGCATTCACACTAGCTGAGTAACGAGTATC TGATAGTTGGGGAA | 9 |
| Poly-pyrimidine tract of Left intron of Laccase2 | TTTTTTTTATTTTAT | 10 |
| Splice Site of Laccase2 | CAGGTAAGT | n/a |
| ZKSCAN1 Left intron | AGTGACAGTGGAGATTGTACAGTTTTTTCCTCGATTT GTCAGGATTTTTTTTTTTTTGACGGAGTTTAACTTCTT GTCTCCCAGGTAGGAAGTGCAGTGGCGTAATCTCGG CTCACTACAACCTCCACCTCCTGGGTTCAAGCGTTTC TCCTGCCTCAGCTTTCCGAGTAGCTGGGATTACAGG CGCCTGCCACCATGCCCTGCTGACTTTTGTATTTTTA GTAGAGACGGGGTTTCACCATGTTGGCCAGGCTGGT CTTGAACTCCTGACCGCAGGCGATTGGCCTGCCTCG GCCTCCCAAAGTGCTGAGATTACAGGCGTGAGCCAC CACCCCCGGCCTCAGGAGCGTTCTGATAGTGCCTCG ATGTGCTGCCTCCTATAAAGTGTTAGCAGCACAGAT CACTTTTTGTAAAGGTACGTACTAATGACTTTTTTTT TATACTTCAG | 11 |
| ZKSCAN1 Right intron | GTAAGAAGCAAGGTTTCATTTAGGGGAAGGGAAAT GATTCAGGACGAGAGTCTTTGTGCTGCTGAGTGCCT GTGATGAAGAAGCATGTTAGTCCTGGGCAACGTAGC GAGACCCCATCTCTACAAAAAATAGAAAAATTAGCC AGGTATAGTGGCGCACACCTGTGATTCCAGCTACGC AGGAGGCTGAGGTGGGAGGATTGCTTGAGCCCAGG AGGTTGAGGCTGCAGTGAGCTGTAATCATGCCACTA CTCCAACCTGGGCAACACAGCAAGGACCCTGTCTCA AAAGCTACTTACAGAAAGAATTAGGCTCGGCACGG TAGCTCACACCTGTAATCCCAGCACTTTGGGAGGCT GAGGCGGGCAGATCACTTGAGGTCAGGAGTTTGAGA CCAGCCTGGCCAACATGGTGAAACCTTGTCTCTACT AAAAATATGAAAATTAGCCAGGCATGGTGGCACATT CCTGTAATCCCAGCTACTCGGGAGGCTGAGGCAGGA GAATCACTTGAACCCAGGAGGTGGAGGTTGCAGTAA GCCGAGATCGTACCACTGTGCTCTAGCCTTGGTGAC AGAGCGAGACTGTCTTAAAAAAAAAAAAAAAAAAA AAAGAATTAATTAAAAATTTAAAAAAAAATGAAAA AAAGCTGCATGCTTGTTTTTTGTTTTTAGTTATTCTAC ATTGTTGTCATTATTACCAAATATTGGGGAAAATAC AACTTACAGACCAATCTCAGGAGTTAAATGTTACTA CGAAGGCAAATGAACTATGCGTAATGAACCTGGTAG GCATTA | 12 |

TABLE 3-continued

| DESCRIPTION | SEQUENCE | SEQ ID NO: |
|---|---|---|
| Alu Element (or complementary region) of Left intron of ZKSCAN1 | AGGATTTTTTTTTTTTTGACGGAGTTTAACTTCTTGTC TCCCAGGTAGGAAGTGCAGTGGCGTAATCTCGGCTC ACTACAACCTCCACCTCCTGGGTTCAAGCGTTTCTCC TGCCTCAGCTTTCCGAGTAGCTGGGATTACAGGCGC CTGCCACCATGCCCTGCTGACTTTTGTATTTTTAGTA GAGACGGGGTTTCACCATGTTGGCCAGGCTGGTCTT GAACTCCTGACCGCAGGCGATTGGCCTGCCTCGGCC TCCCAAAGTGCTGAGATTACAGGCGTGAGCCACCAC CCCCGGCCTCAGGAGCGTTCTGATAGTGCCTCGA | 13 |
| Alu Element (or complementary region) of Right intron of ZKSCAN1 | GCACGGTAGCTCACACCTGTAATCCCAGCACTTTGG GAGGCTGAGGCGGGCAGATCACTTGAGGTCAGGAG TTTGAGACCAGCCTGGCCAACATGGTGAAACCTTGT CTCTACTAAAAATATGAAAATTAGCCAGGCATGGTG GCACATTCCTGTAATCCCAGCTACTCGGGAGGCTGA GGCAGGAGAATCACTTGAACCCAGGAGGTGGAGGT TGCAGTAAGCCGAGATCGTACCACTGTGCTCTAGCC TTGGTGACAGAGCGAGACTGTCTTAAAAAAAA | 14 |
| Poly-pyrimidine tract of Left intron of ZKSCAN1 | TTTTTTTTTATACTT | 15 |
| Splice Site of ZKSCAN1 | CAGGTAAGA | n/a |

As shown in FIG. 1A, the resulting construct contained portions of introns from the HIPK3 gene placed around a split GFP reporter exon. Inverted Alu repeats in the introns interacted, allowed for backsplicing to occur, forming a circRNA. The presence of an IRES sequence drove translation, leading to GFP protein expression.

To probe the impact of spacing in the introns, the distance between each Alu element and the splice site was artificially increased. Random inserts ranging from 100 to 1,500 nt were designed with nucleotide content (e.g., G/C) similar to the content of the HIPK3 introns but devoid of any strong predicted secondary structure. Once insert design met this criteria, the 1.5 kb randomized sequences for the left and right introns were then synthesized. Sequences were inserted into the introns or exons using PCR and restriction cloning. When necessary, site-directed mutagenesis was used to make 1-2 nt changes to create a restriction enzyme site.

The first random insert was inserted into the "left" intron (upstream of the splice acceptor site) at a site ~100 nt from the splice acceptor (FIG. 11B). Constructs were transfected into HEK293 (Human Embryonic Kidney) cells. Briefly, cells were seeded into 6-well plates and transfected at ~70% confluency. Transfections were performed using 2.5 µg of plasmid DNA (test constructs were equimolar, with mass equalized using empty vector) and 12.5 µL of 1 mg/mL PEI-MAX 40,000. Four days post-transfection, the cells were harvested and assayed for expression of GFP protein using western blotting analysis and for circRNA expression using northern blotting analysis.

Figure 1C:
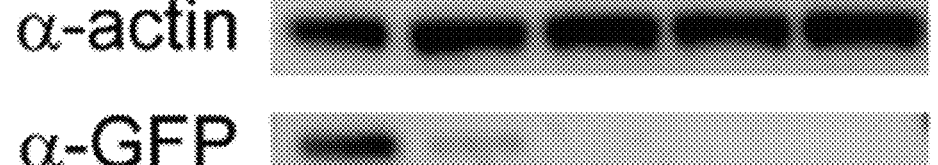
Figure 1D:
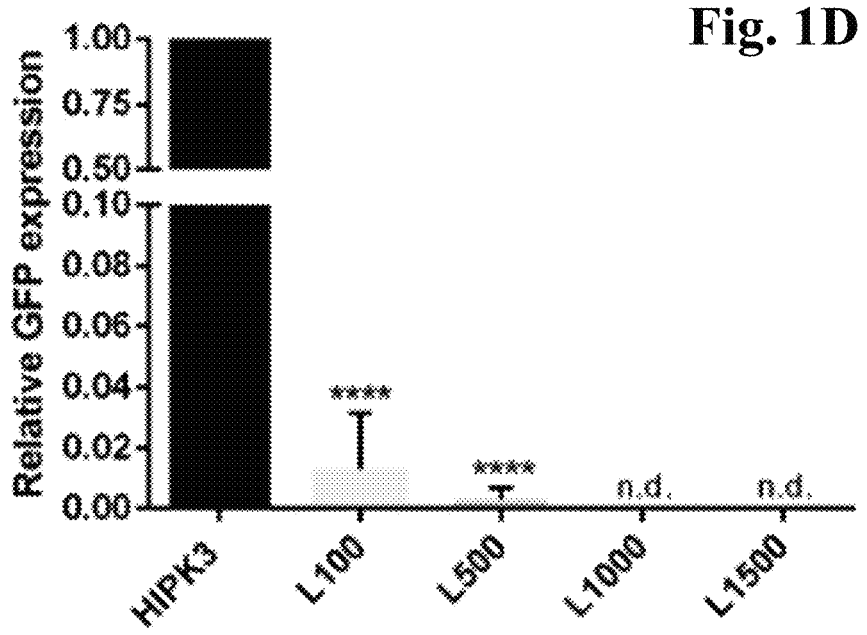
Figures 1E, 1F:
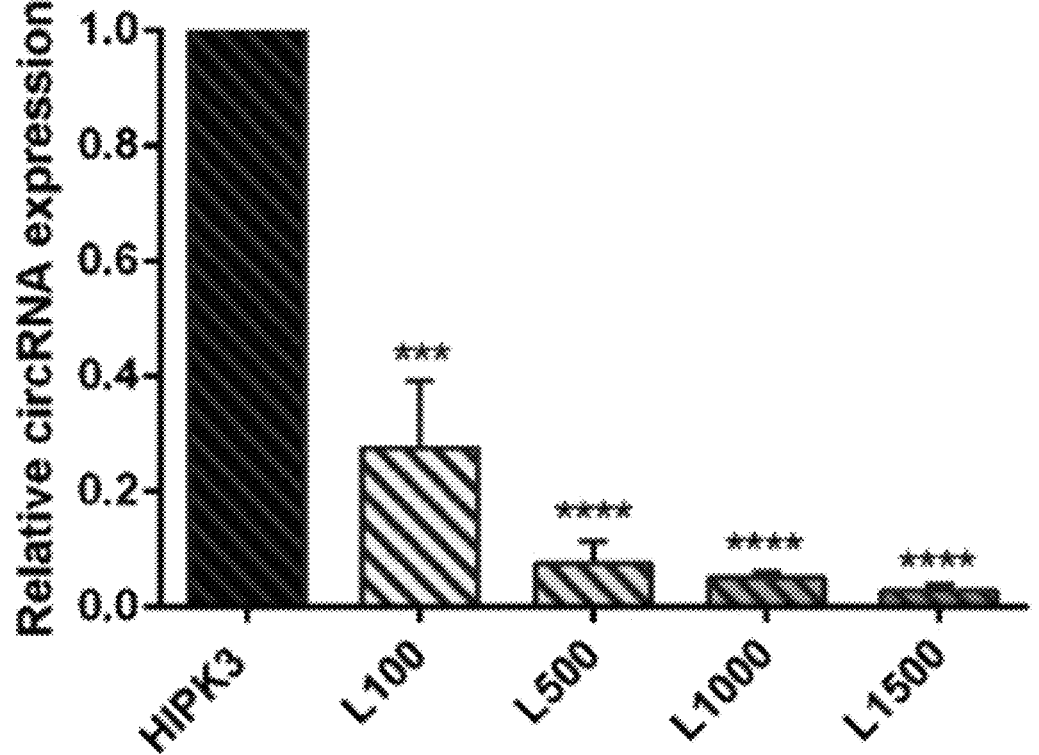

The insertion of additional distance was highly detrimental, as seen from western blots of GFP protein (FIGS. 1C and 1D) and northern blots of the circRNA (FIGS. 1E and 1F). Insertion of only 100 nt lowered the circRNA formation by ~5-fold, whereas greater distances effectively ablated circRNA formation.

Figures 3A, 3B, 3C, 3D, 3E:
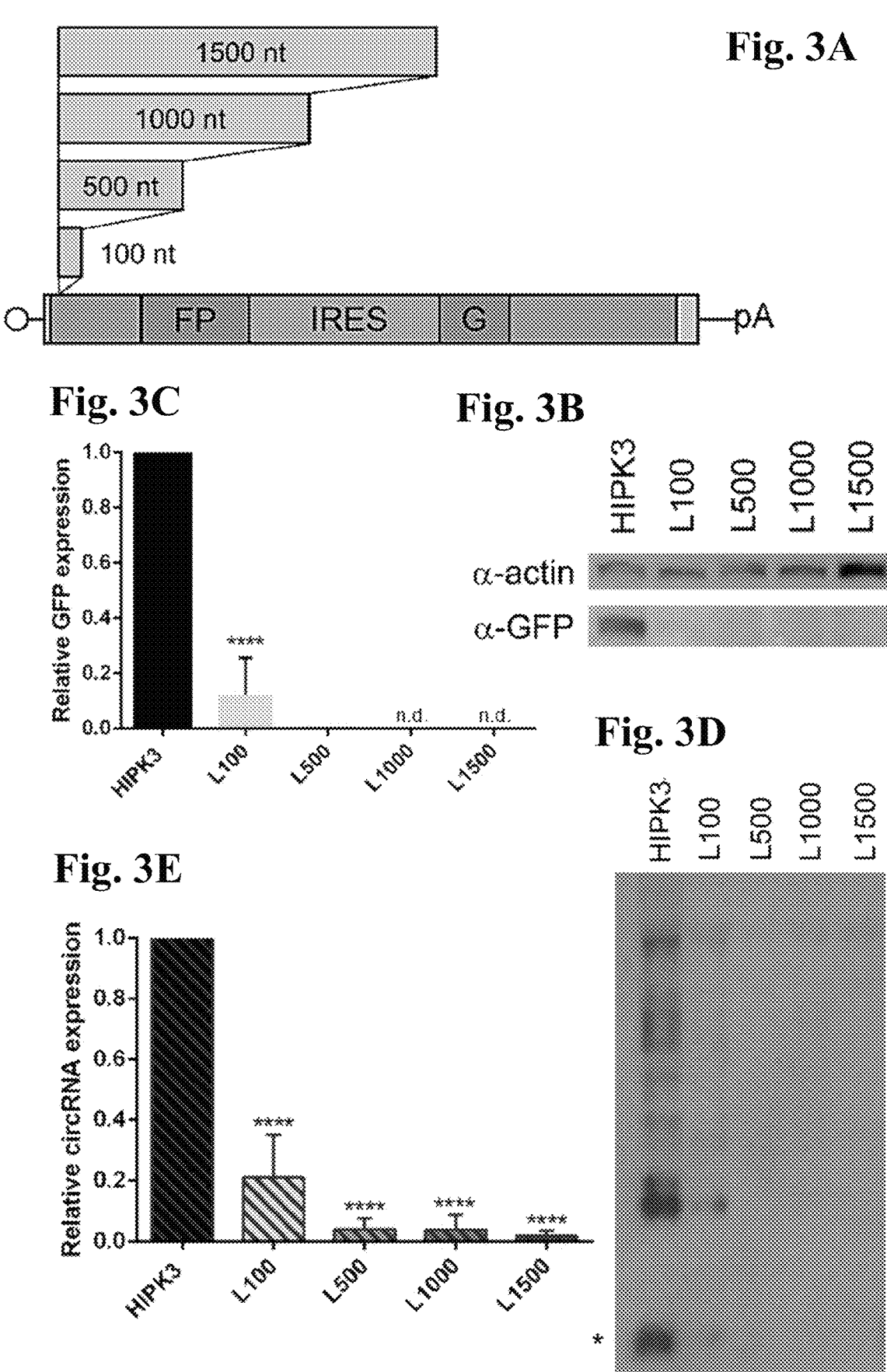
FIGS. 3A-3E are schematics, images, and graphs showing that increased distance between the left Alu element and splice acceptor site was harmful even when inserted distal to the splice site in accordance with embodiments of the present disclosure.

Given that the HIPK3 splice acceptor has a large poly-pyrimidine tract (SEQ ID NO: 5) and to control for a possible impact on the branch point environment, a second series of constructs was created in which the additional sequences were inserted distal to the splice junction and proximal to the Alu element (FIG. 3A). This second set behaved virtually identically, with insertion of 100 nt or more greatly reducing GFP expression (FIGS. 3B and 3C) and circRNA formation (FIGS. 3D and 3E).

Figure 1G:
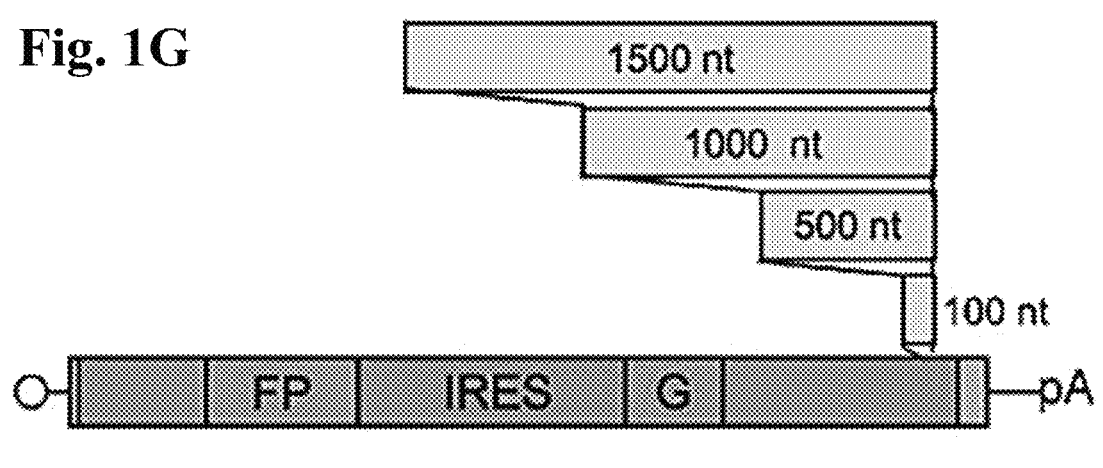
FIGS. 1G-1K are schematics, images, and graphs showing sequence insertions into the right HIPK3 intron.
Figure 1H:
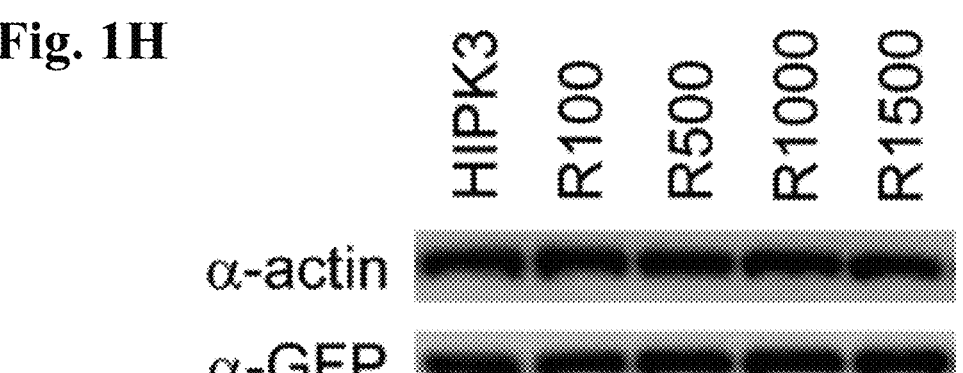
Figure 1I:
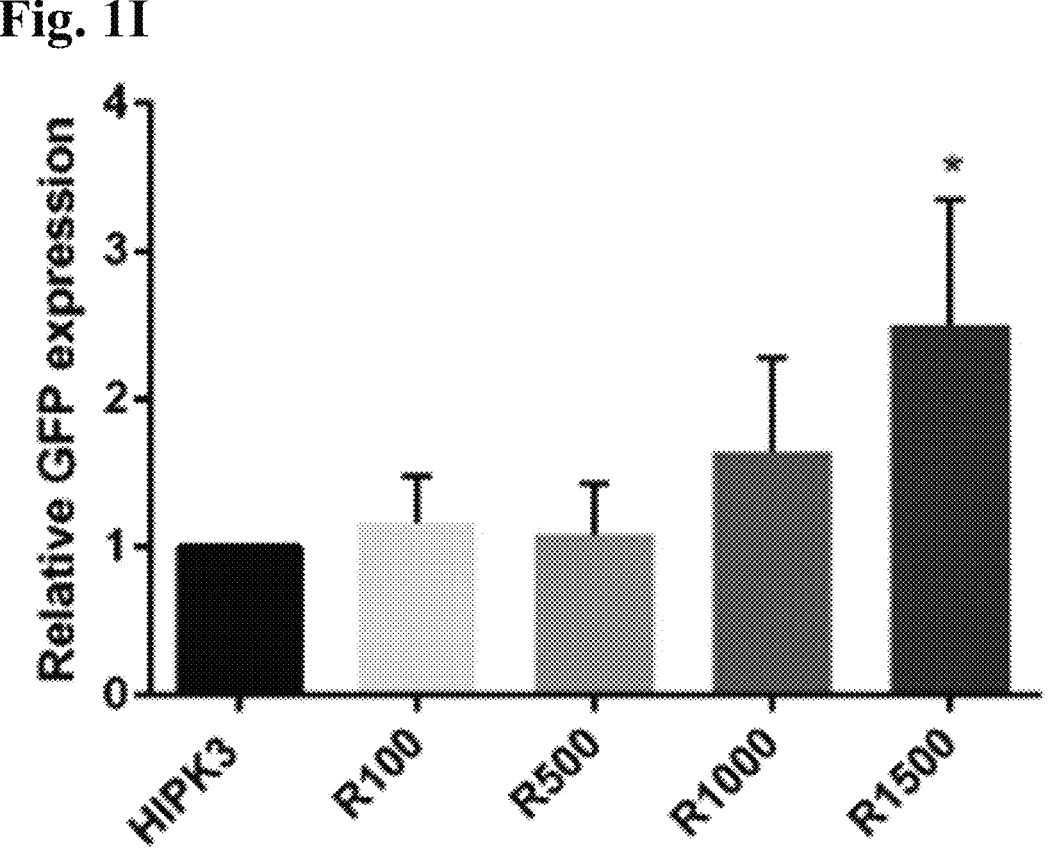
Figure 1J:
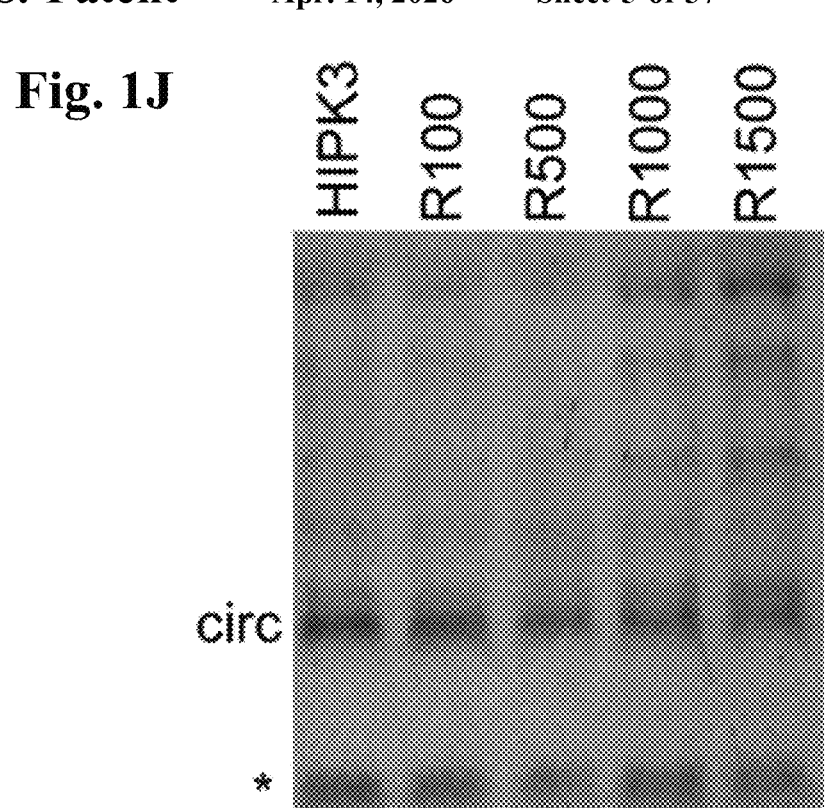
Figure 1K:
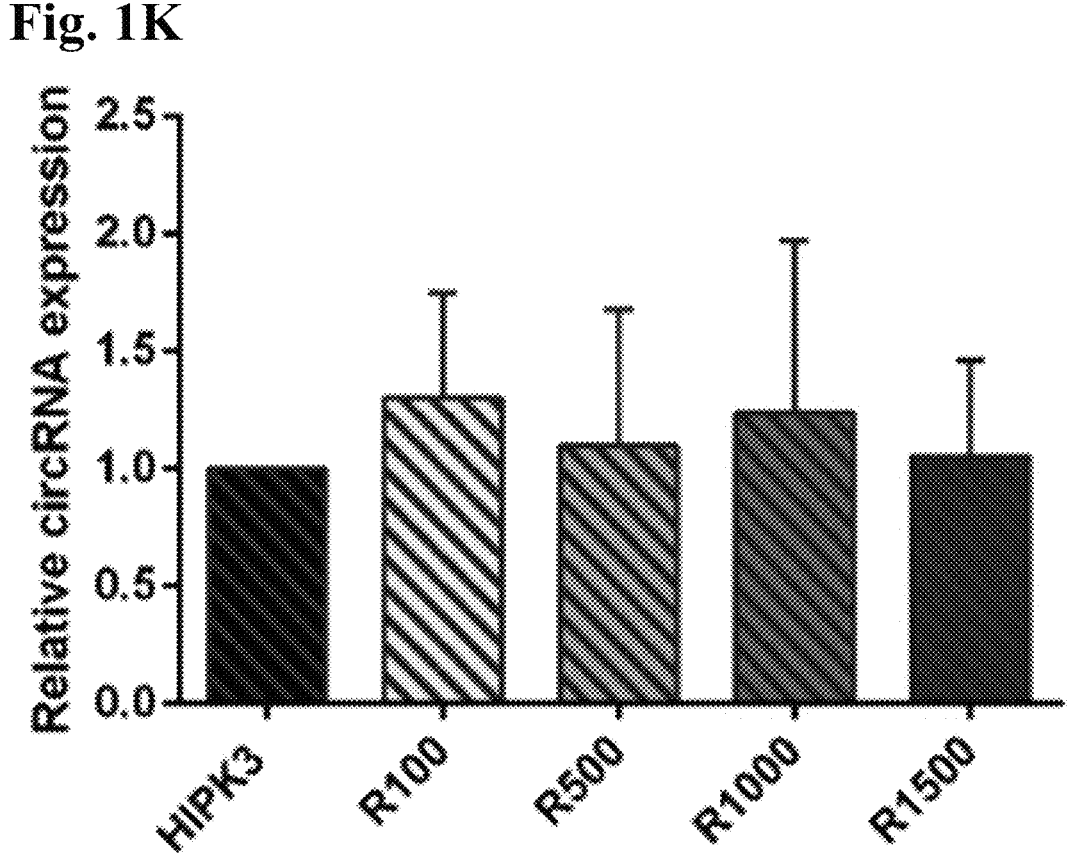

Insertions in the "right" intron (downstream of the splice donor site) were also generated as shown in FIG. 1G. Surprisingly, the effect of right insertions was distinct from the left intron insertions, with sequences up to 1.5 kb in length showing no effect on GFP expression (FIGS. 1H and 1I) or circRNA formation (FIGS. 1J and 1K). Different RNA concatemers formed in the case of the original HIPK3 intron were also observed in these constructs with inserts in the right intron. Notably, these additional bands/molecular entities were later resolved and found to be dependent on other elements such as the IRES, as described in other Examples herein.

Next, the randomized insert was replaced with a sequence encoding a *Drosophila* tRNA:Tyr$_{GUA}$ gene carrying an intron containing the noncoding RNA-based fluorescent aptamer Broccoli as provided in Table 4.

TABLE 4

| DESCRIPTION | SEQUENCE | SEQ ID NO: |
|---|---|---|
| TricY Sequence | CCTTCGATAGCTCAGTTGGTAGAGC GGAGGACTGTAGGCGGCCGCGAGAC GGTCGGGTCCAGATATTCGTATCTG TCGAGTAGAGTGTGGGCTCGTGGCC GCGGAGGTATCCTTAGGTCGCTGGT TCGAATCCGGCTCGGAGGA | 16 |
| Left Intron of TricY Sequence | CCTTCGATAGCTCAGTTGGTAGAGC GGAGGACTGTAG | 17 |
| Right Intron of TricY Sequence | GAGGTATCCTTAGGTCGCTGGTTCG AATCCGGCTCGGAGGA | 18 |
| Broccoli Aptamer of TricY Sequence | GAGACGGTCGGGTCCAGATATTCGT ATCTGTCGAGTAGAGTGTGGGCTC | 19 |

Figure 1L:
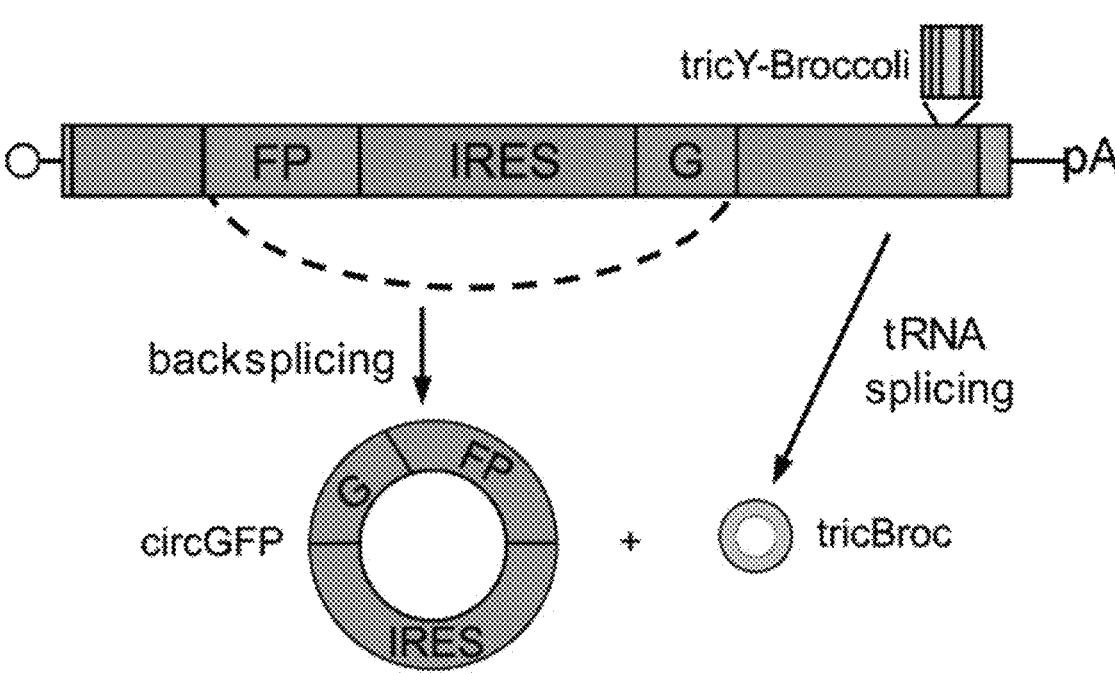
Figure 1M:
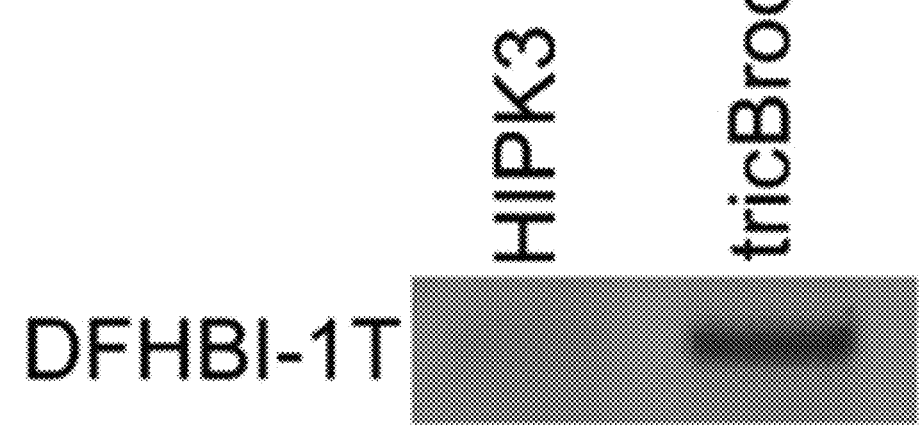

The resulting construct, shown in FIG. 1L, independently produced both a GFP circRNA and a circular Broccoli tricRNA (tricY-Broccoli). Robust tricY-Broccoli expression was observed using an in-gel assay (FIG. 1M). In brief, 5 g of RNA was resuspended in denaturing buffer (67% deionized formamide, 6.7% formaldehyde, 1×MOPS running buffer), incubated at 65° C. for 7 minutes, and cooled on ice. Denatured samples were separated on a 10% Trisborate/EDTA (TBE)-urea gel run at 300 V. The gel was washed three times in water and then stained for 30 minutes in DFHBI-1T fluorescent probe staining solution (40 mM HEPES pH 7.4, 100 mM KCl, 1 mM MgCl$_2$, 10 M DFHBI-1T). The stained gel was imaged with an Amersham Typhoon (GE Healthcare), using the 488 excitation/526 emission setting.

Figures 1N, 1O, 1P, 1Q:
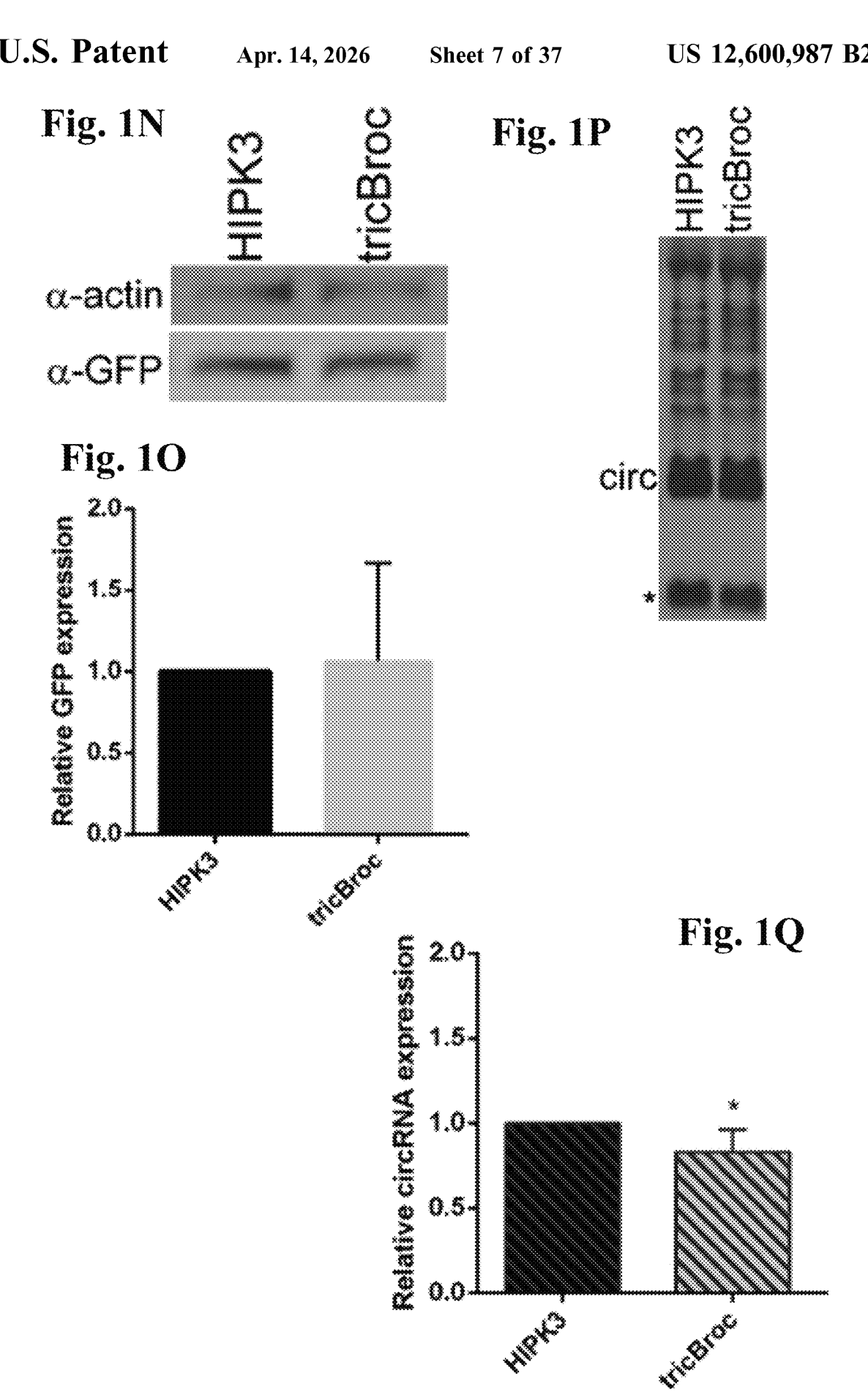

Western and northern blot analyses confirmed that tricRNA formation did not affect GFP protein (FIGS. 1N and 1O) or circRNA levels (FIGS. 1P and 1Q). Thus, not only can the distance between the splice donor and the Alu element be increased without effect, but an additional functional RNA element can be inserted in the intronic region.

Example 2. Synthetic Intronic Sequences Increase circRNA Expression

Next, the effect of decreasing the distance between the Alu element and splice site was examined by deleting intronic sequences of the constructs described in Example 1. Examples of HIPK3, Laccase2, and ZKSCAN1 introns having deleted regions are provided in Table 5.

TABLE 5

| DESCRIPTION | SEQUENCE | SEQ ID NO: |
|---|---|---|
| Right intron of HIPK3 with Deletions | GTAGGTAACCCAACTAGTTAAGCACCCCCAAATTT GAAAATTCGTTTCCTTTGAGTGTCATGTCAATGCC CAAAAAGTTTCAGATATTTGGATTTGAGATGCTCA ACCTGTATAAGGATTCAGAAAGTTATTCTGATTAA TGATTTTAAGATTCAGATATACAATAATCCCAGCA ACTTGGGAGGCTGAGGCAGGAGAATCACTTGAAC CCAGGAGATGGAGGTTGCAGTGAGCCGAGATCAT GCCATTGCACTCCA | 20 |
| Left intron of HIPK3 with Deletions | GCCTCAGCCTCTCAAAGTGCTAGGATTACAGGGA TCTATACTACAAATTGTGAATTTGACCCTTAAGAG TTTTCTTCCTGATATTTAAAATTGAAAAAAAAATT GTTGACATTAATATTTCTTCTTTCCTTTTTTTTCTTT TCCTTTTTTTTTTTTTTTTTGCAG | 21 |
| Right intron of ZKSCAN1 with Deletions | GTAAGAAGCAGGAGGCTGAGGTGGGAGGATTGCT TGAGCCCAGGAGGTTGAGGCTGCAGTGAGCTGTA ATCATGCCACTACTCCAACCTGGGCAACACAGCA AGGACCCTGTCTCAAAAGCTACTTACAGAAAGA ATTAGGCTCGGCACGGTAGCTCACACCTGTAATCC CAGCACTTTGGGAGGCTGAGGCGGGCAGATCACT TGAGGTCAGGAGTTTGAGACCAGCCTGGCCAACA TGGTGAAACCTTGTCTCTACTAAAAATATGAAAAT TAGCCAGGCATGGTGGCACATTCCTGTAATCCCAG CTACTCGGGAGGCTGAGGCAGGAGAATCACTTGA ACCCAGGAGGTGGAGGTTGCAGTGAAGCCGAGATC GTACCACTGTGCTCTAGCCTTGGTGACAGAGCGA GACTGTCTTAAAAAAAAAAAAAAAAAAAAAAGA ATTAATTAAAAATTTAAAAAAAAATGAAAAAAAG CTGCATGCTTGTTTTTTGTTTTTAGTTATTCTACAT TGTTGTCATTATTACCAAATATTGGGGAAAATACA ACTTACAGACCAATCTCAGGAGTTAAATGTTACTA CGAAGGCAAATGAACTATGCGTAATGAACCTGGT AGGCATTA | 22 |
| Left intron of ZKSCAN1 with Deletions | AGTGACAGTGGAGATTGTACAGTTTTTTCCTCGAT TTGTCAGGATTTTTTTTTTTTTTGACGGAGTTTAACT TCTTGTCTCCCAGGTAGGAAGTGCAGTGGCGTAAT CTCGGCTCACTACAACCTCCACCTCCTGGGTTCAA GCGTTTCTCCTGCCTCAGCTTTCCGAGTAGCTGGG ATTACAGGCGCCTGCCACCATGCCCTGCTGACTTT TGTATTTTTAGTAGAGACGGGGTTTCACCATGTTG GCCAGGCTGGTCTTGAACTCCTGACCGCAGGCGA TTGGCCTGCCTCGGCCTCCCAAAGTGCTGAGATTA CAGGCGTGAGCCACCACCCCCGGCCTCAGGAGCG TTCTGATAGTGCCTCGAACAGATCACTTTTTGTAA AGGTACGTACTAATGACTTTTTTTTTATACTTCAG | 23 |
| Right intron of Laccase2 with Deletions | GTAAGTATTCAAAAGCATTTCCGACCATGTAAAGT ATATATATTCTTAATAAGGATCAATAGCCGAGTCG ATCTCGCCATGTCCGTCTGTCTTATTATTTTATTAC CGCCGAGACATCAGGAACTATAAAAGCTAGAAGG ATGAGTTTTAGCATACAGATTCTAGAGACAAGGA CGCAGAGCAAGTTTGTTGATCCATGCTGCCACGCT TTAACTTTCTCAAATTGCCCAAAACTGCCATGCCC ACATTTTTGAACTATTTTCGAAATTTTTTCATAATT GTATTACTCGTGTAAATTTCCATCAATTTGCCAAA AAACTTTTTGTCACGCGTTAACGCCCTAAAGCCGC | 24 |

TABLE 5-continued

| DESCRIPTION | SEQUENCE | SEQ ID NO: |
|---|---|---|
| | CAATTTGGTCACGCCCACACTATTGAACAATTATC | |
| | AAATTTTTTCTCATTTTATTCCCCAATATCTATCGA | |
| | TATCCCCGATTATGAAATTATTAAATTTCGCGTTC | |
| | GCATTCACACTAGCTGAGTAACGAGTATCTGATA | |
| | GTTGGGGAAATCGACTTATTTTTTATATACAATGA | |
| | AAATGAATTTAATCATATGAATATCGATTATAGCT | |
| | TTTTATTTAATATGAATATTTATTTGGGCTTAAGGT | |
| | GTAACCTCCTCGACATAAGACTCACATGGCGCAG | |
| | GCACATTGAAGACAAAAATACTCATTGTCGGGTC | |
| | TCGCACCCTCCAGCAGCACCTAAAATTATGTCTTC | |
| | AATTATTGCCAACATTGGAGACACAATTAGTCTGT | |
| | GGCACCTCAG | |
| Left intron of Laccase2 with Deletions | TCATTGAGAAATGACTGAGTTCCGGTGCTCTCAAG | 25 |
| | TCATTGATCTTTGTCGACTTTTATTTGGTCTCTGTA | |
| | ATAACGACTTCAAAAACATTAAATTCTGTTGCGAA | |
| | GCCAGTAAGCTACAAAAAGAAAAAACAAGAGAG | |
| | AATGCTATAGTCGTATAGTATAGTTTCCCGACTAT | |
| | CTGATACCCATTACTTATCTAGGGGGAATGCGAAC | |
| | CCAAAATTTTATCAGTTTTCTCGGATATCGATAGA | |
| | TATTGGGGAATAAATTTAAATAAATAAATTTTGGG | |
| | CGGGTTTAGGGCGTGGCAAAAAGTTTTTTGGCAA | |
| | ATCGCTAGAAATTTACAAGACTTATAAAATTATGA | |
| | AAAAATACAACAAAATTTTAAACACGTGGGCGTG | |
| | ACAGTTTTGGACGGTTTTAGTATAATAATAAGCTA | |
| | AATCGAGACTAAGTTTTATTGTTATATATATTTTTT | |
| | TTATTTTATGCAG | |

Figures 4H, 4I, 4J, 4K:
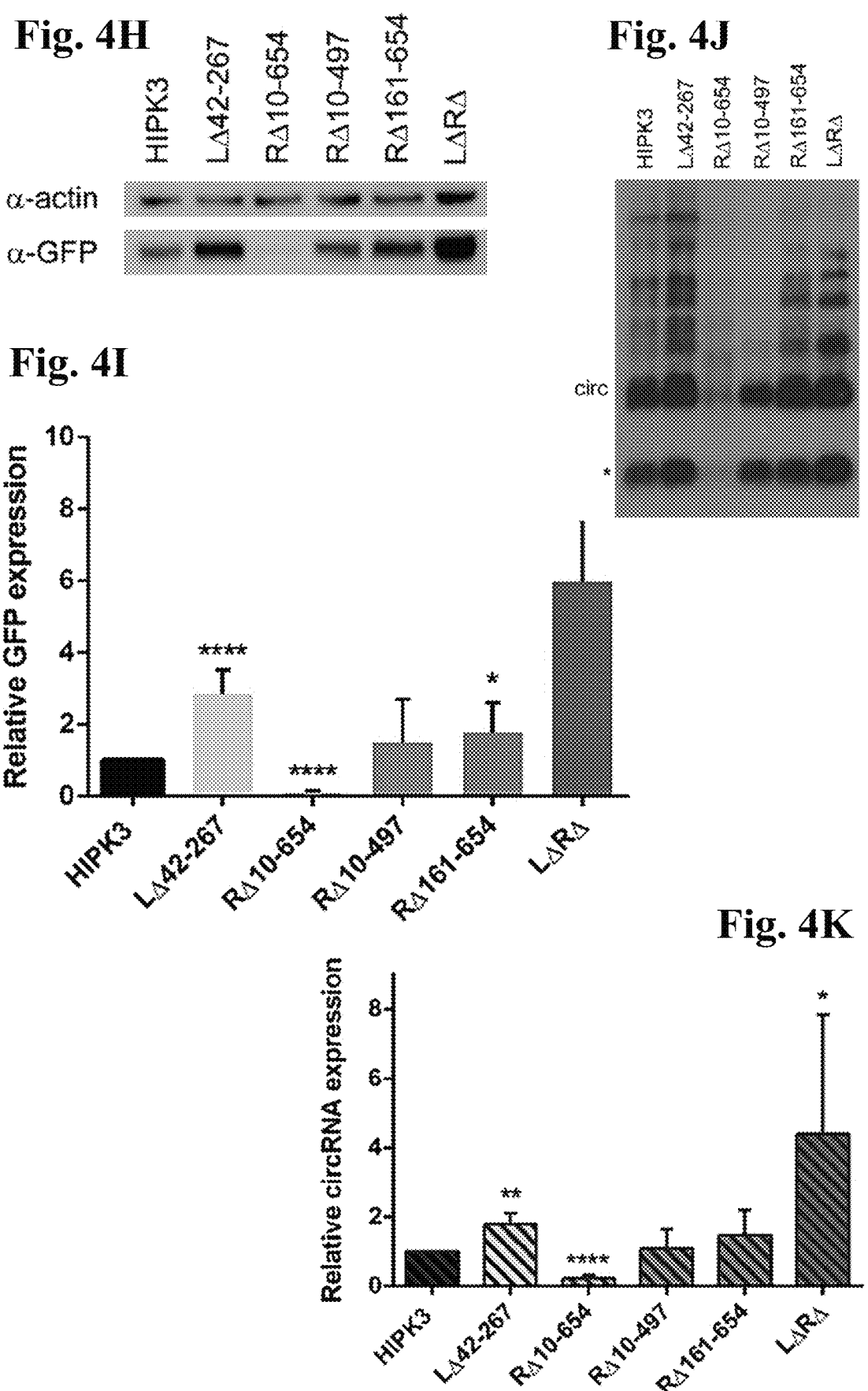
FIGS. 4H and 4I depict a western blot analysis for GFP expression where
FIGS. 4J and 4K depict a northern blot analysis probing for GFP RNA where

As disclosed in Example 1, the HIPK3 splice acceptor has a large poly-pyrimidine tract; therefore, ~125 nt proximal to the splice junction was preserved to create the LA42-267 construct. The right intron of HIPK3 had a full deletion (RΔ10-654) and two smaller deletions (RΔ10-497 and RΔ161-654), both of which preserve ~150 nt distance (FIG. 4A, deletions numbered from the start of their respective introns). Constructs were transfected into HEK293 cells and expression was assayed at 4 days post-transfection to assess the ability of these modified introns to support circRNA formation and translation by GFP fluorescence (FIGS. 4B-4G), western blot (FIGS. 4H and 4I), and northern blot (FIGS. 4J and 4K).

In brief, cells were imaged 4 days post-transfection using an EVOS FL epifluorescence cell imaging system equipped with the GFP light cube (excitation 470 nm, emission 510 nm) or the Texas Red light cube (excitation 585 nm, emission 624 nm) to detect GFP fluorescence. Like the methods of Example 1, cells were harvested from the plate and the resulting cell suspension was separated into two tubes and centrifuged at 300×g for 4 minutes at 4° C. Cell pellets were suspended in either 1× Passive Lysis Buffer or TRIzol Reagent placed on a rocker for 10 min at 4° C., and then stored at −80° C. prior to use. Lysates in Passive Lysis Buffer were centrifuged for 5 min at 16,000×g at 4° C. to remove cell debris prior to freezing. Lysates stored in Passive Lysis Buffer were processed for western blotting analysis and lysates stored in TRIzol Reagent were processed for northern blotting analysis.

The LΔ42-267 showed a ~2-fold higher GFP and circRNA expression in comparison to the original construct (FIGS. 4B-4K). The large RΔ10-654 deletion, which places the Alu element within 20 nt of the splice junction, reduced circularization efficiency drastically. However, the smaller deletions were tolerated without impacting circRNA biogenesis or GFP expression. Note that both smaller deletions splice equally well, indicating a sequence-independent effect. The upstream LΔ42-267 and downstream RΔ10-497 deletions were then combined to create the minimal LΔRΔ intronic elements. The combination of deletions led to a synergistic effect, increasing GFP expression and circRNA levels by ~5-fold (FIGS. 4B-4K). Deletion of either the left or right Alu regions (FIG. 4L) abrogated GFP expression (FIGS. 4M and 4N) and circRNA formation (FIGS. 4O and 4P), confirming the necessity of Alu elements in the system.

The HIPK3 and the modified HIPK3 constructs (e.g., L100, R1500, LΔ42-267, RΔ10-497 and LΔRΔ) were transfected into U87 glioblastoma and Huh7 hepatocarcinoma cell lines. Four days post-transfection, U87 and Huh7 cells were harvested and processed for western and norther blotting analysis as described above. GFP expression (FIGS. 5A and 5B) and circRNA expression (FIGS. 5C and 5D) in U87 cells and GFP expression (FIGS. 5E and 5F) and circRNA expression (FIGS. 5G and 5H) in Huh7 cells showed similar results to those observed in HEK293 cells as detailed above. The similar results were observed in HEK293, U87 glioblastoma and Huh7 hepatocarcinoma cell lines indicated that regulation of backsplicing was conserved across diverse cell types.

Example 3. Intronic Spacing Effects on circRNA Formation are Conserved

To ascertain whether the conclusions generated from the HIPK3-derived introns apply more generally, experiments described in Examples 1 and 2 were repeated with reporters driven by two different intron pairs derived from the human ZKSCAN1 gene or the *Drosophila melanogaster* Laccase2 gene (FIGS. 2B and 2C; Table 3). Three insertions were created in each intron pair (L100, L500, and R1500) (FIGS. 6A (ZKSCAN1) and 6F (Laccase2)). In both cases, insertions in the left intron decreased circRNA expression (FIGS. 6D-6E (ZKSCAN1) and 6I-6J (Laccase2)) and GFP expression (FIGS. 6B-6C (ZKSCAN1) and 6G-6H (Laccase2)). Insertion into the right Laccase2 intron did not change on GFP (FIGS. 6G-6H) or circRNA expression (FIGS. 6I-6J).

Figures 6A, 6B, 6C, 6D, 6E:
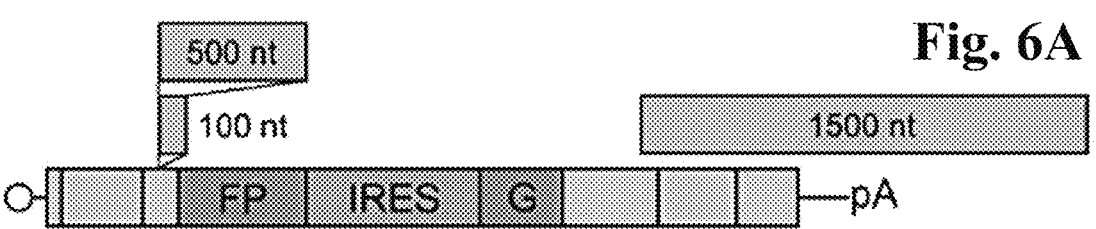
Figures 6F, 6G, 6H, 6I, 6J:
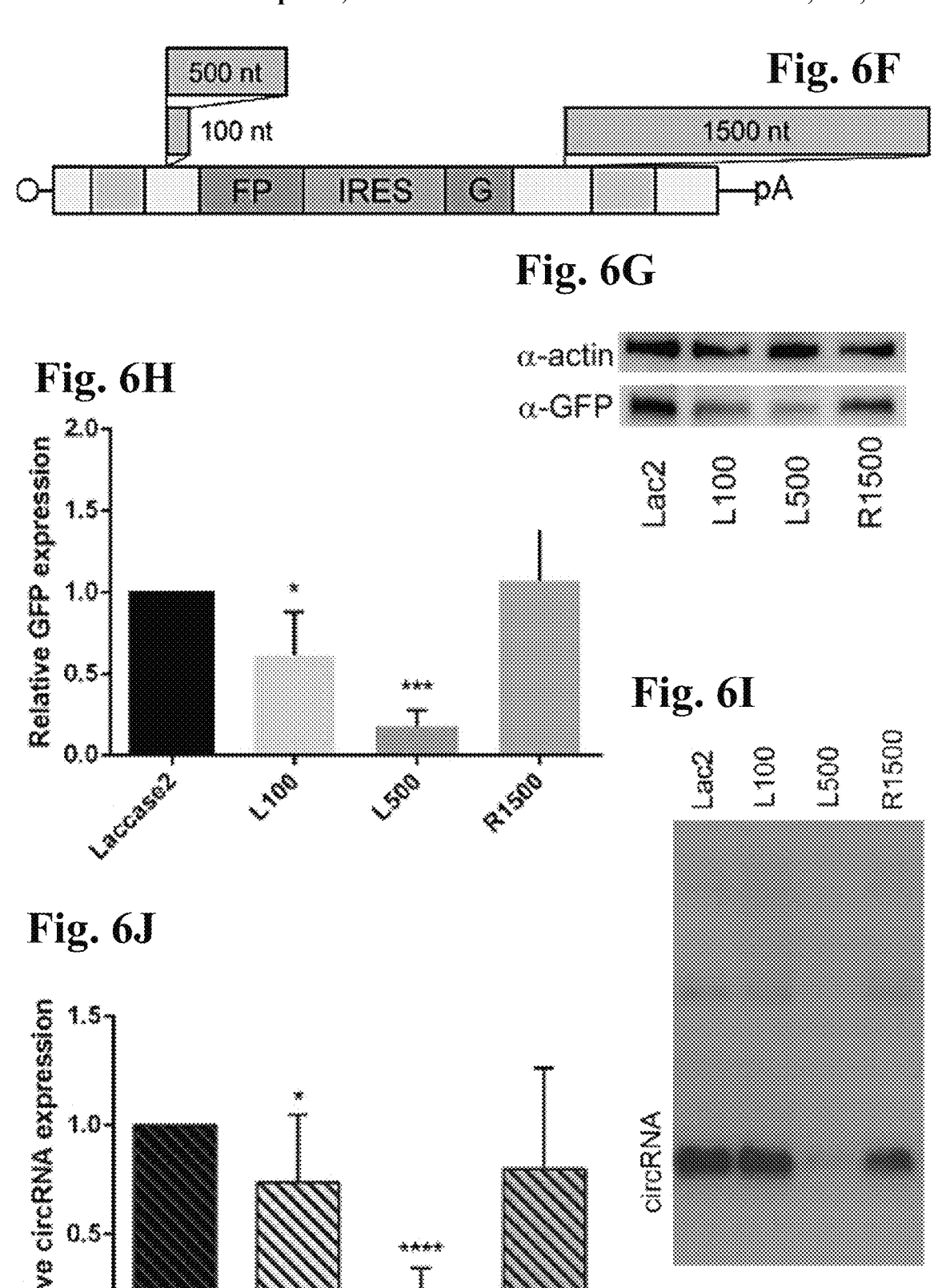
FIGS. 6F-6J show GFP expression in HEK293 cells transfected with constructs containing Laccase2 intron pairs with randomized sequence insertions as indicated.

However, insertion into the right ZKSCAN1 intron slightly decreased expression GFP (FIGS. 6B-6C) and circRNA expression (FIGS. 6D-6E).

Figures 6P, 6Q, 6R, 6S, 6T:
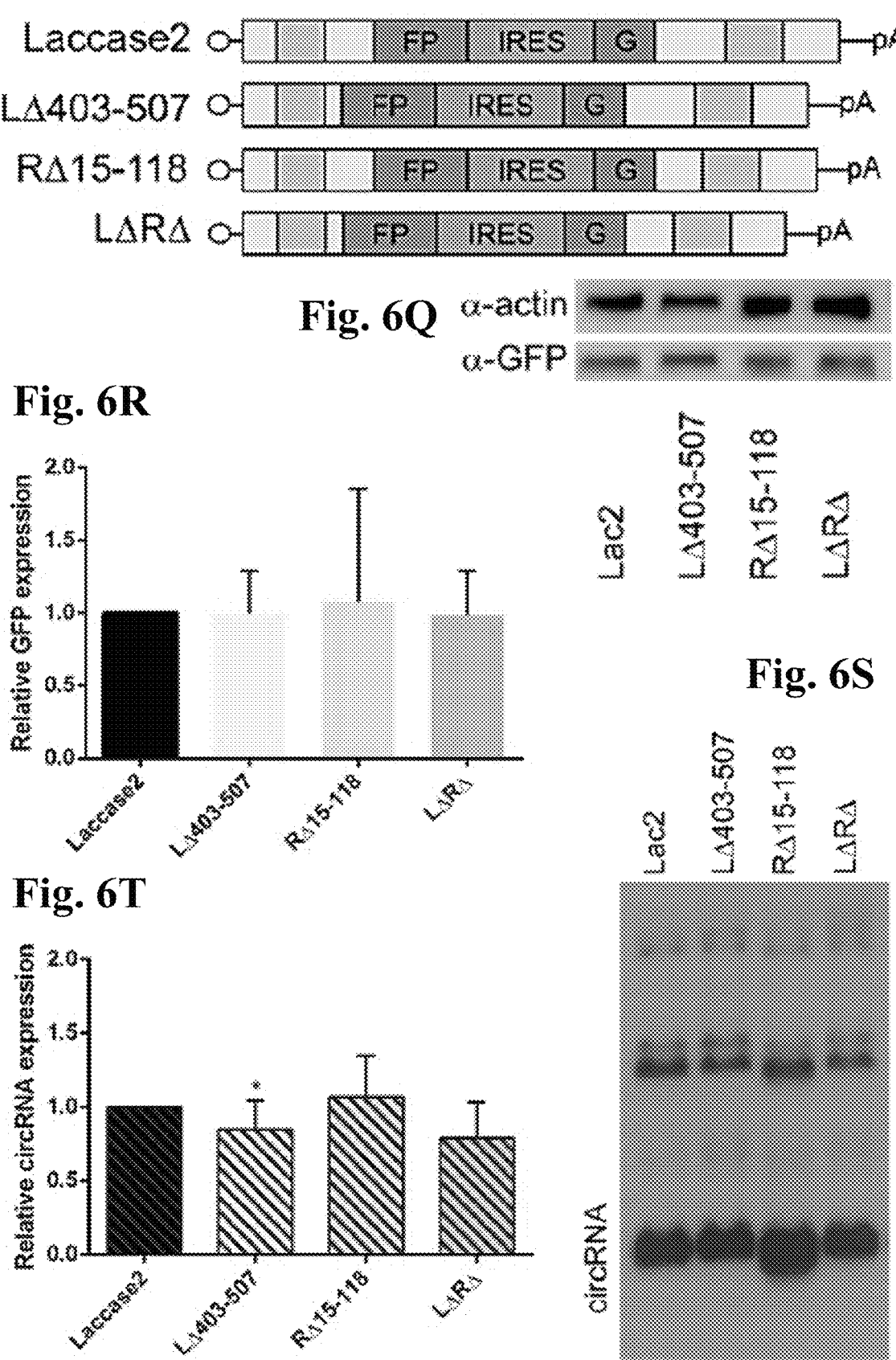

Deletion constructs were also created for both Laccase2 (FIG. 6P) and ZKSCAN1 (FIG. 6K), designed to remove as much sequence as possible based on the results in the HIPK3 intron pair observed in Example 2. Examples of Laccase2, and ZKSCAN1 intron sequences having deleted regions are provided in Table 3. For ZKSCAN1, it was not possible to design a deletion in the left intron because of space constraints between the Alu element and splice site (FIG. 6K). For Laccase2, LΔ403-507 and RΔ15-118 constructs and a combined deletion were created (FIG. 6P).

The ZKSCAN1 and Laccase2 deletions were all tolerated and expressed GFP (FIGS. 6L-6M (ZKSCAN1) and 6Q-6R (Laccase2)) and circRNA (FIGS. 6N-6O (ZKSCAN1) and 6S-6T (Laccase2)) at equivalent levels to the original.

Therefore, the results from additional intron pairs confirmed that intronic spacing effects on splicing efficiency appear to be conserved in general.

Example 4. IRES Elements Regulate circRNA Levels and Translation

Figure 7A:
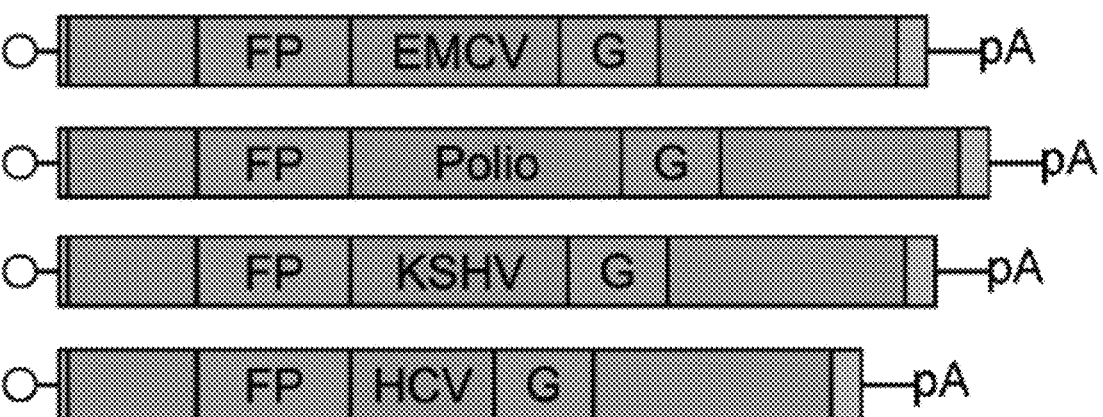
Figure 7B:
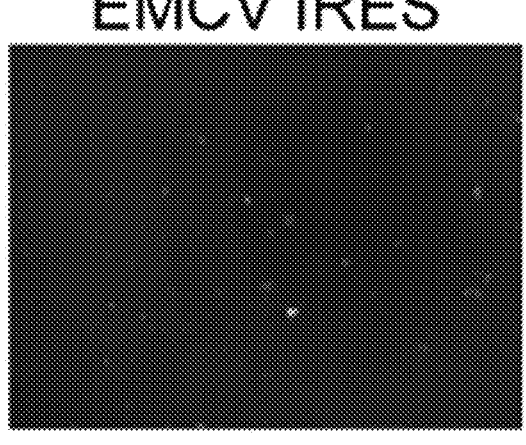
FIGS. 7B-7E show representative images of GFP fluorescence in HEK293 cells four days after transfection with HIPK3 split GFP constructs created with EMCV IRES (FIG. 7B); Poliovirus IRES (FIG. 7C); KSHV IRES (FIG. 7D); and HCV IRES (FIG. 7E).
Figure 7C:
Figure 7C:
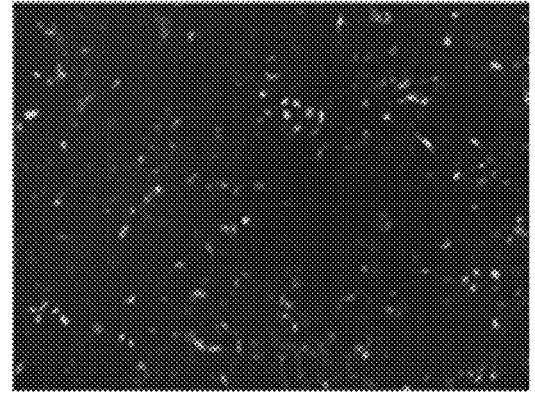
Figure 7D:
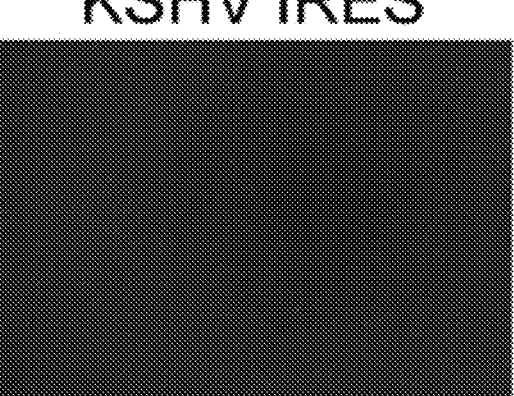
Figure 7E:
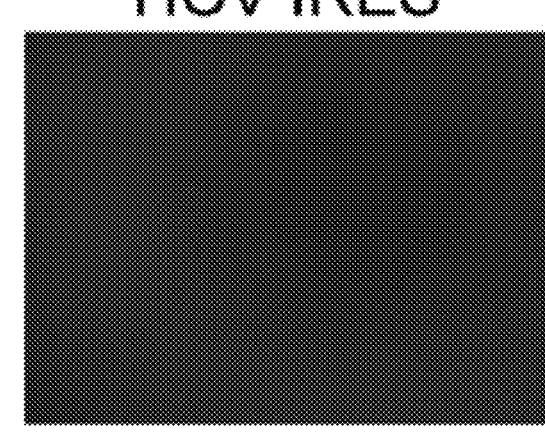
Figure 7F:
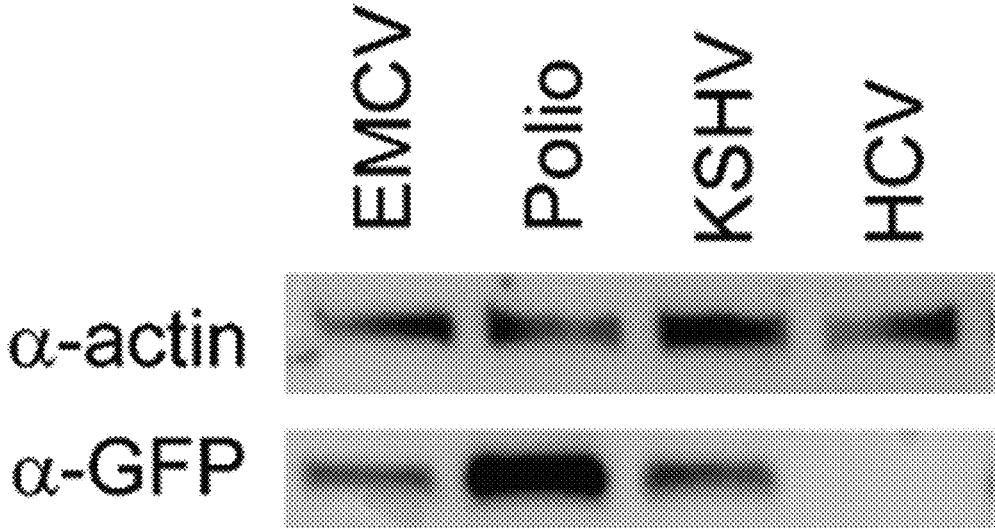
FIGS. 7F and 7G depict a western blot analysis for GFP expression where
Figure 7G:
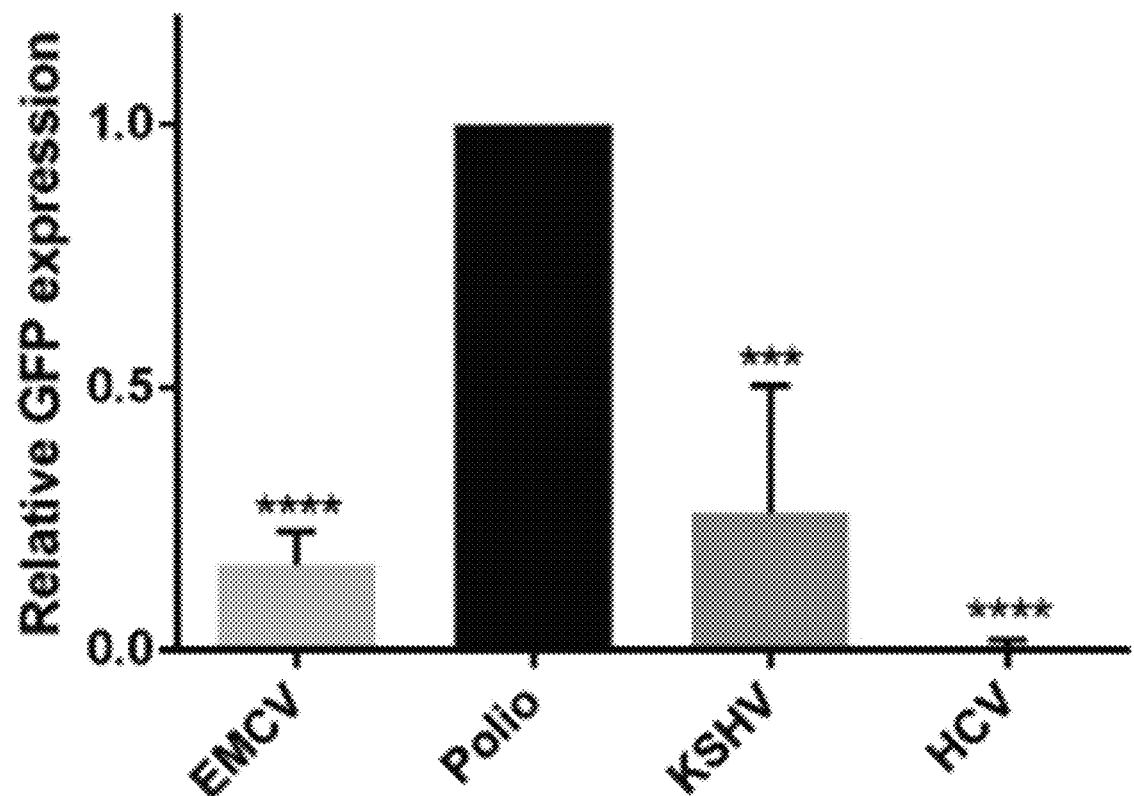
Figure 7N:
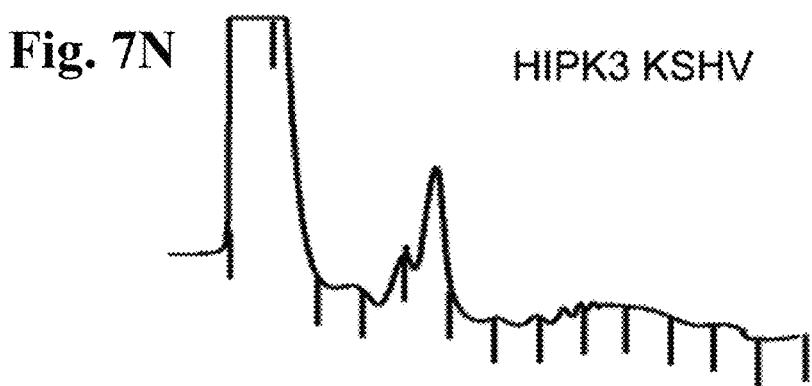
Figure 7O:
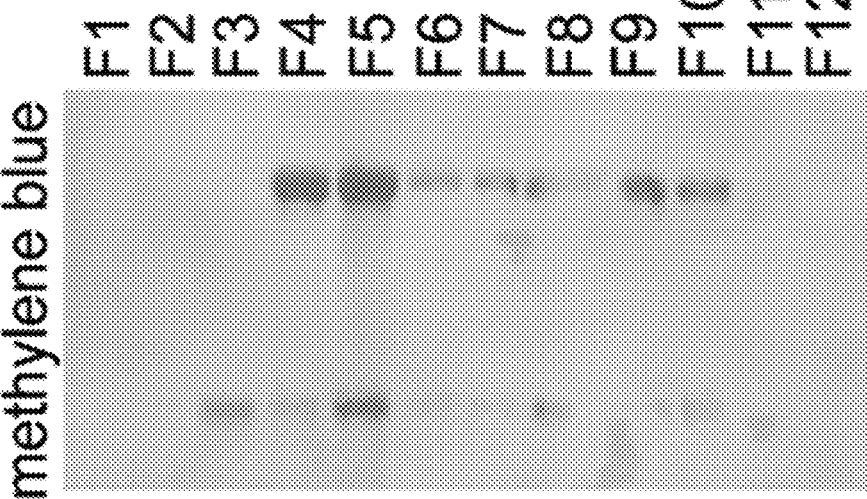
Figure 7P:
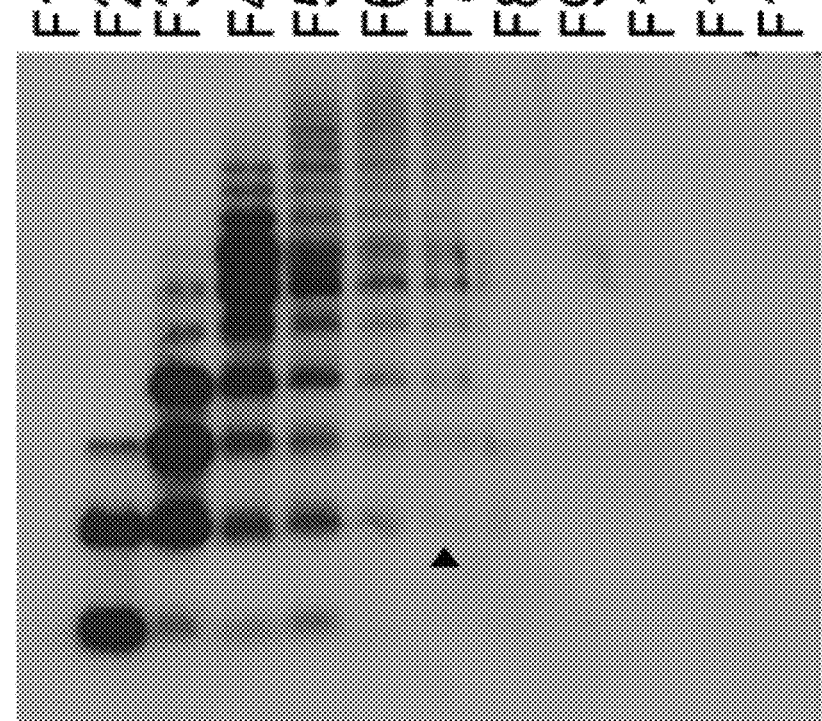
Figures 9A, 9B, 9C, 9D:
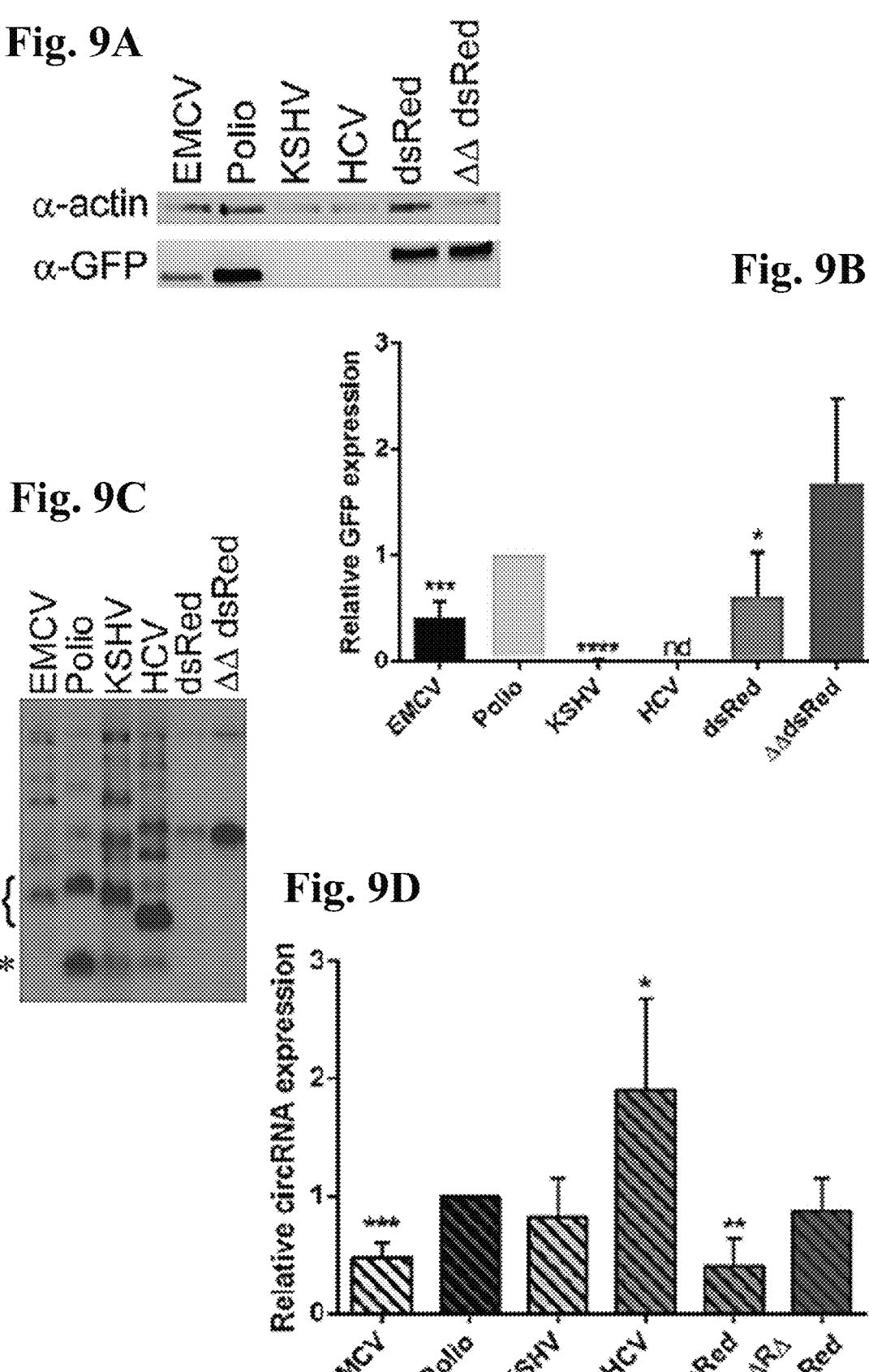
FIGS. 9A-9H are schematics, images, and graphs showing IRES-mediated translation efficiency and circRNA expression varied in glioblastoma and hepatocarcinoma cell lines in accordance with embodiments of the present disclosure.
Figures 9E, 9F, 9G, 9H:
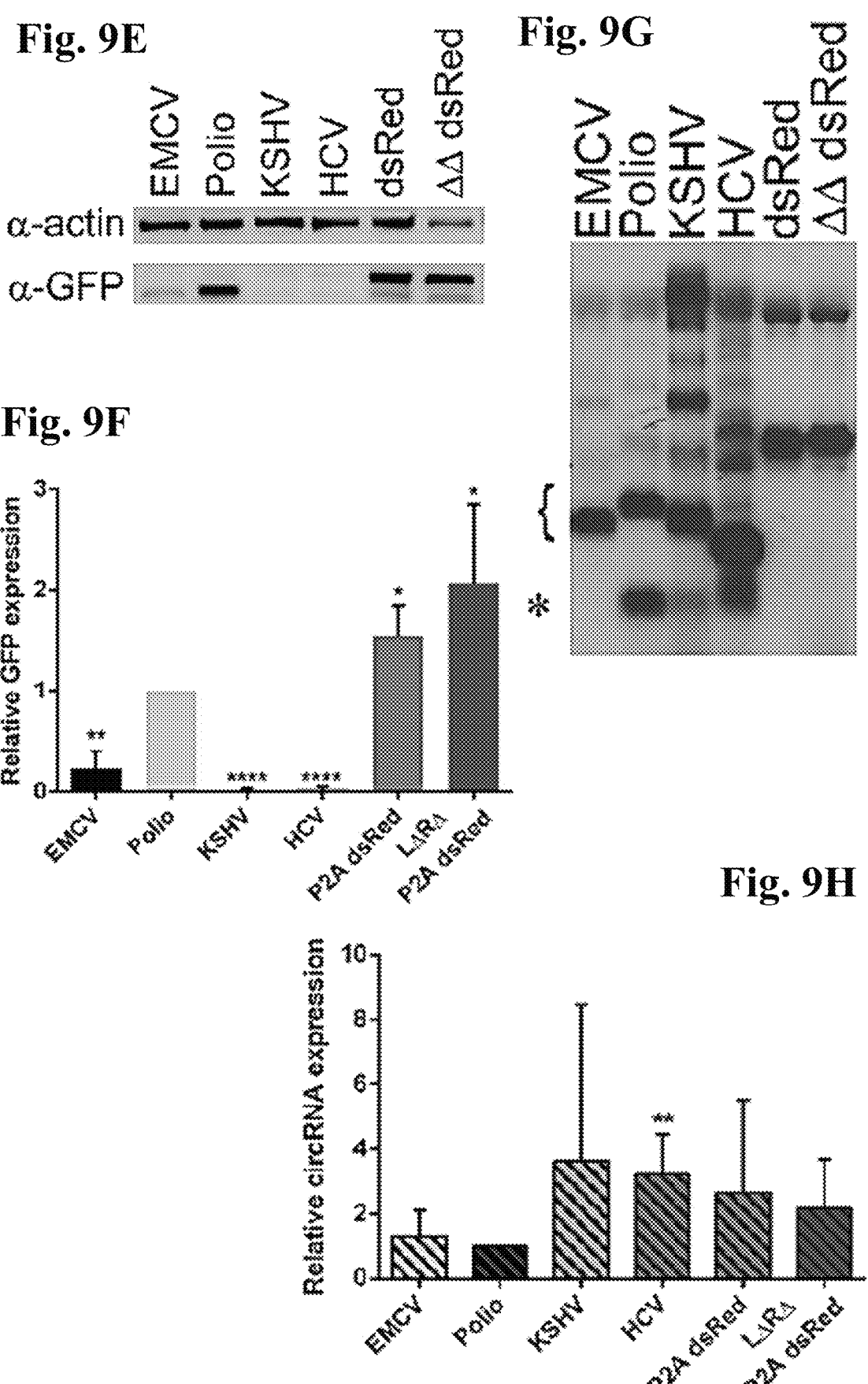

In the systems described in the above Examples, GFP expression was a product of both circRNA levels and IRES activity. As circRNAs do not contain a 5' end, canonical cap-dependent translation cannot occur, and thus must rely on IRES elements to initiate cap-independent translation and protein synthesis. Versions of the HIPK3 split GFP construct were created containing the encephelomyocarditis virus (EMCV) IRES, poliovirus IRES, Kaposi sarcoma-associated herpesvirus (KSHV) vFLIP IRES, or hepatitis C virus (HCV) IRES (FIG. 7A). Sequences of these different IRES elements used in this Example are provided in Table 6.

TABLE 6

| DESCRIPTION | SEQUENCE | SEQ ID NO: |
|---|---|---|
| Encephalomyo-carditis virus IRES | GATCCGCCCCTCTCCCTCCCCCCCCCCTAACGTTACTG GCCGAAGCCGCTTGGAATAAGGCCGGTGTGCGTTTGT CTATATGTTATTTTCCACCATATTGCCGTCTTTTGGCA ATGTGAGGGCCCGGAAACCTGGCCCTGTCTTCTTGAC GAGCATTCCTAGGGGTCTTTCCCCTCTCGCCAAAGGA ATGCAAGGTCTGTTGAATGTCGTGAAGGAAGCAGTTC CTCTGGAAGCTTCTTGAAGACAAACAACGTCTGTAGC GACCCTTTGCAGGCAGCGGAACCCCCCACCTGGCGAC AGGTGCCTCTGCGGCCAAAAGCCACGTGTATAAGATA CACCTGCAAAGGCGGCACAACCCCAGTGCCACGTTGT GAGTTGGATAGTTGTGGAAAGAGTCAAATGGCTCTCC TCAAGCGTATTCAACAAGGGGCTGAAGGATGCCCAGA AGGTACCCCATTGTATGGGATCTGATCTGGGGCCTCG GTACACATGCTTTACATGTGTTTAGTCGAGGTTAAAAA AACGTCTAGGCCCCCCGAACCACGGGGACGTGGTTTT CCTTTGAAAAACACGATGATAATATGGCCACA | 26 |
| Polio virus IRES | TTAAAACAGCTCTGGGGTTGTTCCCACCCCAGAGGCC CACGTGGCGGCCAGTACACTGGTATTGCGGTACCTTT GTACGCCTGTTTTATACTCCCTTCCCCCGTAACTTAGA AGCACAATGTCCAAGTTCAATAGGAGGGGGTACAAAC CAGTACCACCACGAACAAGCACTTCTGTTCCCCCGGT GAGGCTGTATAGGCTGTTTCCACGGCTAAAAGCGGCT GATCCGTTATCCGCTCATGTACTTCGAGAAGCCTAGTA TCACCTTGGAATCTTCGATGCGTTGCGCTCAACACTCA ACCCCAGAGTGTAGCTTAGGTCGATGAGTCTGGACGT TCCTCACCGGCGACGGTGGTCCAGGCTGCGTTGGCGG CCTACCTGTGGCCCAAAGCCACAGGACGCTAGTTGTG AACAAGGTGTGAAGAGCCTATTGAGCTACCTGAGAGT CCTCCGGCCCCTGAATGCGGCTAATCCTAACCACGGA GCAGGCAGTGGCAATCCAGCGACCAGCCTGTCGTAAC GCGCAAGTTCGTGGCGGAACCGACTACTTTGGGTGTC CGTGTTTCCTTTTATTTTTACAATGGCTGCTTATGGTGA CAATCATTGATTGTTATCATAAAGCAAATTGGATTGGC CATCCGGTGAGAATTTGATTATTAAATTACTCTCTTGT TGGGATTGCTCCTTTGAAATCTTGTGCACTCACACCTA TTGGAATTACCTCATTGTTAAGATAT | 27 |
| Kaposi sarcoma-associated herpesvirus (KSHV) vFLIP IRES | TTGGACAGACTCCTACTTATAAAGCAGGTGTCCAAAG AACACTTTCAAAAGACAGGGAGCGCCTGCCTGTTAGT GGCCAGTAAGCTCAGAAGCCTCACGCCTATTTCTACC AGTTCACTTTGCTATGCCGCGGCAGACTCCTTTTCCCG CCAAGAACTTATAGACCAGGAGAAAGAACTCCTTGAG AAGTTGGCGTGGCGAACAGAGGCAGTCTTAGCGACGG ACGTCACTTCCTTCTTGTTACTTAAATTGCTGGGGGGC TCCCAACACCTGGACTTTTGGCACCACGAGGTCAACA CCCTGATTACAAAAGCCTTAGTTGACCCAAAGACTGG CTCATTGCCCGCCTCTATTATCAGCGCTGCAGGCTGTG CGCTGTTGGTTCCTGCCAACGTCATTCCGCAGGATACC CACTCGGGTGGGGTAGTTCCTCAGCTGGCAAGCATAT TGGGATGCGATGTTTCCGTTCTACAGGCGGCAGTGGA ACAGATCCTAACATCTGTTTCGGACTTTGATCTGCGCA TTCTGGACAGCTATTAAGCTTGTGATTTTGTTTAGGGC GGAAAAATAAATTTTCCTTTGTTTTTTCCACATCGGTGC | 28 |

TABLE 6-continued

| DESCRIPTION | SEQUENCE | SEQ ID NO: |
|---|---|---|
| | CTTCACATATACAA | |
| hepatitis C virus (HCV) IRES | GCCAGCCCCCGATTGGGGGCGACACTCCACCATAGAT CACTCCCCTGTGAGGAACTACTGTCTTCACGCAGAAA GCGTCTAGCCATGGCGTTAGTATGAGTGTCGTGCAGC CTCCAGGACCCCCCCTCCCGGGAGAGCCATAGTGGTC TGCGGAACCGGTGAGTACACCGGAATTGCCAGGACGA CCGGGTCCTTTCTTGGATCAACCCGCTCAATGCCTGGA GATTTGGGCGTGCCCCCGCGAGACTGCTAGCCGAGTA GTGTTGGGTCGCGAAAGGCCTTGTGGTACTGCCTGAT AGGGTGCTTGCGAGTGCCCCGGGAGGTCTCGTAGACC GTGCACCATGAGCACGAATCCTAAACCTCAAAGAAAA ACCAAACGTAACACCAACCGCCGCCCACAGGACGTC | 29 |

Constructs were transfected into HEK293 cells and expression assayed at 4 days post-transfection by GFP fluorescence (FIGS. 7B-7E) and western blot analysis (FIGS. 7F-7G). circRNAs containing these different IRES elements displayed variable levels of GFP expression, with the poliovirus IRES-containing circRNA construct yielding ~5-fold higher expression compared to EMCV and KSHV IRES elements. In contrast, no GFP expression was observed with the HCV IRES (FIGS. 7B-7G).

To directly assess translation efficiency, polyribosome fractions were isolated and the bound RNAs were visualized by northern blot using a probe specific for GFP (FIGS. 7H-7P). In brief, HEK293 cells were seeded overnight into 10 cm plates and were transfected at ~70% confluency using PEI Max with 8 g of the indicated plasmids. 24 h post-transfection, cells were split and seeded 1:2 into 10 cm plates. Cells were grown to 60-70% confluency, then incubated in media containing cycloheximide (CHX, 100 g/mL) for 10 min at 37° C., followed by two washes with ice-cold PBS containing CHX. Cells were lysed (20 mM Tris-HCl pH 7.4, 140 mM KCl, 5 mM MgCl$_2$, 1 mM DTT, 1% Triton X-100) and passed through a 27½-gauge needle five times to disrupt cell membranes. Lysates were spun to remove nuclei and spun again to remove remaining cellular debris. Clarified lysate was loaded on top of a linear 10-50% sucrose gradient prepared in polysome gradient buffer (20 mM Tris-HCl pH 7.4, 140 mM KCl, 5 mM MgCl$_2$) and spun for 2 hours at 32,000 rpm in a SW41 swinging bucket rotor with no break. Gradients were fractionated into 750 μL fractions with continuous monitoring of absorbance at 254 nm using a Brandel gradient fractionator system. RNA was extracted from each gradient fraction using TRIzol reagent. RNAs were visualized by northern blot.

RNAs associated with multiple ribosomes (polyribosomes) were translated more efficiently, while those associated with two (disome) or a single (monosome) ribosome were translated less efficiently. The circGFP RNA containing the EMCV IRES was present on mono- and disomes, although much of the circRNA was untranslated. The KSHV IRES-containing circRNA was also present in fractions corresponding to monosomes and disomes, although, like the EMCV circRNA, a large portion of the circRNA was untranslated, showing that low GFP protein levels are due to low translation efficiency of these circRNAs. The poliovirus IRES-containing circGFP RNA, in contrast, was detected in higher fractions corresponding to multiple bound ribosomes, correlating with the observed higher levels of GFP expression (FIGS. 7H-7P).

Confirming the lack of protein expression with the HCV IRES, a large majority of the circRNA was in an unbound fraction; in contrast, a control linear GFP mRNA was detected in high-weight polysome fractions (FIGS. 8A-8F). Overall, levels of RNA and protein of these constructs in U87 and Huh7 cell lines were similar to those observed in 293T cells (FIGS. 9A-9H), suggesting that IRES-mediated translation efficiency of these circRNA vectors is similar in vitro.

When visualizing the total RNA produced from these constructs through northern blot, some differences were noticed. First, the total amount of circRNA produced varied among the four constructs. The HCV IRES construct expressed the highest levels of circRNA, followed by KSHV, poliovirus, and finally EMCV IRES (FIGS. 7Q and 7R). Although the four IRES elements varied in size, there was not a strong correlation between IRES (and therefore circRNA) size and circRNA levels. Second, there were dramatic differences in the type of RNA species produced, other than the circRNA. Notably, a RNA species smaller than the circRNA was observed with both the poliovirus and KSHV constructs. Additionally, the KSHV construct produced several larger RNA species (FIG. 7Q). Interestingly, these higher bands were detected in polyribosome fractions, while the small RNA species was not (FIGS. 7H-7P). Both the small RNA species and the larger KSHV RNA species were RNase R resistant, suggesting that they may also be circular (FIG. 7S).

Example 5. IRES Elements Significantly Affect circRNA Splicing Patterns

To further interrogate the identity of the additional RNA species observed, RNase H digestion was performed using an oligonucleotide that binds the backsplice junction, confirming the circular nature of these RNA species. The bands corresponding to the main circRNAs remained. Intriguingly, many of the higher KSHV bands disappeared altogether or decreased in intensity, while the bands corresponding to the main circRNA and small circRNA increased in intensity, suggesting that these larger species may be concatemers (FIG. 10A). Total RNA was then probed with a probe specific to the backsplice junction. The RNA banding pattern was similar to that observed with a probe to the GFP exon, suggesting that these RNA species represent spliced products (FIG. 10B).

To elucidate the identity of the additional spliced products produced by poliovirus and KSHV circRNAs, total RNA was probed against the construct's respective IRES elements. This probe detected most of the RNA species but was unable to detect the small circRNA, indicating that this species lacks the IRES, suggesting that the IRES element was spliced out of the RNA product (FIGS. 10C-10D). A virtual northern blot was then performed using extracted RNA corresponding to the small circRNA. In brief, 5 g of RNA was separated on a denaturing agarose. The gel was stained with ethidium bromide to visualize the ribosomal RNA. Pieces of the gel corresponding to the larger and smaller circRNAs were cut based on distance from the 18S rRNA (distances measured from a northern blot). RNA was extracted from the gel. RNA was DNase treated using the Turbo DNA-free kit (Ambion). Equal nanogram amounts of DNase-treated RNA were converted to cDNA using the High Capacity RNA-to-cDNA kit (Applied Biosystems). Products of this reverse transcription reaction were utilized as template for PCR using primers specific to the backsplice (5'-CTGCTTGTCGGCCATGATATAGACGTTGTGGC-3' (SEQ ID NO: 30); 5'-CAAGCTGACCCTGAAGTT-CATCTGCACCACC-3'; (SEQ ID NO: 31)) or primers spanning the IRES element (5'-GGCCGACAAGCAGAAGAACGGCATCAAG-3' (SEQ ID NO: 32); 5'-GGTGGTGCAGAT-GAACTTCAGGGTCAGCTTG-3' (SEQ ID NO: 33)), followed by sequencing of the purified PCR products.

Figure 10E:
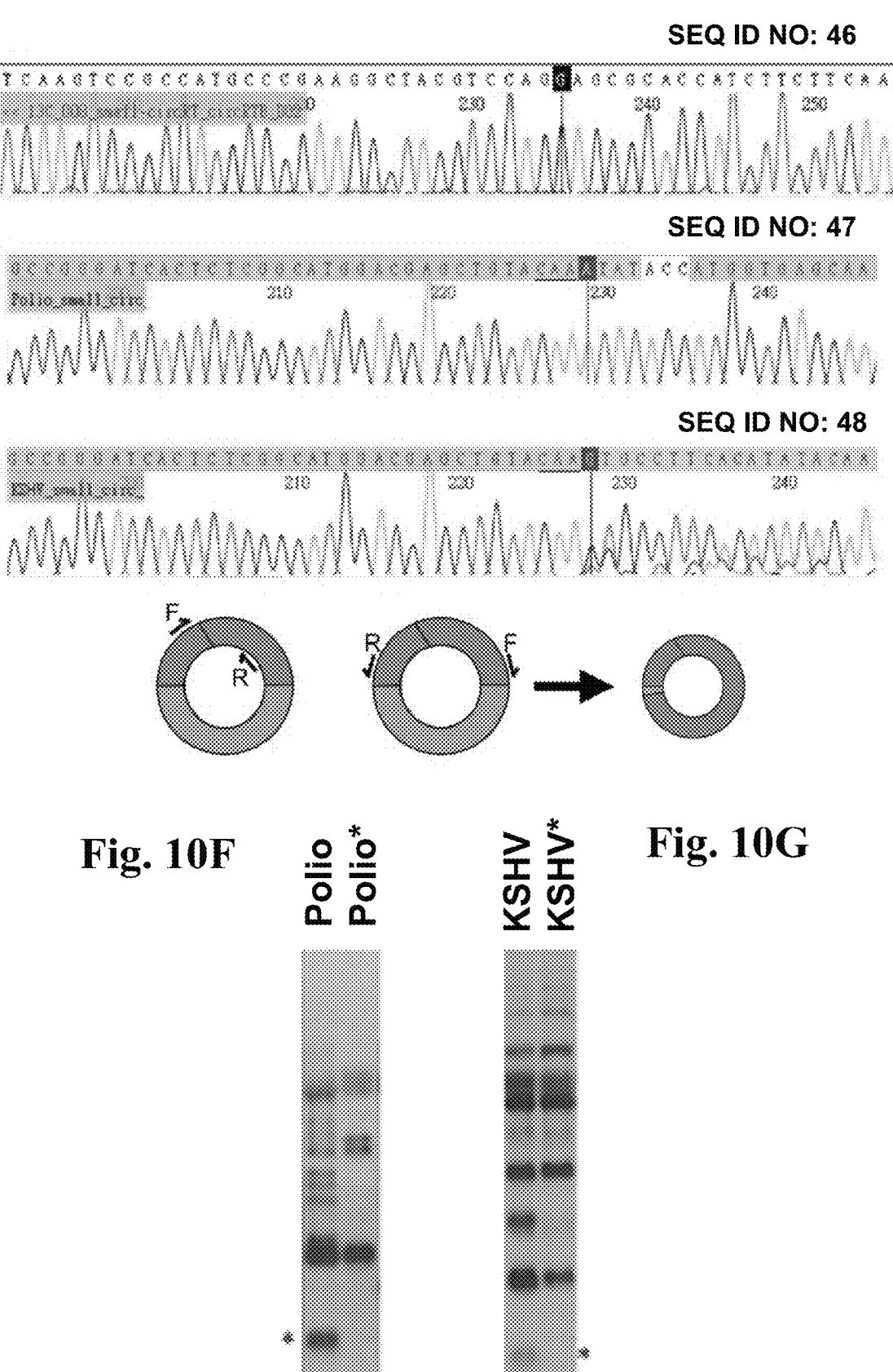

Following cDNA synthesis, PCR products were obtained using primers amplifying across the IRES and sequenced, confirming that the IRES was indeed spliced out of these circRNA products. In both cases, a weak splice donor in the last two codons of GFP was spliced to a weak acceptor at the end of the IRES (FIG. 10E). Having identified the splice sites involved, alternative donor site was abolished the by making silent mutations in the GFP coding sequence, which consequently eliminated formation of the small circRNA (FIGS. 10F-10G). These results highlighted the importance of identifying weak donor/acceptor splice sites in the design of circRNA vectors.

Example 6. Larger circRNA Generation does not Affect Expression

Figure 11G:
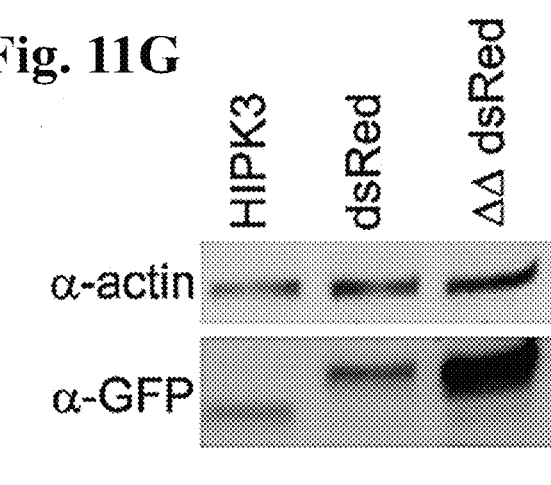
FIGS. 11G and 11H depict a western blot analysis for GFP expression where
Figure 11H:
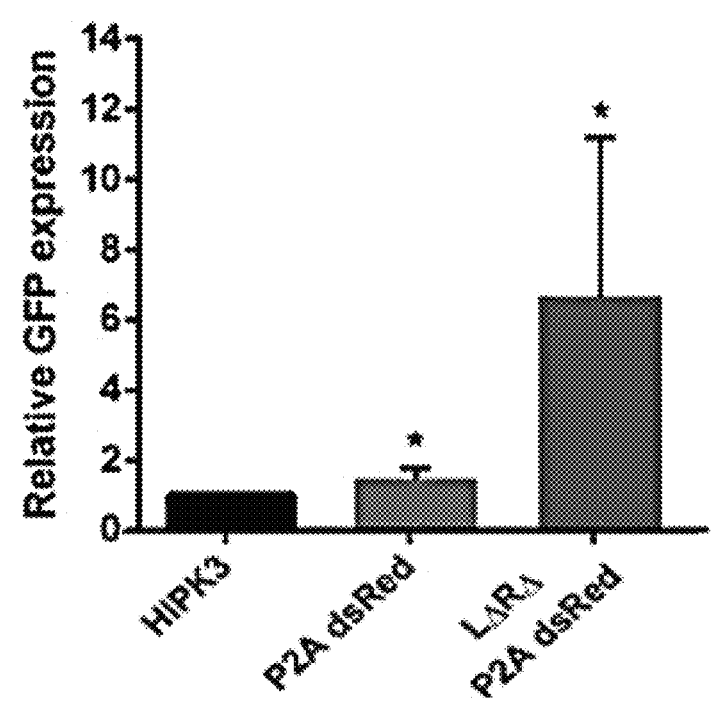
Figure 11I:
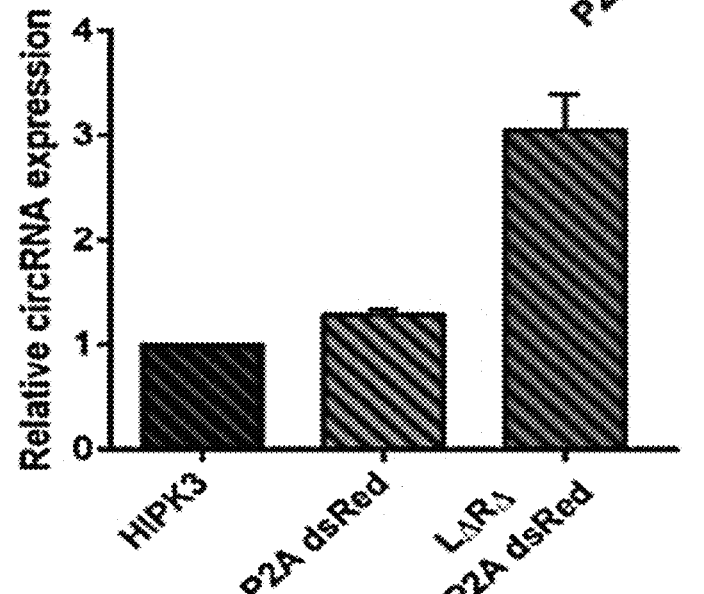
Figure 11J:
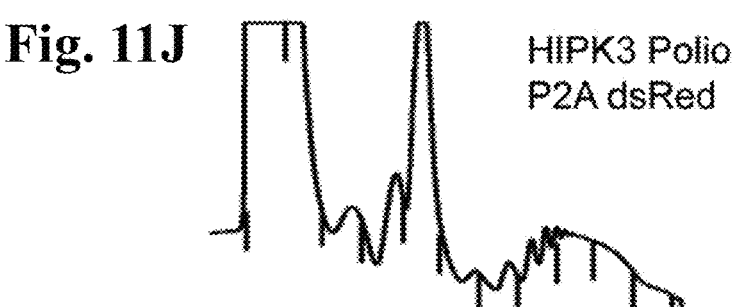
FIGS. 11J-11L show images of the HIPK3 polio P2AdsRed construct was transfected into HEK293 cells and harvested in cycloheximide followed by a sucrose gradient fractionation where
Figure 11K:
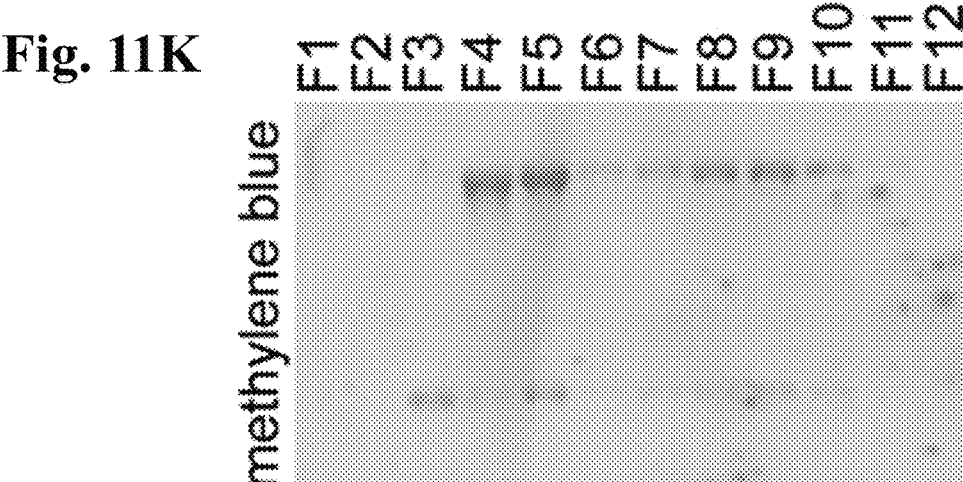
Figure 11L:
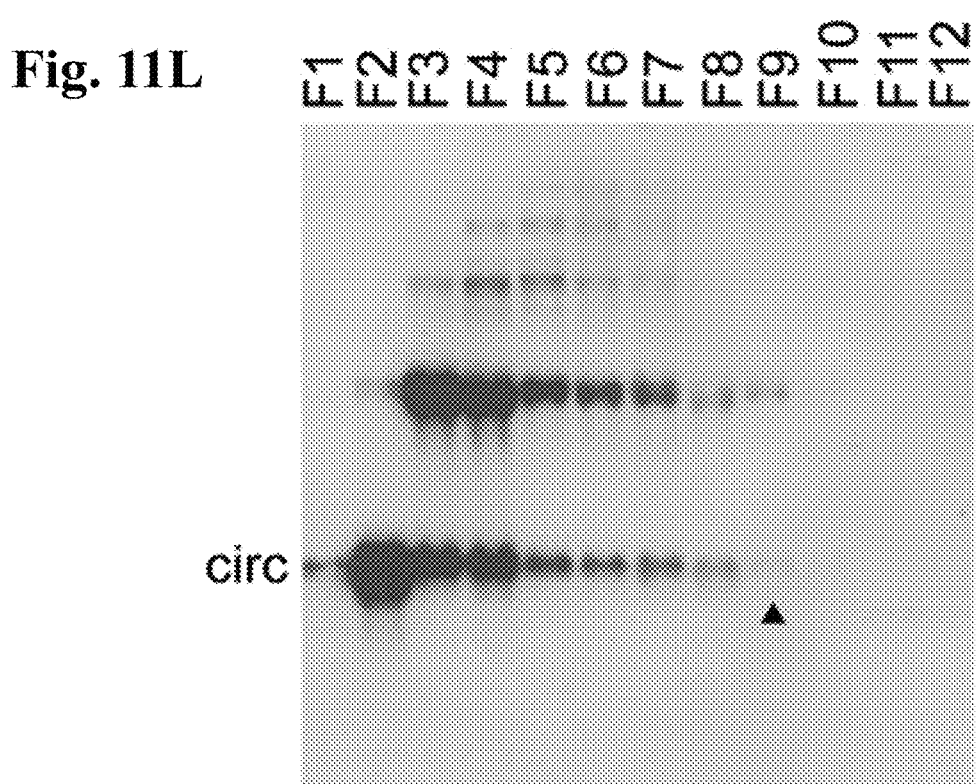

The size of endogenous circRNA exons can range from ~100 nt to >1 kb, averaging ~700 nt. circGFP RNAs in the Examples herein ranged in size from 1.1 to 1.5 kb in length, fairly large compared to endogenous circRNAs, but express at high levels. To investigate whether exon length could be further increased, a P2A self-cleaving sequence followed by the dsRed ORF downstream of the end of the GFP ORF fragment (–FP) was added, increasing the exon length by ~750 nt to a total of 2.2 kb (FIG. 11A). This larger exon was paired with both the original and LΔRΔ HIPK3 intron pairs and yielded GFP expression (FIGS. 11B-11H) comparable to previous results (See FIGS. 4A-4I), in addition to expressing dsRed (FIGS. 11E and 11F). Polyribosome analysis revealed that the GFP-dsRed circRNA was present in fractions containing multiple translating ribosomes, showing that it is efficiently translated (FIGS. 11J-11L). When the P2A sequence was added, removal of the GFP stop codon mutated the weak splice donor site identified earlier. Accordingly, when the total RNA species was analyzed by northern blot, only two species were detected: the circGFP RNA and a larger RNA species (FIGS. 11M and 11I). RNase R and RNase H analyses confirmed the circular nature of the putative circRNA band and revealed that the larger species was linear (FIGS. 11N and 11O). Probing for the backsplice junction revealed that both bands contained the backsplice junction, indicating that the larger linear species had undergone a splicing event (FIG. 11P). These results showed that both the endogenous and synthetic HIPK3 backsplicing introns can mediate splicing of large circRNA products.

Figures 12A, 12B, 12C:
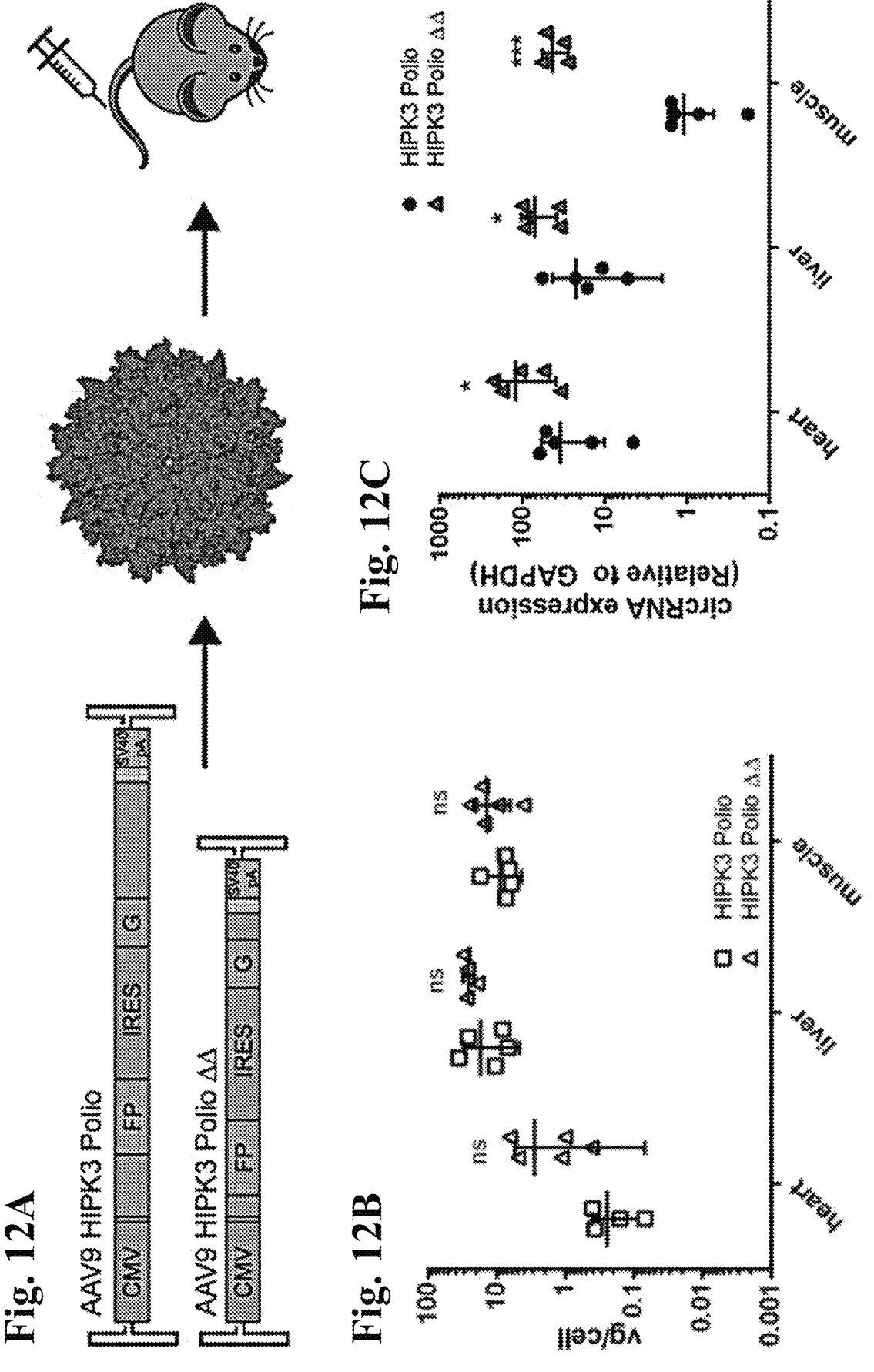

Example 7. circRNAs can be Highly Expressed Using AAV Vectors in Cardiac and Muscle Tissue To gather further insight into circRNA backsplicing and IRES-mediated translation efficiency in vivo, DNA constructs were packaged containing a cytomegalovirus (CMV) promoter driving (1) the original HIPK3 intron and poliovirus IRES or (2) the LΔRΔ intron and poliovirus IRES with the split GFP exon and flanked by inverted terminal repeats into AAV vectors (FIG. 12A). In brief, a triple plasmid transfection protocol with modifications was used to generate recombinant AAV vectors. Briefly, the transfection mixture contained (1) the pXR helper plasmid; (2) the adenoviral helper plasmid pXX6-80; and (3) the indicated circRNA-encoding sequence, driven by a CMV promoter and a SV40 polyA, flanked by AAV2 inverted terminal repeats (ITRs). Vector purification was carried out following polyethylene glycol (PEG) precipitation (8% w/v) from media supernatant using iodixanol gradient ultracentrifugation and desalting with ZebaSpin desalting columns (40K MWCO, Thermo Scientific). Vector genome (vg) titers were obtained by quantitative PCR (Lightcycler 480, Roche Applied Sciences) using SYBR Green (Roche Applied Sciences) and primers designed to selectively bind AAV2 inverted terminal repeats (forward, 5'-AACATGC-TACGCAGAGAGGGAGTGG-3' (SEQ ID NO: 34); reverse, 5'-CATGAGACAAGGAACCCCTAGTGATG-GAG-3' (SEQ ID NO: 35)).

Mice (strain: C57BL/6) in each cohort were injected intravenously through the tail vein with $3 \times 10^{11}$ vg/animal. Tissues were harvested at 4 weeks post-injection. At 4 weeks post-injection, mice were overdosed with tribromoethanol (Avertin) (0.2 mL/10 g of 1.25% solution) via the intraperitoneal route. This was followed by transcardial perfusions of phosphate-buffered saline. Portions of the harvested organs (heart, liver, skeletal muscle) were cut and stored in RNAlater solution (Invitrogen); the remainder was postfixed in 4% paraformaldehyde.

Next, vector genome copy number in tissues was quantified. In brief, Genomic DNA was extracted from sections of fixed tissue using the QiaAmp DNA FFPE Tissue Kit (QIAGEN, Germantown, MD, USA). To calculate viral genome copy numbers, quantitative PCR was performed with primers specific to the CMV promoter (5'-CAAGTACGCCCCCTATTGAC-3' (SEQ ID NO: 36); and 5'-AAGTCCCGTTGATTTTGGTG-3' (SEQ ID NO: 37)). The vector genome copy numbers were normalized to the mouse lamin B2 locus as the housekeeping gene (primers 5'-GGACCCAAGGACTACCTCAAGGG-3' (SEQ ID NO: 38); and 5'-AGGGCACCTCCATCTCGGAAAC-3' (SEQ ID NO: 39)). The AAV vector genome copy numbers were statistically indistinguishable between cohorts, confirming equivalent dosing (FIG. 12B).

Figure 12D:
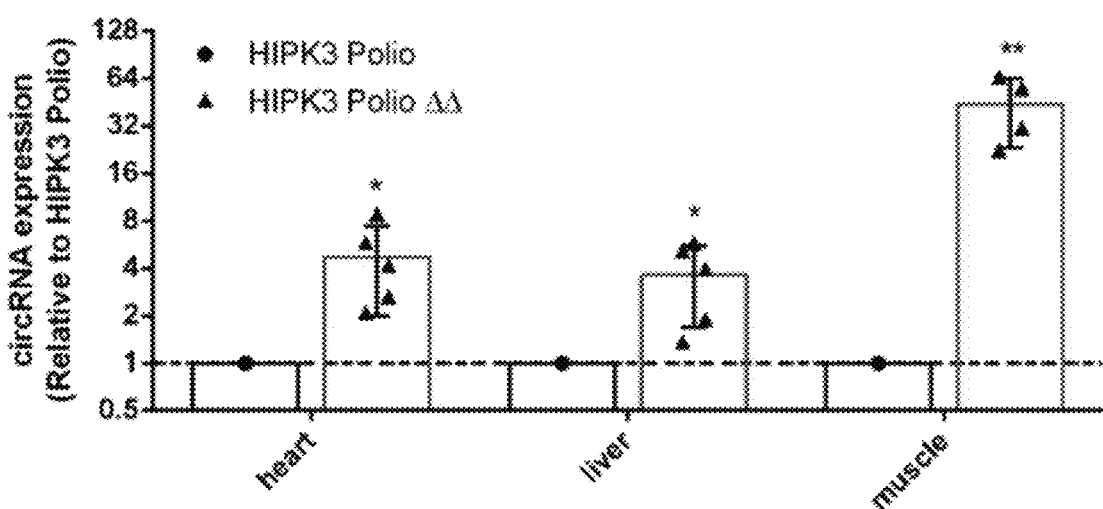
Figure 12D:
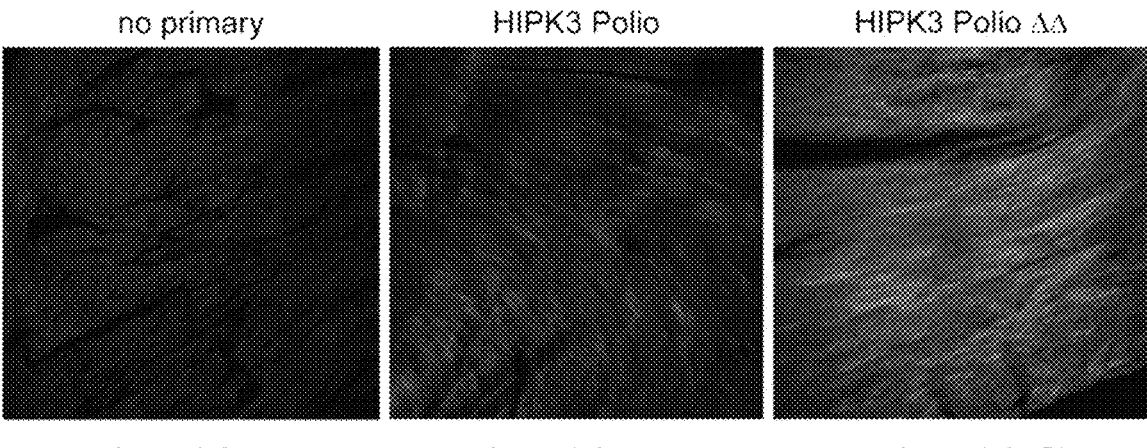
Figure 12H:
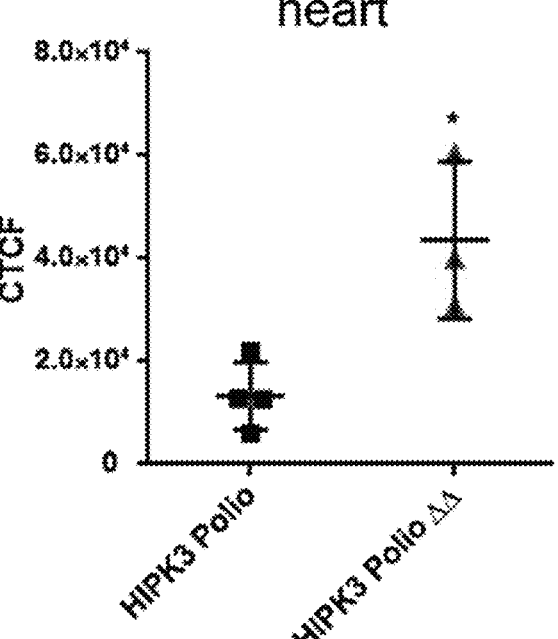
Figure 12L:
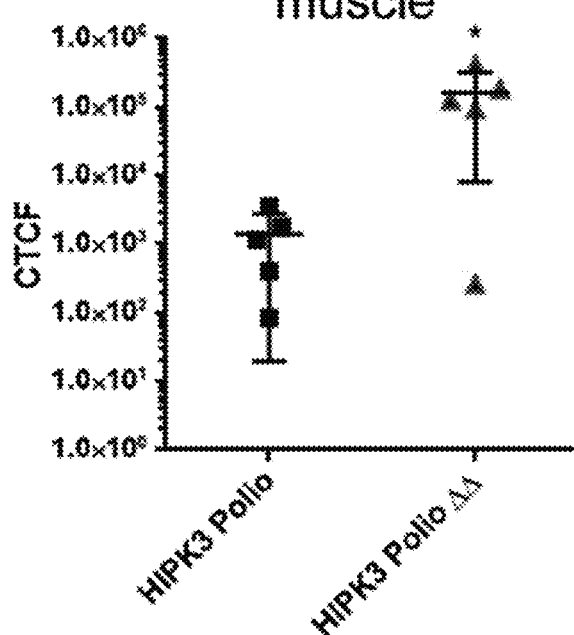
Figure 12L:
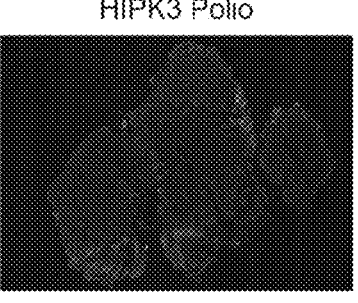
Figure 12L:
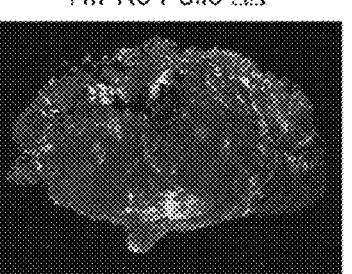
Figures 13A, 13B, 13C, 13D:
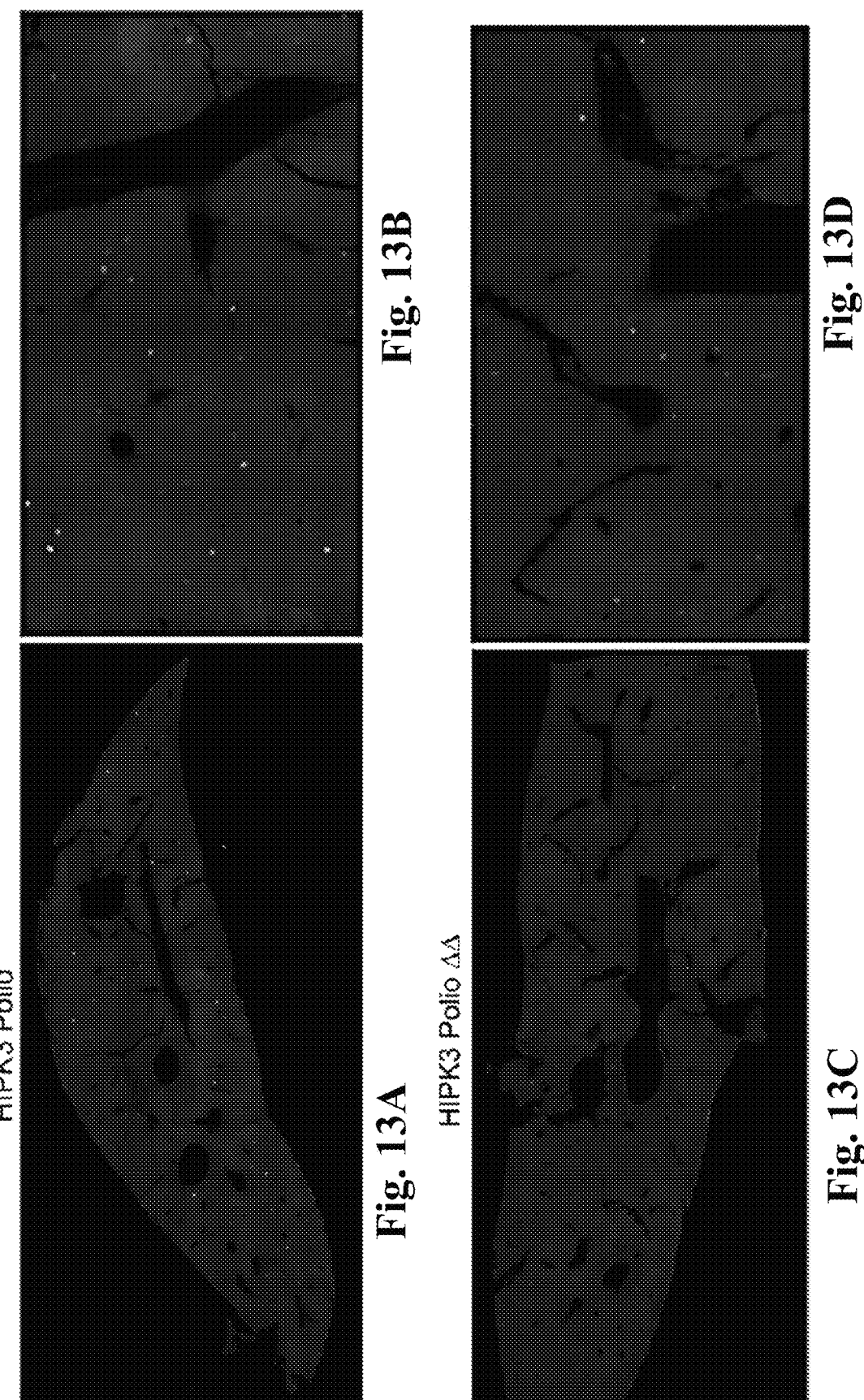
FIGS. 13A-13D are images showing circRNA reporters expressed low GFP protein levels in the liver in accordance with embodiments of the present disclosure.

Next, circRNA expression in cardiac, liver, and skeletal muscle tissues was assessed using RT-PCR. In brief, 5 µg of RNA was DNase treated using the Turbo DNA-free kit (Ambion). Equal nanogram amounts of DNase treated RNA were converted to cDNA using the High Capacity RNA-to-cDNA kit (Applied Biosystems). Products of the reverse transcription reaction were utilized as template for PCR (or quantitative PCR) using gene-specific primers for GFP (5'-CTGCTTGTCGGCCATGATATAGACGTTGTGGC-3' (SEQ ID NO: 40); 5'-CAAGCTGACCCTGAAGTT-CATCTGCACCACC-3' (SEQ ID NO: 41)) and glyceraldehyde 3-phosphate dehydrogenase (GAPDH) (5'-CCACTCCTCCACCTTTGAC-3' (SEQ ID NO: 42); 5'-ACCCTGTTGCTGTAGCC-3' (SEQ ID NO: 43)). Quantitative PCR was carried out using a Roche Light-Cycler 480 and SYBR Green Mastermix (Roche Applied Sciences). Quantitative RT-PCR was performed using a primer pair across the circRNA backsplice junction and revealed that the LΔRΔ intron pair led to significantly higher circRNA expression: ~4-fold higher expression in heart and liver and ~50-fold higher expression in muscle compared to the original HIPK3 introns (FIGS. 12C-12D). In particular, circRNA expression in skeletal muscle was detected at very low levels with the original HIPK3 introns, while expression dramatically increased with the LΔRΔ intron pair to levels comparable to the heart and liver (FIGS. 12C-12D).

Next, immunofluorescent staining of harvested tissues was performed. In brief, for heart and liver, 50-μm-thick sections were obtained from fixed tissue using a vibrating blade microtome. Immunohistochemical analyses of GFP expression were conducted using an antibody against GFP and Alexa Fluor goat anti-rabbit 488 secondary antibody. Sections were mounted on slides in ProLong Gold Antifade Mountant with DAPI (4',6-diamidino-2-phenylindole), is a fluorescent stain that binds strongly to adenine-thymine-rich regions in DNA. Imaging was performed on an Aperio ScanScope XT (brightfield) or an Aperio ScanScope FL (fluorescence) at 20× magnification. Skeletal muscle samples were for mounting and sectioning, followed by immunofluorescence and slide scanning. Fluorescence was quantified in all tissues in ImageJ.

Immunofluorescent staining of sectioned tissue for GFP confirmed that the LΔRΔ construct demonstrated significantly higher GFP expression in the heart (FIGS. 12E-12H) as well as skeletal muscle (FIGS. 12I-12L). GFP expression in the liver was low with both constructs, despite the difference seen in circRNA expression, indicating that the poliovirus IRES did not translate efficiently in liver (FIGS. 13A-13D). These results demonstrated that the altering intronic distances can be exploited to regulate synthetic circRNA levels in different tissues in vivo.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise.

The present disclosure shall control in the event there are any disparities between any definitions and/or description found in the cited references.

We claim:

1. A nucleic acid molecule, comprising: a nucleic acid sequence, wherein the nucleic acid sequence comprises a first circRNA-encoding sequence and a second circRNA-encoding sequence, wherein the first circRNA-encoding sequence is flanked by a left backsplicing intronic element and a right backsplicing intronic element; and wherein the second circRNA-encoding sequence is flanked by a left tRNA splicing element and a right tRNA splicing element.

2. The nucleic acid molecule of claim 1, wherein the left backsplicing intronic element comprises a nucleic acid sequence selected from any one of SEQ ID NOs: 1, 6, 11, 21, 23, and 25; and the right backsplicing intronic element comprises a nucleic acid sequence selected from any one of SEQ ID NOs: 2, 7, 12, 20, 22, and 24.

3. The nucleic acid molecule of claim 1, wherein the left tRNA splicing element comprises a nucleic acid sequence of SEQ ID NO: 17; and the right tRNA splicing element comprises a nucleic acid sequence of SEQ ID NO: 18.

4. The nucleic acid molecule of claim 1, wherein the nucleic acid sequence further comprises at least one promoter region, wherein the at least one promoter region can recruit an RNA polymerase type II, an RNA polymerase type III, or any combination thereof.

5. The nucleic acid molecule of claim 1, wherein the left tRNA splicing element, the second circRNA-encoding sequence, and the right tRNA splicing element are downstream of the first circRNA-encoding sequence.

6. The nucleic acid molecule of claim 1, wherein the right backsplicing intronic element comprises the left tRNA splicing element, the second circRNA-encoding sequence, and the right tRNA splicing element.

7. The nucleic acid molecule of claim 1, wherein the left backsplicing intronic element comprises an Alu element and the right backsplicing intronic element comprises an Alu element.

8. The nucleic acid molecule of claim 1, wherein the left backsplicing intronic element comprises a deletion of up to about 500 nucleotides and/or and the right backsplicing intronic element comprises a deletion of up to about 900 nucleotides.

9. The nucleic acid molecule of claim 1, wherein the first circRNA-encoding sequence comprises a 5' untranslated region (5' UTR) and 3' UTR, and wherein the 5' UTR comprises an internal ribosome entry site (IRES).

10. The nucleic acid molecule of claim 1, wherein the first circRNA encodes a therapeutic protein or therapeutic RNA.

11. The nucleic acid molecule of claim 1, wherein the second circRNA encodes an aptamer, a guide RNA, a protein sponge, a miRNA sponge, a protein-binding RNA, a naturally occurring circRNA, an antisense RNA, a long non-coding RNA (lncRNA), a small activating RNA (saRNA), a functional non-coding RNA, a ribosomal RNA (rRNA), a small nucleolar RNA (snoRNA), a small nuclear RNA (snRNA), a piwi-interacting RNA (piRNA), a Y-RNA, a 7SK RNA, or a 7S RNA.

12. An adeno-associated virus (AAV) vector comprising the nucleic acid molecule of claim 1.

13. An AAV particle comprising the AAV vector of claim 12.

14. A pharmaceutical composition comprising the AAV particle of claim 13 and a pharmaceutically acceptable carrier or excipient.

15. A method of delivering at least two circRNAs to a cell or tissue, the method comprising: introducing the AAV particle of claim 13 to the cell or tissue.

* * * * *

SEQUENCE LISTING

<160> NUMBER OF SEQ ID NOS: 48

<210> SEQ ID NO 1
<211> LENGTH: 391
<212> TYPE: DNA
<213> ORGANISM: Artificial Sequence
<220> FEATURE:
<223> OTHER INFORMATION: HIPK3 - Left Intron

<400> SEQUENCE: 1

```
gcctcagcct ctcaaagtgc taggattaca gggatctata cttttctttt gagggaaaat      60
gttggcaccg tttctagggc atattggcca tttcagcttc tcagtaaata tttgttaagt     120
aattaaatgc acttgattct ttattcttag ccttttaacg caatactcag aatagctgaa     180
gcaccaatta actgaaatgg agatattata aagatagtta tcttctccaa gggaaaaaat     240
catcttcatg gaaattaatt acttttttac aaattgtgaa tttgaccctt aagagttttc     300
ttcctgatat ttaaaattga aaaaaaaatt gttgacatta atatttcttc tttcctttt      360 tttcttttcc tttttttttt ttttttttgca g                                    391
```

<210> SEQ ID NO 2
<211> LENGTH: 754
<212> TYPE: DNA
<213> ORGANISM: Artificial Sequence
<220> FEATURE:
<223> OTHER INFORMATION: HIPK3 - Right Intron

<400> SEQUENCE: 2

```
gtaggtaaca actccatact ttttggttgt ttattaatgt gaaatttctg ctaaatgaaa       60
```

-continued

```
tacttttgtg tgtgtttgtg gtagaagaga ccacttcagt taaataagga aatcaagaga      120
ggatcaattt aggttcgttt taaagagatt aaaaaaaatc aagacataaa atctacccaa      180
gcaggataga aatctccact gcaaagttcc atgccaaaga catctggtta tttttatttt      240
taatggaaga cttgaaggaa tgataggtga ttaataatga tcaaacagaa gtctttaaat      300
gttggaaagt atttacatta atctttgtat atatcattgg gcattttagc acttgagaga      360
aatagtttat taaagatata atcaatcata tgtaactgaa catttagaaa aattatatac      420
aggtttgagt agcccttatc tgaaactttt ggggccagaa gtgttttgga ttccagattt      480
ttccggattt tggaatattt gcactgccaa ctagttaagc accccaaat ttgaaaattc       540 gtttcctttg agtgtcatgt caatgcccaa aaagtttcag atatttggat ttgagatgct      600
caacctgtat aaggattcag aaagttattc tgattaatga ttttaagatt cagatataca      660
ataatcccag caacttggga ggctgaggca ggagaatcac ttgaacccag gagatggagg      720
ttgcagtgag ccgagatcat gccattgcac tcca                                  754
```

```
<210> SEQ ID NO 3
<211> LENGTH: 35
<212> TYPE: DNA
<213> ORGANISM: Artificial Sequence
<220> FEATURE:
<223> OTHER INFORMATION: HIPK3 - Alu Element (or complementary region)
      of Left Intron

<400> SEQUENCE: 3
gcctcagcct ctcaaagtgc taggattaca gggat                                  35
```

```
<210> SEQ ID NO 4
<211> LENGTH: 93
<212> TYPE: DNA
<213> ORGANISM: Artificial Sequence
<220> FEATURE:
<223> OTHER INFORMATION: HIPK3 - Alu Element (or complementary region)
      of Right Intron

<400> SEQUENCE: 4
taatcccagc aacttgggag gctgaggcag gagaatcact tgaacccagg agatggaggt      60
tgcagtgagc cgagatcatg ccattgcact cca                                    93
```

```
<210> SEQ ID NO 5
<211> LENGTH: 44
<212> TYPE: DNA
<213> ORGANISM: Artificial Sequence
<220> FEATURE:
<223> OTHER INFORMATION: HIPK3 - Poly-pyrimidine Tract of Left Intron

<400> SEQUENCE: 5
tttcttcttt cctttttttt cttttccttt tttttttttt tttt                       44
```

```
<210> SEQ ID NO 6
<211> LENGTH: 608
<212> TYPE: DNA
<213> ORGANISM: Artificial Sequence
<220> FEATURE:
<223> OTHER INFORMATION: Laccase2 - Left Intron

<400> SEQUENCE: 6
tcattgagaa atgactgagt tccggtgctc tcaagtcatt gatctttgtc gacttttatt      60
tggtctctgt aataacgact tcaaaaacat taaattctgt tgcgaagcca gtaagctaca      120
```

-continued

```
aaaagaaaaa acaagagaga atgctatagt cgtatagtat agtttcccga ctatctgata      180
cccattactt atctaggggg aatgcgaacc caaaatttta tcagttttct cggatatcga      240
tagatattgg ggaataaatt taaataaata aattttgggc gggtttaggg cgtggcaaaa      300
agttttttgg caaatcgcta gaaatttaca agacttataa aattatgaaa aaatacaaca      360
aaattttaaa cacgtgggcg tgacagtttt ggacggtttt agggcgttag agtaggcgag      420
gacagggtta catcgactag gctttgatcc tgatcaagaa tatatatact ttataccgct      480
tccttctaca tgttacctat ttttcaacga atctagtata cctttttact gtacgattta      540
tgggtataat aataagctaa atcgagacta agtttattg ttatatatat ttttttttatt      600 ttatgcag                                                              608
```

<210> SEQ ID NO 7
<211> LENGTH: 848
<212> TYPE: DNA
<213> ORGANISM: Artificial Sequence
<220> FEATURE:
<223> OTHER INFORMATION: Laccase2 - Right Intron

<400> SEQUENCE: 7

```
gtaagtattc aaaattccaa aatttttac tagaaatatt cgattttta ataggcagtt       60 tctatactat tgtatactat tgtagattcg ttgaaaagta tgtaacagga agaataaagc      120
atttccgacc atgtaaagta tatatattct taataaggat caatagccga gtcgatctcg      180
ccatgtccgt ctgtcttatt attttattac cgccgagaca tcaggaacta taaaagctag      240
aaggatgagt tttagcatac agattctaga gacaaggacg cagagcaagt ttgttgatcc      300
atgctgccac gctttaactt tctcaaattg cccaaaactg ccatgcccac attttttgaac      360 tattttcgaa attttttcat aattgtatta ctcgtgtaaa tttccatcaa tttgccaaaa      420 aacttttttgt cacgcgttaa cgccctaaag ccgccaattt ggtcacgccc acactattga      480
acaattatca aattttttct cattttattc cccaatatct atcgatatcc ccgattatga      540
aattattaaa tttcgcgttc gcattcacac tagctgagta acgagtatct gatagttggg      600
gaaatcgact tattttttat atacaatgaa aatgaattta atcatatgaa tatcgattat      660
agctttttat ttaatatgaa tatttatttg ggcttaaggt gtaacctcct cgacataaga      720
ctcacatggc gcaggcacat tgaagacaaa aatactcatt gtcgggtctc gcaccctcca      780
gcagcaccta aaattatgtc ttcaattatt gccaacattg gagacacaat tagtctgtgg      840
cacctcag                                                              848
```

<210> SEQ ID NO 8
<211> LENGTH: 229
<212> TYPE: DNA
<213> ORGANISM: Artificial Sequence
<220> FEATURE:
<223> OTHER INFORMATION: Laccase2 - Alu Element (or complementary
      region) of Left Intron

<400> SEQUENCE: 8

```
ttcccgacta tctgataccc attacttatc taggggaat gcgaacccaa aattttatca       60
gttttctcgg atatcgatag atattgggga ataaatttaa ataaataaat tttgggcggg      120
tttagggcgt ggcaaaaagt tttttggcaa atcgctagaa atttacaaga cttataaaat      180
tatgaaaaaa tacaacaaaa ttttaaacac gtgggcgtga cagtttttgg                 229
```

<210> SEQ ID NO 9

-continued

```
<211> LENGTH: 271
<212> TYPE: DNA
<213> ORGANISM: Artificial Sequence
<220> FEATURE:
<223> OTHER INFORMATION: Laccase2 - Alu Element (or complementary
      region) of Right Intron

<400> SEQUENCE: 9
caaaactgcc atgcccacat ttttgaacta ttttcgaaat tttttcataa ttgtattact      60
cgtgtaaatt tccatcaatt tgccaaaaaa ctttttgtca cgcgttaacg ccctaaagcc     120
gccaatttgg tcacgcccac actattgaac aattatcaaa ttttttctca ttttattccc     180
caatatctat cgatatcccc gattatgaaa ttattaaatt tcgcgttcgc attcacacta     240
gctgagtaac gagtatctga tagttgggga a                                     271

<210> SEQ ID NO 10
<211> LENGTH: 15
<212> TYPE: DNA
<213> ORGANISM: Artificial Sequence
<220> FEATURE:
<223> OTHER INFORMATION: Laccase2 - Poly-pyrimidine Tract of Left Intron

<400> SEQUENCE: 10 tttttttttat tttat                                                       15

<210> SEQ ID NO 11
<211> LENGTH: 448
<212> TYPE: DNA
<213> ORGANISM: Artificial Sequence
<220> FEATURE:
<223> OTHER INFORMATION: ZKSCAN1- Left Intron

<400> SEQUENCE: 11
agtgacagtg gagattgtac agtttttttcc tcgatttgtc aggattttttt tttttttgac     60 ggagtttaac ttcttgtctc ccaggtagga agtgcagtgg cgtaatctcg gctcactaca     120
acctccacct cctgggttca agcgtttctc ctgcctcagc tttccgagta gctgggatta     180
caggcgcctg ccaccatgcc ctgctgactt ttgtattttt agtagagacg gggtttcacc     240
atgttggcca ggctggtctt gaactcctga ccgcaggcga ttggcctgcc tcggcctccc     300
aaagtgctga gattacaggc gtgagccacc accccggcc tcaggagcgt tctgatagtg      360
cctcgatgtg ctgcctccta taaagtgtta gcagcacaga tcactttttg taaaggtacg     420
tactaatgac tttttttttta tacttcag                                        448

<210> SEQ ID NO 12
<211> LENGTH: 796
<212> TYPE: DNA
<213> ORGANISM: Artificial Sequence
<220> FEATURE:
<223> OTHER INFORMATION: ZKSCAN1 - Right Intron

<400> SEQUENCE: 12
gtaagaagca aggtttcatt taggggaagg gaaatgattc aggacgagag tctttgtgct     60
gctgagtgcc tgtgatgaag aagcatgtta gtcctgggca acgtagcgag accccatctc     120
tacaaaaaat agaaaaatta gccaggtata gtggcgcaca cctgtgattc cagctacgca     180
ggaggctgag gtgggaggat tgcttgagcc caggaggttg aggctgcagt gagctgtaat     240
catgccacta ctccaacctg ggcaacacag caaggaccct gtctcaaaag ctacttacag     300
aaaagaatta ggctcggcac ggtagctcac acctgtaatc ccagcacttt gggaggctga     360
```

-continued

```
ggcgggcaga tcacttgagg tcaggagttt gagaccagcc tggccaacat ggtgaaacct      420
tgtctctact aaaaatatga aaattagcca ggcatggtgg cacattcctg taatcccagc      480
tactcgggag gctgaggcag gagaatcact tgaacccagg aggtggaggt tgcagtaagc      540
cgagatcgta ccactgtgct ctagccttgg tgacagagcg agactgtctt aaaaaaaaaa      600
aaaaaaaaaa aagaattaat taaaaattta aaaaaaaatg aaaaaagct gcatgcttgt       660 tttttgtttt tagttattct acattgttgt cattattacc aaatattggg gaaaatacaa      720
cttacagacc aatctcagga gttaaatgtt actacgaagg caaatgaact atgcgtaatg      780
aacctggtag gcatta                                                     796
```

```
<210> SEQ ID NO 13
<211> LENGTH: 326
<212> TYPE: DNA
<213> ORGANISM: Artificial Sequence
<220> FEATURE:
<223> OTHER INFORMATION: ZKSCAN1 - Alu Element (or complementary region)
      of Left Intron

<400> SEQUENCE: 13
aggatttttt tttttttgac ggagtttaac ttcttgtctc ccaggtagga agtgcagtgg       60
cgtaatctcg gctcactaca acctccacct cctgggttca agcgtttctc ctgcctcagc      120
tttccgagta gctgggatta caggcgcctg ccaccatgcc ctgctgactt ttgtattttt      180
agtagagacg gggtttcacc atgttggcca ggctggtctt gaactcctga ccgcaggcga      240
ttggcctgcc tcggcctccc aaagtgctga gattacaggc gtgagccacc accccggcc       300 tcaggagcgt tctgatagtg cctcga                                          326
```

```
<210> SEQ ID NO 14
<211> LENGTH: 282
<212> TYPE: DNA
<213> ORGANISM: Artificial Sequence
<220> FEATURE:
<223> OTHER INFORMATION: ZKSCAN1 - Alu Element (or complementary region)
      of Right Intron

<400> SEQUENCE: 14
gcacggtagc tcacacctgt aatcccagca ctttgggagg ctgaggcggg cagatcactt       60
gaggtcagga gtttgagacc agcctggcca acatggtgaa accttgtctc tactaaaaat      120
atgaaaatta gccaggcatg gtggcacatt cctgtaatcc cagctactcg ggaggctgag      180
gcaggagaat cacttgaacc caggaggtgg aggttgcagt aagccgagat cgtaccactg      240
tgctctagcc ttggtgacag agcgagactg tcttaaaaaa aa                        282
```

```
<210> SEQ ID NO 15
<211> LENGTH: 14
<212> TYPE: DNA
<213> ORGANISM: Artificial Sequence
<220> FEATURE:
<223> OTHER INFORMATION: ZKSCAN1 - Poly-pyrimidine Tract of Left Intron

<400> SEQUENCE: 15
ttttttttat actt                                                        14
```

```
<210> SEQ ID NO 16
<211> LENGTH: 144
<212> TYPE: DNA
<213> ORGANISM: Artificial Sequence
<220> FEATURE:
<223> OTHER INFORMATION: TricY Sequence
```

-continued

```
<400> SEQUENCE: 16
ccttcgatag ctcagttggt agagcggagg actgtaggcg gccgcgagac ggtcgggtcc      60
agatattcgt atctgtcgag tagagtgtgg gctcgtggcc gcggaggtat ccttaggtcg     120
ctggttcgaa tccggctcgg agga                                           144

<210> SEQ ID NO 17
<211> LENGTH: 37
<212> TYPE: DNA
<213> ORGANISM: Artificial Sequence
<220> FEATURE:
<223> OTHER INFORMATION: TricY Sequence - Left Intron

<400> SEQUENCE: 17
ccttcgatag ctcagttggt agagcggagg actgtag                               37

<210> SEQ ID NO 18
<211> LENGTH: 41
<212> TYPE: DNA
<213> ORGANISM: Artificial Sequence
<220> FEATURE:
<223> OTHER INFORMATION: TricY Sequence - Right Intron

<400> SEQUENCE: 18
gaggtatcct taggtcgctg gttcgaatcc ggctcggagg a                          41

<210> SEQ ID NO 19
<211> LENGTH: 49
<212> TYPE: DNA
<213> ORGANISM: Artificial Sequence
<220> FEATURE:
<223> OTHER INFORMATION: TricY Sequence - Broccoli Aptamer

<400> SEQUENCE: 19
gagacggtcg ggtccagata ttcgtatctg tcgagtagag tgtgggctc                  49

<210> SEQ ID NO 20
<211> LENGTH: 257
<212> TYPE: DNA
<213> ORGANISM: Artificial Sequence
<220> FEATURE:
<223> OTHER INFORMATION: HIPK3- Right Intron with Deletions

<400> SEQUENCE: 20
gtaggtaacc caactagtta agcacccca aatttgaaaa ttcgtttcct ttgagtgtca      60
tgtcaatgcc caaaaagttt cagatatttg gatttgagat gctcaacctg tataaggatt    120
cagaaagtta ttctgattaa tgattttaag attcagatat acaataatcc cagcaacttg    180
ggaggctgag gcaggagaat cacttgaacc caggagatgg aggttgcagt gagccgagat    240
catgccattg cactcca                                                   257

<210> SEQ ID NO 21
<211> LENGTH: 165
<212> TYPE: DNA
<213> ORGANISM: Artificial Sequence
<220> FEATURE:
<223> OTHER INFORMATION: HIPK3 - Left Intron with Deletions

<400> SEQUENCE: 21
gcctcagcct ctcaaagtgc taggattaca gggatctata ctacaaattg tgaatttgac     60
ccttaagagt tttcttcctg atatttaaaa ttgaaaaaaa aattgttgac attaatattt    120
```

-continued
_____

```
cttctttcct tttttttctt ttcctttttt tttttttttt tgcag                     165

<210> SEQ ID NO 22
<211> LENGTH: 626
<212> TYPE: DNA
<213> ORGANISM: Artificial Sequence
<220> FEATURE:
<223> OTHER INFORMATION: ZKSCAN1 - Right Intron with Deletions

<400> SEQUENCE: 22
gtaagaagca ggaggctgag gtgggaggat tgcttgagcc caggaggttg aggctgcagt      60
gagctgtaat catgccacta ctccaacctg ggcaacacag caaggaccct gtctcaaaag     120
ctacttacag aaaagaatta ggctcggcac ggtagctcac acctgtaatc ccagcacttt     180
gggaggctga ggcgggcaga tcacttgagg tcaggagttt gagaccagcc tggccaacat     240
ggtgaaacct tgtctctact aaaaatatga aaattagcca ggcatggtgg cacattcctg     300
taatcccagc tactcgggag gctgaggcag gagaatcact tgaacccagg aggtggaggt     360
tgcagtaagc cgagatcgta ccactgtgct ctagccttgg tgcagagcg agactgtctt      420 aaaaaaaaaa aaaaaaaaaa aagaattaat taaaaattta aaaaaaaatg aaaaaaagct     480
gcatgcttgt tttttgtttt tagttattct acattgttgt cattattacc aaatattggg     540
gaaaatacaa cttacagacc aatctcagga gttaaatgtt actacgaagg caaatgaact     600
atgcgtaatg aacctggtag gcatta                                         626

<210> SEQ ID NO 23
<211> LENGTH: 419
<212> TYPE: DNA
<213> ORGANISM: Artificial Sequence
<220> FEATURE:
<223> OTHER INFORMATION: ZKSCAN1 - Left Intron with Deletions

<400> SEQUENCE: 23
agtgacagtg gagattgtac agttttttcc tcgatttgtc aggatttttt ttttttttgac     60 ggagtttaac ttcttgtctc ccaggtagga agtgcagtgg cgtaatctcg gctcactaca    120
acctccacct cctgggttca agcgtttctc ctgcctcagc tttccgagta gctgggatta    180
caggcgcctg ccaccatgcc ctgctgactt ttgtattttt agtagagacg gggtttcacc    240
atgttggcca ggctggtctt gaactcctga ccgcaggcga ttggcctgcc tcggcctccc    300
aaagtgctga gattacaggc gtgagccacc accccggcc tcaggagcgt tctgatagtg     360
cctcgaacag atcactttt gtaaaggtac gtactaatga ctttttttt atacttcag      419

<210> SEQ ID NO 24
<211> LENGTH: 744
<212> TYPE: DNA
<213> ORGANISM: Artificial Sequence
<220> FEATURE:
<223> OTHER INFORMATION: Laccase2 - Right Intron with Deletions

<400> SEQUENCE: 24
gtaagtattc aaaagcattt ccgaccatgt aaagtatata tattcttaat aaggatcaat     60
agccgagtcg atctcgccat gtccgtctgt cttattattt tattaccgcc gagacatcag    120
gaactataaa agctagaagg atgagttta gcatacagat tctagagaca aggacgcaga     180
gcaagtttgt tgatccatgc tgccacgctt taactttctc aaattgccca aaactgccat     240
gcccacattt ttgaactatt ttcgaaattt tttcataatt gtattactcg tgtaaatttc     300
catcaatttg ccaaaaaact ttttgtcacg cgttaacgcc ctaaagccgc caatttggtc     360
```

-continued

```
acgcccacac tattgaacaa ttatcaaatt ttttctcatt ttattcccca atatctatcg    420
atatccccga ttatgaaatt attaaatttc gcgttcgcat tcacactagc tgagtaacga    480
gtatctgata gttggggaaa tcgacttatt ttttatatac aatgaaaatg aatttaatca    540
tatgaatatc gattatagct ttttatttaa tatgaatatt tatttgggct taaggtgtaa    600
cctcctcgac ataagactca catggcgcag gcacattgaa gacaaaaata ctcattgtcg    660
ggtctcgcac cctccagcag cacctaaaat tatgtcttca attattgcca acattggaga    720
cacaattagt ctgtggcacc tcag                                           744
```

```
<210> SEQ ID NO 25
<211> LENGTH: 466
<212> TYPE: DNA
<213> ORGANISM: Artificial Sequence
<220> FEATURE:
<223> OTHER INFORMATION: Laccase2 - Left Intron with Deletions

<400> SEQUENCE: 25
tcattgagaa atgactgagt tccggtgctc tcaagtcatt gatctttgtc gacttttatt     60
tggtctctgt aataacgact tcaaaaacat taaattctgt tgcgaagcca gtaagctaca    120
aaaagaaaaa acaagagaga atgctatagt cgtatagtat agtttcccga ctatctgata    180
cccattactt atctaggggg aatgcgaacc caaaatttta tcagttttct cggatatcga    240
tagatattgg ggaataaatt taaataaata aattttgggc gggtttaggg cgtggcaaaa    300
agttttttgg caaatcgcta gaaatttaca agacttataa aattatgaaa aaatacaaca    360
aaattttaaa cacgtgggcg tgacagtttt ggacggtttt agtataataa taagctaaat    420
cgagactaag ttttattgtt atatatattt tttttatttt atgcag                  466
```

```
<210> SEQ ID NO 26
<211> LENGTH: 590
<212> TYPE: DNA
<213> ORGANISM: Artificial Sequence
<220> FEATURE:
<223> OTHER INFORMATION: Encephalomyocarditis Virus IRES

<400> SEQUENCE: 26
gatccgcccc tctccctccc ccccccctaa cgttactggc cgaagccgct tggaataagg     60
ccggtgtgcg tttgtctata tgttattttc caccatattg ccgtcttttg gcaatgtgag    120
ggcccggaaa cctggccctg tcttcttgac gagcattcct aggggtcttt ccctctcgc    180 caaaggaatg caaggtctgt tgaatgtcgt gaaggaagca gttcctctgg aagcttcttg    240
aagacaaaca acgtctgtag cgaccctttg caggcagcgg aaccccccac ctggcgacag    300
gtgcctctgc ggccaaaagc cacgtgtata agatacacct gcaaaggcgg cacaacccca    360
gtgccacgtt gtgagttgga tagttgtgga aagagtcaaa tggctctcct caagcgtatt    420
caacaagggg ctgaaggatg cccagaaggt accccattgt atgggatctg atctggggcc    480
tcggtacaca tgctttacat gtgtttagtc gaggttaaaa aaacgtctag gccccccgaa    540
ccacggggac gtggttttcc tttgaaaaac acgatgataa tatggccaca              590
```

```
<210> SEQ ID NO 27
<211> LENGTH: 737
<212> TYPE: DNA
<213> ORGANISM: Artificial Sequence
<220> FEATURE:
<223> OTHER INFORMATION: Polio Virus IRES
```

-continued

```
<400> SEQUENCE: 27
ttaaaacagc tctggggttg ttcccacccc agaggcccac gtggcggcca gtacactggt      60
attgcggtac ctttgtacgc ctgttttata ctcccttccc ccgtaactta gaagcacaat     120
gtccaagttc aataggaggg ggtacaaacc agtaccacca cgaacaagca cttctgttcc     180
cccggtgagg ctgtataggc tgtttccacg gctaaaagcg gctgatccgt tatccgctca     240
tgtacttcga gaagcctagt atcaccttgg aatcttcgat gcgttgcgct caacactcaa     300
ccccagagtg tagcttaggt cgatgagtct ggacgttcct caccggcgac ggtggtccag     360
gctgcgttgg cggcctacct gtggcccaaa gccacaggac gctagttgtg aacaaggtgt     420
gaagagccta ttgagctacc tgagagtcct ccggcccctg aatgcggcta atcctaacca     480
cggagcaggc agtggcaatc cagcgaccag cctgtcgtaa cgcgcaagtt cgtggcggaa     540
ccgactactt tgggtgtccg tgtttccttt tattttaca atggctgctt atggtgacaa     600
tcattgattg ttatcataaa gcaaattgga ttggccatcc ggtgagaatt tgattattaa     660
attactctct tgttgggatt gctcctttga aatcttgtgc actcacacct attggaatta     720
cctcattgtt aagatat                                                    737

<210> SEQ ID NO 28
<211> LENGTH: 613
<212> TYPE: DNA
<213> ORGANISM: Artificial Sequence
<220> FEATURE:
<223> OTHER INFORMATION: Kaposi Sarcoma-Associated Herpesvirus (KSHV)
      vFLIP IRES

<400> SEQUENCE: 28
ttggacagac tcctacttat aaagcaggtg tccaaagaac actttcaaaa gacagggagc      60
gcctgcctgt tagtggccag taagctcaga agcctcacgc ctatttctac cagttcactt     120
tgctatgccg cggcagactc cttttcccgc caagaactta tagaccagga gaaagaactc     180
cttgagaagt tggcgtggcg aacagaggca gtcttagcga cggacgtcac ttccttcttg     240
ttacttaaat tgctgggggg ctcccaacac ctggactttt ggcaccacga ggtcaacacc     300
ctgattacaa aagccttagt tgacccaaag actggctcat tgcccgcctc tattatcagc     360
gctgcaggct gtgcgctgtt ggttcctgcc aacgtcattc cgcaggatac ccactcgggt     420
ggggtagttc ctcagctggc aagcatattg ggatgcgatg tttccgttct acaggcggca     480
gtggaacaga tcctaacatc tgtttcggac tttgatctgc gcattctgga cagctattaa     540
gcttgtgatt ttgtttaggg cggaaaaata aattttcctt tgttttttcca catcggtgcc     600 ttcacatata caa                                                        613

<210> SEQ ID NO 29
<211> LENGTH: 407
<212> TYPE: DNA
<213> ORGANISM: Artificial Sequence
<220> FEATURE:
<223> OTHER INFORMATION: Hepatitis C Virus (HCV) IRES

<400> SEQUENCE: 29
gccagccccc gattgggggc gacactccac catagatcac tcccctgtga ggaactactg      60
tcttcacgca gaaagcgtct agccatggcg ttagtatgag tgtcgtgcag cctccaggac     120
cccccctccc gggagagcca tagtggtctg cggaaccggt gagtacaccg gaattgccag     180
gacgaccggg tcctttcttg gatcaacccg ctcaatgcct ggagatttgg gcgtgccccc     240
```

-continued

```
gcgagactgc tagccgagta gtgttgggtc gcgaaaggcc ttgtggtact gcctgatagg      300
gtgcttgcga gtgccccggg aggtctcgta gaccgtgcac catgagcacg aatcctaaac      360
ctcaaagaaa aaccaaacgt aacaccaacc gccgcccaca ggacgtc                    407
```

```
<210> SEQ ID NO 30
<211> LENGTH: 32
<212> TYPE: DNA
<213> ORGANISM: Artificial Sequence
<220> FEATURE:
<223> OTHER INFORMATION: Primer #1 Specific to the Backsplice

<400> SEQUENCE: 30
ctgcttgtcg gccatgatat agacgttgtg gc                                     32
```

```
<210> SEQ ID NO 31
<211> LENGTH: 31
<212> TYPE: DNA
<213> ORGANISM: Artificial Sequence
<220> FEATURE:
<223> OTHER INFORMATION: Primer #2 Specific to the Backsplice

<400> SEQUENCE: 31
caagctgacc ctgaagttca tctgcaccac c                                      31
```

```
<210> SEQ ID NO 32
<211> LENGTH: 28
<212> TYPE: DNA
<213> ORGANISM: Artificial Sequence
<220> FEATURE:
<223> OTHER INFORMATION: Primer #1 Spanning the IRES Elements

<400> SEQUENCE: 32
ggccgacaag cagaagaacg gcatcaag                                          28
```

```
<210> SEQ ID NO 33
<211> LENGTH: 31
<212> TYPE: DNA
<213> ORGANISM: Artificial Sequence
<220> FEATURE:
<223> OTHER INFORMATION: Primer #2 Spanning the IRES Elements

<400> SEQUENCE: 33
ggtggtgcag atgaacttca gggtcagctt g                                      31
```

```
<210> SEQ ID NO 34
<211> LENGTH: 25
<212> TYPE: DNA
<213> ORGANISM: Artificial Sequence
<220> FEATURE:
<223> OTHER INFORMATION: Primer #1 for AAV2 ITRs

<400> SEQUENCE: 34
aacatgctac gcagagaggg agtgg                                             25
```

```
<210> SEQ ID NO 35
<211> LENGTH: 29
<212> TYPE: DNA
<213> ORGANISM: Artificial Sequence
<220> FEATURE:
<223> OTHER INFORMATION: Primer #2 for AAV2 ITRs

<400> SEQUENCE: 35
catgagacaa ggaacccccta gtgatggag                                        29
```

-continued

```
<210> SEQ ID NO 36
<211> LENGTH: 20
<212> TYPE: DNA
<213> ORGANISM: Artificial Sequence
<220> FEATURE:
<223> OTHER INFORMATION: Primer #1 Specific to CMV Promoter

<400> SEQUENCE: 36
caagtacgcc ccctattgac                                                  20

<210> SEQ ID NO 37
<211> LENGTH: 20
<212> TYPE: DNA
<213> ORGANISM: Artificial Sequence
<220> FEATURE:
<223> OTHER INFORMATION: Primer #2 Specific to CMV Promoter

<400> SEQUENCE: 37
aagtcccgtt gattttggtg                                                  20

<210> SEQ ID NO 38
<211> LENGTH: 23
<212> TYPE: DNA
<213> ORGANISM: Artificial Sequence
<220> FEATURE:
<223> OTHER INFORMATION: Primer #1 Specific to Lamin B2 Locus

<400> SEQUENCE: 38
ggacccaagg actacctcaa ggg                                              23

<210> SEQ ID NO 39
<211> LENGTH: 22
<212> TYPE: DNA
<213> ORGANISM: Artificial Sequence
<220> FEATURE:
<223> OTHER INFORMATION: Primer #2 Specific to Lamin B2 Locus

<400> SEQUENCE: 39
agggcacctc catctcggaa ac                                               22

<210> SEQ ID NO 40
<211> LENGTH: 32
<212> TYPE: DNA
<213> ORGANISM: Artificial Sequence
<220> FEATURE:
<223> OTHER INFORMATION: Primer #1 Specific for GFP

<400> SEQUENCE: 40
ctgcttgtcg gccatgatat agacgttgtg gc                                    32

<210> SEQ ID NO 41
<211> LENGTH: 31
<212> TYPE: DNA
<213> ORGANISM: Artificial Sequence
<220> FEATURE:
<223> OTHER INFORMATION: Primer #2 Specific for GFP

<400> SEQUENCE: 41
caagctgacc ctgaagttca tctgcaccac c                                     31

<210> SEQ ID NO 42
<211> LENGTH: 19
<212> TYPE: DNA
<213> ORGANISM: Artificial Sequence
<220> FEATURE:
<223> OTHER INFORMATION: Primer #1 Specific for GAPDH
```

```
<400> SEQUENCE: 42
ccactcctcc acctttgac                                                        19

<210> SEQ ID NO 43
<211> LENGTH: 17
<212> TYPE: DNA
<213> ORGANISM: Artificial Sequence
<220> FEATURE:
<223> OTHER INFORMATION: Primer #2 Specific for GAPDH

<400> SEQUENCE: 43
accctgttgc tgtagcc                                                          17

<210> SEQ ID NO 44
<211> LENGTH: 580
<212> TYPE: DNA
<213> ORGANISM: Artificial Sequence
<220> FEATURE:
<223> OTHER INFORMATION: CMV Promoter

<400> SEQUENCE: 44
atagtaatca attacggggt cattagttca tagcccatat atggagttcc gcgttacata     60
acttacggta aatggcccgc ctggctgacc gcccaacgac ccccgcccat tgacgtcaat    120
aatgacgtat gttcccatag taacgccaat agggactttc cattgacgtc aatgggtgga    180
gtatttacgg taaactgccc acttggcagt acatcaagtg tatcatatgc caagtacgcc    240
ccctattgac gtcaatgacg gtaaatggcc cgcctggcat tatgcccagt acatgacctt    300
atgggacttt cctacttggc agtacatcta cgtattagtc atcgctatta ccatggtgat    360
gcggttttgg cagtacatca atgggcgtgg atagcggttt gactcacggg gatttccaag    420
tctccacccc attgacgtca atgggagttt gttttggcac caaaatcaac gggactttcc    480
aaaatgtcgt aacaactccg ccccattgac gcaaatgggc ggtaggcgtg tacggtggga    540
ggtctatata agcagagctg gtttagtgaa ccgtcagatc                          580

<210> SEQ ID NO 45
<211> LENGTH: 229
<212> TYPE: DNA
<213> ORGANISM: Artificial Sequence
<220> FEATURE:
<223> OTHER INFORMATION: SV40 Poly-A

<400> SEQUENCE: 45
tgatcataat cagccatacc acatttgtag aggttttact tgctttaaaa aacctcccac     60
acctccccct gaacctgaaa cataaaatga atgcaattgt tgttgttaac ttgtttattg    120
cagcttataa tggttacaaa taaagcaata gcatcacaaa tttcacaaat aaagcatttt    180
tttcactgca ttctagttgt ggtttgtcca aactcatcaa tgtatctta                229

<210> SEQ ID NO 46
<211> LENGTH: 52
<212> TYPE: DNA
<213> ORGANISM: Artificial Sequence
<220> FEATURE:
<223> OTHER INFORMATION: Back-splice junction

<400> SEQUENCE: 46
tcaagtccgc catgcccgaa ggctacgtcc aggagcgcac catcttcttc aa              52

<210> SEQ ID NO 47
<211> LENGTH: 53
```

-continued

```
<212> TYPE: DNA
<213> ORGANISM: Artificial Sequence
<220> FEATURE:
<223> OTHER INFORMATION: Poliovirus IRES

<400> SEQUENCE: 47
gccgggatca ctctcggcat ggacgagctg tacaaatata ccatggtgag caa          53

<210> SEQ ID NO 48
<211> LENGTH: 53
<212> TYPE: DNA
<213> ORGANISM: Artificial Sequence
<220> FEATURE:
<223> OTHER INFORMATION: KSHV vFLIP IRES

<400> SEQUENCE: 48
gccgggatca ctctcggcat ggacgagctg tacaagtgcc ttcacatata caa          53
```